(12) United States Patent
Bakonyi et al.

(10) Patent No.: US 11,634,743 B2
(45) Date of Patent: Apr. 25, 2023

(54) COUPLED, SELF-SUFFICIENT BIOTRANSFORMATION OF CHENODEOXCHOLIC ACID TO URSODEOXYCHOLIC ACID AND NOVEL ENZYME MUTANTS APPLICABLE IN SAID PROCESS

(71) Applicant: Pharmazell GmbH, Raubling (DE)

(72) Inventors: Daniel Bakonyi, Cologne (DE); Werner Hummel, Titz (DE); Ralf Gross, Stephanskirchen (DE)

(73) Assignee: Pharmazell GmbH, Raubling (DE)

( * ) Notice: Subject to any disclaimer, the term of this patent is extended or adjusted under 35 U.S.C. 154(b) by 742 days.

(21) Appl. No.: 16/309,580

(22) PCT Filed: Jun. 19, 2017

(86) PCT No.: PCT/EP2017/064924
§ 371 (c)(1),
(2) Date: Dec. 13, 2018

(87) PCT Pub. No.: WO2017/220486
PCT Pub. Date: Dec. 28, 2017

(65) Prior Publication Data
US 2020/0407766 A1 Dec. 31, 2020

(30) Foreign Application Priority Data
Jun. 20, 2016 (EP) .................................... 16175318

(51) Int. Cl.
C12N 9/04 (2006.01)
C12P 7/26 (2006.01)
C12P 33/02 (2006.01)

(52) U.S. Cl.
CPC ............ *C12P 33/02* (2013.01); *C12N 9/0006* (2013.01); *C12Y 101/01159* (2013.01); *C12Y 101/01201* (2013.01)

(58) Field of Classification Search
None
See application file for complete search history.

(56) References Cited

FOREIGN PATENT DOCUMENTS

| CN | 105274070 A | 1/2016 | |
|---|---|---|---|
| EP | 2105500 A1 * | 9/2009 | ........... C12N 9/0006 |
| EP | 2105500 A1 | 9/2009 | |
| WO | 2016016213 A1 | 2/2016 | |

OTHER PUBLICATIONS

Lou et al., Sci. Rep. 6:22885, 2016, 11 pages (Year: 2016).*
Lepercq et al., "Isolates from Normal Human Intestinal Flora but not Lactic Acid Bacteria Exhibit 7α- and 7β-Hydroxysteriod Dehydrogenase Activities", Microb. Ecol. Health Dis. 16, 195-201, 2004.
Kakiyama et ai., "Modulation of the Fecal bile Acid Profiled by Gut Microbiota in Cirrhosis", J Hepatol., vol. 58, 949-955, 2013.
Ji et al., "Cloning, expression and Characterization of a Putative 7α-hydroxysteroid Dehydrogenase in Comamonas Testosteroni", Microbiol Res., 169(2-3), 148-154, 2014.
Hylemon et al., "Multiple Forms of 7-α-Hydroxysteroid Dehydrogenase in Selected Strains of Bacteroides Fragilis" J. Bacteriol. vol. 122, No. 2, 418-424, 1975.
Hirano et ai., "Characterizaion of NADP-Dependent 7β-Hydroxysteriod Dehydrogenases from Peptostreptococcus Productus and Eubacterium Aerofaciens", Appl. Environ. Microbiol., 43(5), 1057-1063, 1982.
Giovannini et ai., "7α- and 12α-Hydroxysteroid Dehydrogenases from Acinetobacter Calcoaceticus Lwoffii: a new integrated chemo-enzymatic route to ursodeoxycholic acid", Steroids, 73,1385-1390, 2008.
Franklund et al., "Purification and Characterization of a Microbial, NADP-Dependent Bile Acid 7α-Hydroxysteroid Dehydrogenase", J. Biol. Chem 1990, 9842-9849, 1990.
Ferrandi et al., "Exploitation of a Laccase/Meldola's Blue System for NAD+ Regeneration in Preparative Scale Hydroxysteroid Dehydrogenase-Catalyzed Oxidations", Adv. Synth. Catal., 354, 2821-2828, 2012.
Eggert et al., "enzymatic Routes for the Synthesis of Ursodeoxycholic Acid", J. Biotechnol. 191, 11-21, 2014.
Coleman et al., "Characterization and Regulation of the NADP-Linked 7α-Hydroxysteriod Dehydrogenase Gene from Clostridium sordellii", J. Bacteriol., 176, 4865-4874, 1994.
Ciaula et al., "Targets for Current Pharmacologic Therapy in Cholesterol Gallstone Disease", Gastroenterol Clin. N. Am., 39, 245-264, 2010.
Bennett et al., "Cloning and Characterization of the NAD-Dependent 7α-Hydroxysteroid Dehydrogenase from Bacteroides Fragilis", curr. Microbiol. 47, 475-484, 2003.
Baron et al., "Cloning, Sequencing, and Expression of the Gene Coding for Bile Acid 7α-Hydroxysteroid Dehydrogenase from *Eubacterium* sp. Strain VPI 12708", J, Bacteriol. 173, 4865-4874, 1994.
Zhu et al., Enzymatic Enantioselective Reduction of α-Ketoesters by a Thermostable 7α-Hydroxysteroid Dehydrogenase from Bacteroides Fragilis, Tetrahedron 62(18), 4535-4539, 2006.
Yoshimoto et al., "Cloning and Sequencing of the 7α-Hydroxysteroid Dehydrogenase Gene from *Escherichia coli* HB101 and Characterization of the Expressed Enzyme", J. Bacteriol., 173, 2173-2179, 1991.
Prabha et al., "Review: Bacterial Transformations of Bile Acids", World J. Microbiol. Biotechnol., 22, 191-196, 2006.

(Continued)

*Primary Examiner* — David Steadman
(74) *Attorney, Agent, or Firm* — Saul Ewing LLP; Brian R. Landry; Justin W. Crotty

(57) ABSTRACT

The present invention relates to a coupled biotransformation process of converting chenodeoxycholic acid (CDCA) and related compounds to ursodeoxycholic acid (UDCA) and related compounds. It also relates to the cloning, expression, and biochemical characterization of a novel $NADP^+$-dependent 7α-hydroxysteroid dehydrogenase (7α-HSDH) from *Clostridium difficile*, cofactor switch mutants thereof, and their application for the oxidation of bile acids. A further aspect of the invention relates to novel NADP-dependent cofactor switch mutants of the $NADP^+$-dependent 7α-HSDH of *E. coli* and their application for the oxidation of bile acids.

15 Claims, 11 Drawing Sheets
Specification includes a Sequence Listing.

(56) References Cited

OTHER PUBLICATIONS

Monti et al., "One-Pot Muitienzymatic Synthesis of 12-Ketoursodeoxycholic Acid: Subtle Cofactor Specificities Rule the Reaction Equilibria of Five Biocatalysts Wroking in a Row", Adv. Synth Catal, 351, 1303-1311, 2009.
Medici et al., "7α-OH epimerisation of Bile Acids via Oxido-Reductio nwith Xanthomonas Maltophilia", Steroids, 67, 51-56, 2002.
Macdonald et al., "Epimerization Versus Dehydroxylation of the 7α-Hydroxyl- Group of Primary Bile Acids: Competitive Studies with Clostridium Absonum and 7α-Dehydroxylating Bacteria (*Eubacterium* SP.)", J. Steroid Biochem., 17, 295-303, 1982.
Macdonald et al.,, "Formation of Ursodeoxycholid Acid from Chenodeoxycholic Acid by a 7β-Hydroxysteriod Dehydrogenase-Elaborating Eubacterium aerofaciens Strain Cocultured with 7α-Hydroxysteriod Dehydrogenase-Elaborating Organisms", Biochim. Biophys. Acta. 665(2), 262-269, 1981.
Macdonald et al., "Bile Salt Induction of 7α- and 7β-Hydroxysteriod Dehydrogenases in Clostridium Absonum", Appl. Environ. Microbiol., 44, 1187-1195, 1982.
Liu et al., "The Catalytic Promiscuity of a Microbial 7α-Hydroxysteriod Dehydrogenase, Reduction of Non-Steroidal Carbonyl Compounds", 76, 1136-1140, 2011.
Zheng, M.-M. et al.: "Two-step enzymatic synthesis of ursodeoxycholic acid with a new 7beta-hydroxysteroid dehydrogenase from Ruminococcus torques", Process Biochemistry, vol. 50, No. 4, Jan. 17, 2015, pp. 598-604, XP029149798.

Pedrini, P. et al.: "Xanthomonas rnaltophilia CBS 897.97 as a source of new ?beta- and 7alpha-hydroxysteroid dehydrogenases and cholylglycine hydrolase: Improved biotransformations of bile acids", Steroids, vol. 71, No. 3, Mar. 2006, pp. 189-198, XP027987139.
Database Protein, database accession No. WP 024213374, ANONYM.: "7-alpha-hydroxysteroid dehydrogenase [*Escherichia coli*]", Feb. 17, 2014, XP002762262.
Database WPI, Thomson Scientific, London, GB, AN 2016-131900, week 201642, XP002773599 & CN 10527070 A (Liu Z) Jan. 27, 2016, abstract.
Bakonyi, D. & Hummel, W.: "Cloning, expression, and biochemical characterization of a novel NADP+-dependent 7 [alpha]-hydroxysteroid dehydrogenase from Clostridium difficile and its application for the oxidation of bile acids", Enzyme and Microbial Technology, vol. 99, Dec. 27, 2016, pp. 16-24, DOI: 10.1016/J.ENZMICTEC.2016.12.006, XP029916739.
Bakonyi, D. & Hummel, W.: "Appendix A. Supplementary data", Dec. 27, 2016, retrieved from the internet URL:http://www.sciencedirect.com/science/article/pii/S0141022916302575?via%3Dihub#sec0120, [retrieved on Sep. 7, 2017], XP002773600.
International Preliminary Report on Patentability dated Oct. 11, 2018 for International Application No. PCT/EP2017/064924.
Written Opinion of the International Preliminary Examining Authority dated Sep. 1, 2018 for International application No. PCT/EP2017/064924.
International Search Report issued by the International Searching Authority dated Jan. 5, 2018 for International application No. PCT/EP2017/064924.

* cited by examiner

```
                                    (G)
                                 AxxxGxG
Clodiff    1 -----MEKLQG.IAVV.ATK..LASAEILAKN.AT.YLAAR.SEELAHEVINKISA 52
Ecoli      1 MFNSDNLRLDG.CAII.GAGA..KEIAITFATA.AS.VVSD.NADAANHVVDEIQQ 57
Cloperf    1 -----MKRLDE.IAIV.ASP..GFACAHTLAMN.AL.YIAG.EEEG---AIEKILE 49
Bacfrag    1 -----MNRFEN.III.GAAG..SASTTRRIVSE.GK.VIADYSREKADQFAAELSN 52
Closord    1 -----MNKLEN.VALV.SATR..LASAIKLAQN.AI.YMG.RR.EATQEICDKYKE 52

Clodiff   53 E.GCAKFVYE.NAREEETFTSM.EEVKKE.KID..VNF.STNPSLDKDLVTGDTDN 109
Ecoli     58 L.GQAFACRC.DITSEQELSALADFAI.SKL.KV...NA.GGGPKP----FDMPMAD 110
Cloperf   50 D.GQAKFIYE.NAKERDSYFKM.DTVYENE.KID..VNY.ATNVKLDRNLVDGDTDA 106
Bacfrag   53 S.ADVRPVYF.SATELKSCKEL.TFTMKEY.DI.VL.NV.GTNPRRDTNIETLDMDY 109
Closord   53 E.LILKPVFE.DAYNIDIYKEM.DTIIKNE.KID..VNF.TGRREKDLDVNGDEDT 109
                                                       .           .  .

Clodiff  110 .FDTVNT.LKSVYLPCKAA.HMI.KNGK.S.VN.SS.IGSVLPDLSRIA.CVS.AAIN 166
Ecoli    111 .RRAYEL.VFSFFHLSQLVA.EME.KNGG.V.LT.T.MAAENKNINMTS.ASS.AAAS 167
Cloperf  107 .FDILKS.IESVYLTSKRTV.YMI.KNGG.S.IN.S.VGSIVPDLSRMA.CVS.SAIN 163
Bacfrag  110 .DEAFHL.LSCTMYLSQLVI.INS.TGGG.N.VNVAS.SGITADSNGTL.GAS.AGVI 166
Closord  110 .FELFNY.VGSVYRLSKLII.HMI.ENKG.S.VN.SS.VGGSIPDISRIG.GVS.SGVN 166

Clodiff  167 SL.TQN.ATQYAKDNV.CNAVL.GL.A.KAALDNMSP.F.IKEF.KHVPLNR.GE.DI 223
Ecoli    168 HL.VRNM.FDLGEKNI.VNGIAPGA.L.DALKSVITP.I.EQKML.QHTPIRRL.CP.DI 224
Cloperf  164 SL.TQN.ALQYAKON.RCNAVL.GL.A.KAALNNMSD.FRESF.VKHVPLNR.VGD.DI 220
Bacfrag  167 NL.TKY.ATQTGKKN.RCNAVA.GL.L.PAALNNLNE.VRKIF.LGQCATPYL.GE.DV 223
Closord  167 NI.TKQ.IIQYAKYG.RCNAVL.GL.A.IDAAMNSMPD.FRKSF.LSHVPLNR.GN.EI 223

Clodiff  224 .KAVL.YA-.DDSSFIT.DLLE.A..FGLPT.QFADNILG----  SEQ ID NO: 34  262
Ecoli    225 .NAAL.LC-.PAASWVS.QILT.S..GVQELN------------  SEQ ID NO: 37  256
Cloperf  221 .NTV.YYA-.DESNYVT.MIHE.A..FALGT.QYAEYMYLMGK-  SEQ ID NO: 58  262
Bacfrag  224 .ATIA.LA-.EDARYIT.QTIV.D..LTIHNPTINLV-------  SEQ ID NO: 59  259
Closord  224 .NSVL.FVP.EDSSYIT.SILE.S..YNLGTPQYAEFVGSKVVE  SEQ ID NO: 60  267
```

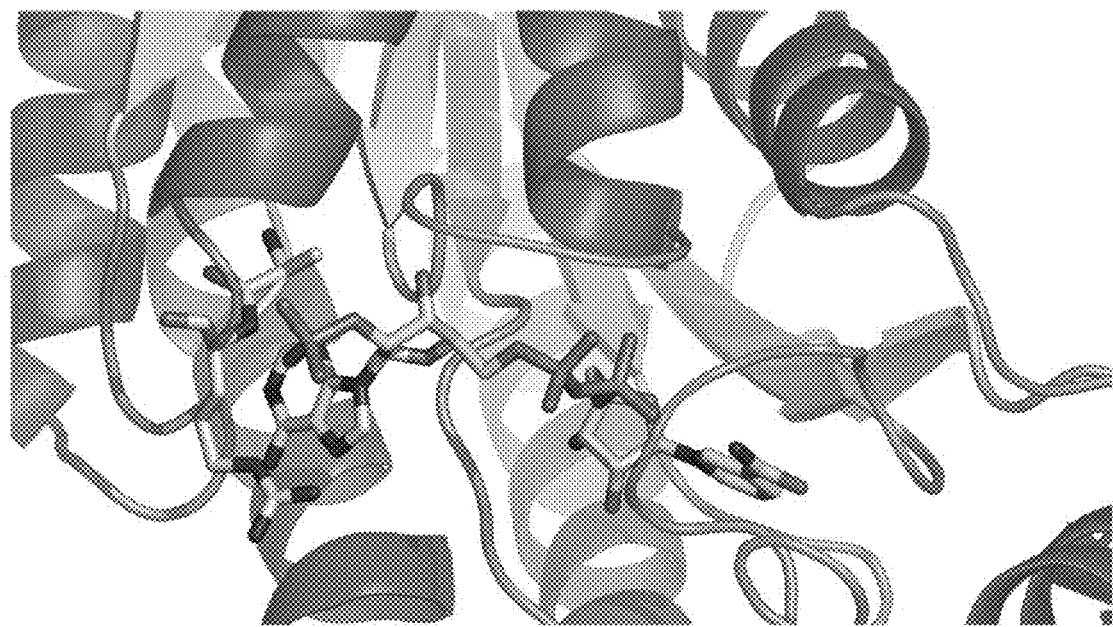
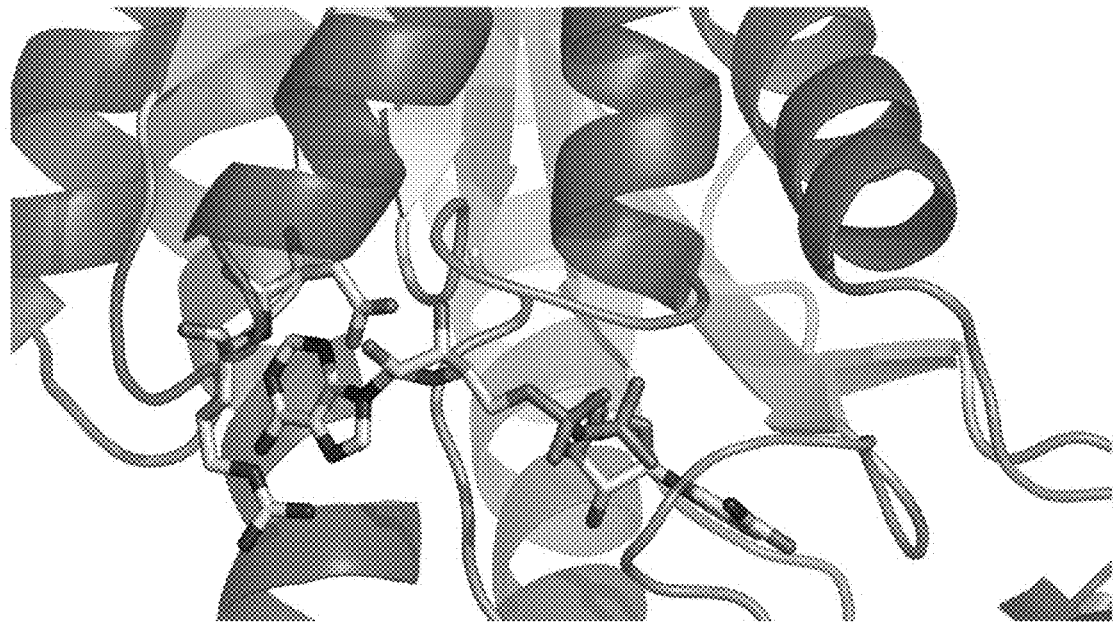
Fig. 7

COUPLED, SELF-SUFFICIENT BIOTRANSFORMATION OF CHENODEOXCHOLIC ACID TO URSODEOXYCHOLIC ACID AND NOVEL ENZYME MUTANTS APPLICABLE IN SAID PROCESS

CROSS-REFERENCE TO RELATED APPLICATIONS

This application is the U.S. national phase, pursuant to 35 U.S.C. § 371, of PCT international application Ser. No. PCT/EP2017/064924, filed Jun. 19, 2017, designating the United States and published in English on Dec. 28, 2017 as publication WO 2017/220486 A2, which claims priority under 35 U.S.C. § 119(a) to European patent application No. 16175318.1, filed Jun. 20, 2016. The entire disclosures of the aforementioned patent applications are hereby incorporated herein by reference.

The present invention relates to a coupled biotransformation process of converting chenodeoxycholic acid (CDCA) and related compounds to ursodeoxycholic acid (UDCA) and related compounds. It also relates to the cloning, expression, and biochemical characterization of a novel $NADP^+$-dependent 7α-hydroxysteroid dehydrogenase (7α-HSDH) from *Clostridium difficile*, cofactor switch mutants thereof, and their application for the oxidation of bile acids. A further aspect of the invention relates to novel NADP-dependent cofactor switch mutants of the $NAD^+$ dependent 7α-HSDH of *E. coli* and their application for the oxidation of bile acids.

SEQUENCE LISTING

The ASCII text file named "Sequence Listing", created on Sep. 26, 2022, comprising 68 kilobytes, is hereby incorporated by reference in its entirety.

BACKGROUND OF THE INVENTION

Bile acids are the biochemical components for absorption, emulsification, and digestion of lipids. They are synthesized from cholesterol in the liver as unconjugated bile salt and then conjugated with glycine and taurine. Primary bile acids in human bile are cholic acid (CA) and chenodeoxycholic acid (CDCA), whereas the secondary bile acids deoxycholic acid (DCA) and lithocholic acid (LCA) are produced from CA and CDCA by intestinal bacteria through hydrolysis of the side-chain amide bonds and dehydroxylation at C-7.

Besides the dehydroxylation of the α-positioned OH group at C-7 this alcohol group of CA or CDCA can alternatively be oxidized by 7α-hydroxysteroid dehydrogenase (EC 1.1.1.159) (7α-HSDH) from intestinal bacterial flora to 7-ketodeoxycholic acid or 7-ketolithocholic acid, respectively. Two types of microbial enzymes are described depending on either $NAD^+$ or $NADP^+$. $NAD^+$-dependent enzymes were obtained from *Escherichia coli* (T. Yoshimoto, H. Higashi, A. Kanatani, X. Lin, H. Nagai, H. Oyama, et al., Cloning and sequencing of the 7α-Hydroxysteroid Dehydrogenase gene from *Escherichia coli* HB101 and characterization of the expressed enzyme., J. Bacteriol. 173 (1991) 2173-2179) *Bacteroides fragilis* (M. Bennett, S. McKnight, J. Coleman, Cloning and Characterization of the NAD-dependent 7α-Hydroxysteroid Dehydrogenase from *Bacteroides fragilis*., Curr. Microbiol. 47 (2003) 475-484. doi:10.1007/s00284-003-4079-4), *Brevibacterium fuscum* (V. Prabha, M. Ohri, Review: Bacterial transformations of bile acids, World J. Microb. Biot. 22 (2005) 191-196. doi:10.1007/s11274-005-9019-y), *Stenotrophomonas maltophilia* (formerly *Xanthomonas maltophilia*) (A. Medici, P. Pedrini, E. Bianchini, G. Fantin, A. Guerrini, B. Natalini, et al., 7α-OH epimerisation of bile acids via oxido-reduction with *Xanthomonas maltophilia*., Steroids. 67 (2002) 51-6. P. Pedrini, E. Andreotti, A. Guerrini, M. Dean, G. Fantin, P. Giovannini, *Xanthomonas maltophilia* CBS 897.97 as a source of new 7β- and 7α-Hydroxysteroid Dehydrogenases and cholylglycine hydrolase: improved biotransformations of bile acids, Steroids. 71 (2005) 189-98. doi:10.1016/j.steroids.2005.10.002), and *Acinetobacter calcoaceticus* (P. Giovannini, A. Grandini, D. Perrone, P. Pedrini, G. Fantin, M. Fogagnolo, 7α- and 12α-Hydroxysteroid dehydrogenases from *Acinetobacter calcoaceticus lwoffii*: a new integrated chemo-enzymatic route to ursodeoxycholic acid., Steroids. 73 (2008) 1385-1390. doi:10.1016/j.steroids.2008.06.013) whereas $NADP^+$-dependent enzymes were found in *Clostridium* (J. Coleman, L. Hudson, M. Adams, Characterization and regulation of the NADP-linked 7alpha-Hydroxysteroid Dehydrogenase gene from *Clostridium sordellii*., J. Bacteriol. 176 (1994) 4865-74.), *Eubacterium* sp. strain VPI 12708 ([9] C. Franklund, Purification and Characterization of a microbial, NADP-dependent bile acid 7α-Hydroxysteroid Dehydrogenase, J. Biol. Chem. (1990) 9842-9849; S. Baron, C. Franklund, P. Hylemon, Cloning, sequencing, and expression of the gene coding for bile acid 7α-Hydroxysteroid dehydrogenase from *Eubacterium* sp. strain VPI 12708., J. Bacteriol. 173 (1991) 4558-69.) and just recently published in *Pseudomonas testosteroni* (W. Ji, Y. Chen, H. Zhang, X. Zhang, Z. Li, Y. Yu, Cloning, expression and characterization of a putative 7α-Hydroxysteroid dehydrogenase in *Comamonas testosteroni*). Some strains of *Bacteroides fragilis* contain at least two 7α-HSDH, one depending on $NAD^+$ and one on $NADP^+$ (P. Hylemon, J. Sherrod, Multiple Forms of 7α-Hydroxysteroid Dehydrogenase in Selected Strains of *Bacteroides fragilis*, J. Bacteriol. 122 (1975) 418-424.).

7α-HSDH belongs to the large family of alcohol dehydrogenases (ADHs). Due to the high enantioselectivity of these reactions ADHs have gained great significance to obtain enantiopure substances. Among cyclic compounds, steroids have an exceptional position due to their fused ring-system and various hydroxy and keto groups, requiring regio- and diastereoselective enzymes for biocatalytic modification. On this fact, a great amount of HSDHs accept only substrates which have a steran as backbone. Only a few HSDHs like the 7α-HSDH from *B. fragilis* have a promiscuity to non-steroidal carbonyl compounds (Y. Liu, T. Lv, J. Ren, M. Wang, Q. Wu, D. Zhu, The catalytic promiscuity of a microbial 7α-hydroxysteroid dehydrogenase. Reduction of non-steroidal carbonyl compounds., Steroids. 76 (2011) 1136-40. doi:10.1016/j.steroids.2011.05.001).

For preparative applications, 7α-HSDHs are of interest converting CDCA into ursodeoxycholic acid (UDCA) (Scheme 1). The epimerization of the hydroxy group at C-7 can be reached enzymatically oxidizing this group by a 7α-HSDH followed by reduction applying a 7β-HSDH.

Scheme 1: Epimerization of chenodeoxycholic acid (CDCA) into ursodeoxycholic acid (UDCA)

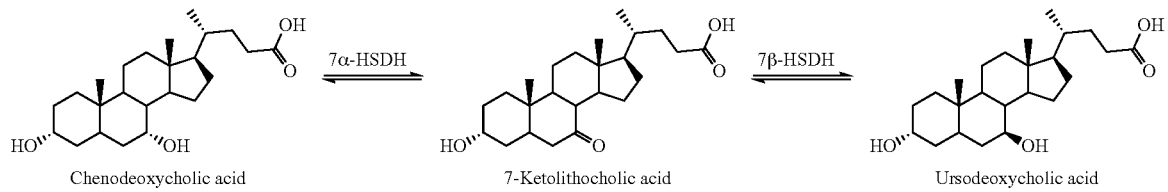

Chenodeoxycholic acid          7-Ketolithocholic acid          Ursodeoxycholic acid UDCA is a naturally low-occurring bile acid in humans, representing normally less than 4% of total biliary acids (P. Lepercq, P. Gérard, F. Béguet, J.-P. Grill, P. Relano, C. Cayuela, et al., Isolates from normal human intestinal flora but not lactic acid bacteria exhibit 7α- and 7β-hydroxysteroid dehydrogenase activities, Microb. Ecol. Heal. Dis. 16 (2004) 195-201). As therapeutic agent it can be used for the treatment of various liver diseases, such as primary biliary cirrhosis or in cholesterol gallstones dissolution therapy (A. Di Ciaula, D. Wang, H. Wang, L. Bonfrate, P. Portincasa, Targets for current pharmacologic therapy in cholesterol gallstone disease., Gastroenterol. Clin. N. 39 (2010) 245-264. doi:10.1016/j.gtc.2010.02.005; G. Kakiyama, W. Pandak, P. Gillevet, P. Hylemon, D. Heuman, K. Daita, et al., Modulation of the fecal bile acid profile by gut microbiota in cirrhosis., J. Hepatol. 58 (2013) 949-955. doi:10.1016/j.jhep.2013.01.003.). UDCA and CDCA, among others, have been used for many years for the drug treatment of gallstone disease.

Several efforts were published concerning the enzyme-catalyzed epimerization of CDCA, for example using whole cells of *Clostridium absonum* (I. A. Macdonald, D. M. Hutchison, Epimerization versus dehydroxylation of the 7α-hydroxyl-group of primary bile acids: Competitive studies with *Clostridium absonum* and 7α-dehydroxylating bacteria (*Eubacterium* sp.), J Steroid Biochem. 17 (1982) 287-293. doi:10.1016/0022-4731(82)90203-5), or *Eubacterium aerofaciens* (now *Collinsella aerofaciens*) (I. Macdonald, Y. Rochon, L. Holdeman, Formation of ursodeoxycholic acid from chenodeoxycholic acid by a 7β-Hydroxysteroid Dehydrogenase-elaborating Eubacterium aerofaciens strain cocultured with 7α-Hydroxysteroid Dehydrogenase-elaborating organisms, Appl. Environ. Microbiol. 44 (1982) 1187-1195. doi:0099-2240/82/1 11187-09$02.00/0) or isolated enzymes for example from *Xanthomonas maltophilia* (see Perdinie, above) (for a comprehensive review see T. Eggert, D. Bakonyi, W. Hummel, Enzymatic routes for the synthesis of ursodeoxycholic acid, J. Biotechnol. 191 (2014) 11-21. doi:10.1016/j.jbiotec.2014.08.006). One drawback is the use of an appropriate method to regenerate the oxidized coenzyme. Another disadvantage of the enzymes used so far comes from the incomplete enzymatic oxidation of CDCA due to a strong substrate inhibition of 7α-HSDH. For example, by using the enzyme from *Clostridium absonum* the maximum reaction rate can be achieved only at low concentrations of substrate in the range of about 1 mM before the effect of substrate inhibition becomes relevant (E. Ferrandi, D. Monti, I. Patel, R. Kittl, D. Haltrich, S. Riva, et al., Exploitation of a Laccase/Meldola's Blue System for NAD+ Regeneration in Preparative Scale Hydroxysteroid Dehydrogenase-Catalyzed Oxidations, Adv. Synth. Catal. 354 (2012) 2821-2828. doi:10.1002/adsc.201200429.).

Various other processes are described in the prior art for the preparation of UDCA, which are carried out purely chemically or consist of a combination of chemical and enzymatic process steps. The starting point is in each case cholic acid (CA) or CDCA prepared from CA.

Thus, the classical chemical method for UDCA preparation can be represented schematically as follows:

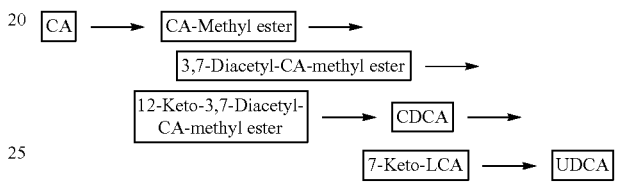

A serious disadvantage is, among other things, the following: as the chemical oxidation is not selective, the carboxyl group and the 3a and 7α-hydroxyl group must be protected by esterification.

An alternative chemical/enzymatic process based on the use of the enzyme 12α-hydroxysteroid dehydrogenase (12α-HSDH) can be represented as follows and is for example described in PCT/EP2009/002190 of the present applicant.

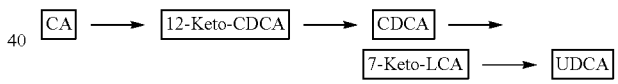

The 12α-HSDH oxidizes CA selectively to 12-keto-CDCA. The two protection steps required according to the classical chemical method are then omitted.

Furthermore, Monti, D., et al., (*One-Pot Multienzymatic Synthesis of 12-Ketoursodeoxycholic Acid: Subtle Cofactor Specificities Rule the Reaction Equilibria of Five Biocatalysts Working in a Row*. Advanced Synthesis & Catalysis, 2009) describe an alternative enzymatic-chemical process, which can be represented schematically as follows:

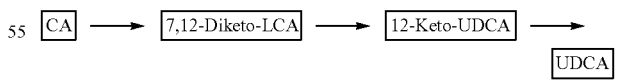

The CA is first oxidized from 7α-HSDH from *Bacteroides fragilis* ATCC 25285 (Zhu, D., et al., Enzymatic enantioselective reduction of-ketoesters by a thermostable 7-hydroxysteroid dehydrogenase from Bacteroides fragilis. Tetrahedron, 2006. 62(18): p. 4535-4539) and 12α-HSDH to 7,12-diketo-LCA. These two enzymes are each NADH-dependent. After reduction by 7β-HSDH (NADPH-dependent) from *Clostridium absonum* ATCC 27555 (DSM 599) (MacDonald, I. A. and P. D. Roach, Bile induction of 7 alpha- and 7 beta-hydroxysteroid dehydrogenases in *Clostridium absonum*. Biochim Biophys Acta, 1981. 665(2): p. 262-9), 12-keto-UDCA is formed. The end product is obtained by Wolff-Kishner reduction. This method has the drawback that owing to the position of the equilibrium of the catalyzed reaction, a complete reaction is not possible, and that for the first step of the reaction it is necessary to use two different enzymes, which makes the process more expensive. For cofactor regeneration, lactate dehydrogenase (LDH; for regeneration of NAD$^+$) and glucose dehydrogenase (GlcDH or GDH, for regeneration of NADPH) are used. A disadvantage with the cofactor regeneration used there is that the resultant co-product can only be removed from the reaction mixture with great difficulty, so that the reaction equilibrium cannot be influenced positively, which results in incomplete reaction of the educt.

A 7β-HSDH from the strain *Collinsella aerofaciens* ATCC 25986 (DSM 3979; formerly *Eubacterium aerofaciens*) was described in the year 1982 by Hirano and Masuda (Hirano, S. and N. Masuda, *Characterization of NADP-dependent 7 beta-hydroxysteroid dehydrogenases from Peptostreptococcus productus and Eubacterium aerofaciens*. Appl Environ Microbiol, 1982. 43(5): p. 1057-63).

WO2011/064404 describes a novel 7β-HSDH from *Collinsella aerofaciens* ATCC 25986, which has a molecular weight (in SDS-gel electrophoresis) of about 28-32 kDa, a molecular weight (in gel filtration, in nondenaturing conditions, such as in particular without SDS) from about 53 to 60 kDa, and the capacity for stereoselective reduction of the 7-carbonyl group of 7-keto-LCA to a 7β-hydroxyl group.

In addition, in WO2011/064404, a process is provided for the preparation of UDCA, which can be represented schematically as follows:

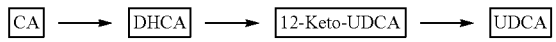

In this case the oxidation of CA takes place simply, by a classical chemical route. DHCA is reduced by the pair of enzymes 7β-HSDH and 3α-HSDH individually in succession or in one pot to 12-keto-UDCA. Combined with Wolff-Kishner reduction, UDCA can therefore be synthesized from CA in just three steps. 7β-HSDH is dependent on the cofactor NADPH, whereas 3α-HSDH requires the cofactor NADH. The availability of pairs of enzymes with dependence on the same cofactor or extended dependence (e.g. on the cofactors NADH and NADPH) would be advantageous, because this could simplify cofactor regeneration.

Novel mutants of 7β-HSDH from *Collinsella aerofaciens* with improved activity and/or altered cofactor usage are described in WO2012/080504, WO2015/197698 and WO2016/016213 of the present applicant, which are particularly referred to herewith.

A first problem to be solved by the invention relates to the provision of novel approaches for the biocatalytic preparation of UDCA and related compounds.

A further problem to be solved by the invention relates to the provision of novel, improved biocatalysts applicable in such novel biocatalytic approaches for the biocatalytic preparation of UDCA and related compounds.

SUMMARY OF THE INVENTION

The above problems were solved, surprisingly, by the provision of a coupled—self-sufficient biocatalytic epimerisation of CDCA into UDCA by applying suitable combinations of 7α-HSDH and 7β-HSDH enzymes capable of utilizing the same cofactor system. The epimerization was successfully performed with isolated enzymes of whole cell biocatalysts expressing suitable combinations of 7α-HSDH and 7β-HSDH enzymes.

The above problems were solved, surprisingly, by the provision of novel 7α-HSDH enzymes which are applicable in such epimerization reactions in combination with known 7β-HSDH enzymes.

In one aspect, a gene encoding a novel 7α-specific NADP$^+$-dependent HSDH from *Clostridium difficile* was cloned and heterologously expressed in *Escherichia coli*. The enzyme was purified using an N-terminal hexa-his-tag and biochemically characterized. Contrary to other known 7α-HSDHs, for example from *Clostridium sardiniense* or *E. coli*, the enzyme from *C. difficile* does not display a substrate inhibition. In order to demonstrate the applicability of this enzyme, biotransformation of the bile acid CDCA into 7-ketolithocholic acid (7-KLCA) was carried out with simultaneous regeneration of NADP$^+$ using an NADPH oxidase resulted in a complete conversion (<99%). Furthermore, by a structure-based site-directed mutagenesis, cofactor specificity of the 7α-HSDHs from *Clostridium difficile* was altered to accept NAD(H).

In another aspect novel mutants of the NAD(H)-dependent 7α-HSDH from *Escherichia coli* were provided, which mutants utilize the cofactor NADP(H). The mutants were also provided with C- or N-terminal hexa-his-tag for better purification.

DESCRIPTION OF THE FIGURES

FIG. 1: Amino acid sequence alignment of the hydroxysteroid dehydrogenases from *C. difficile* (DSM 12056) with several published 7α-HSDHs. The sequences of *Escherichia coli*, *Clostridium perfringens*, *Bacteroides fragilis* and *Clostridium sordellii* are compared with the protein sequence of the hydroxysteroid dehydrogenases from *C. difficile*. The amino acid residues involved in coenzyme specificity are indicated in a black frame and the catalytic triade is indicated with a star. The glycine-motif G(A) XXXGXG (SEQ ID NO: 57) is indicated as described. Shaded boxes in black indicate conserved amino acids, grey ones highlight similar amino acids. The alignment was created with clustalOmega and for visualization the jalview alignment tool was used.

FIG. 6: Amino acid sequence alignment of the NAD+-binding region of strictly NAD+-dependent HSDHs (*E. coli, Bacillus fragilis* and *Pseudomonas testosteroni* in comparison with the NADP+-dependent enzyme from *Clostridium difficile*. The conserved NAD+-binding motif G(A) XXXGXG (SEQ ID NO: 57) is marked by asterisk, the important negatively charged residue 18 amino acids downstream which is responsible for the binding of NADP+ is indicated in black frame.

FIG. 7: Structures of the 7α-HSDH/NADP+ complex (picture A) and 7α-HSDH A37D/NAD (picture B), modelled with SWISS-PROT using fabG from *B. anthracis* (PDB: 4JRO) as a template. The protein backbone is coloured by secondary structure elements: α-helices in red, β-sheets yellow and single strands in green. The atoms are coloured according to type: oxygen red, nitrogen blue, carbon grey and phosphorus orange.

SPECIAL EMBODIMENTS OF THE INVENTION

Figure 2:
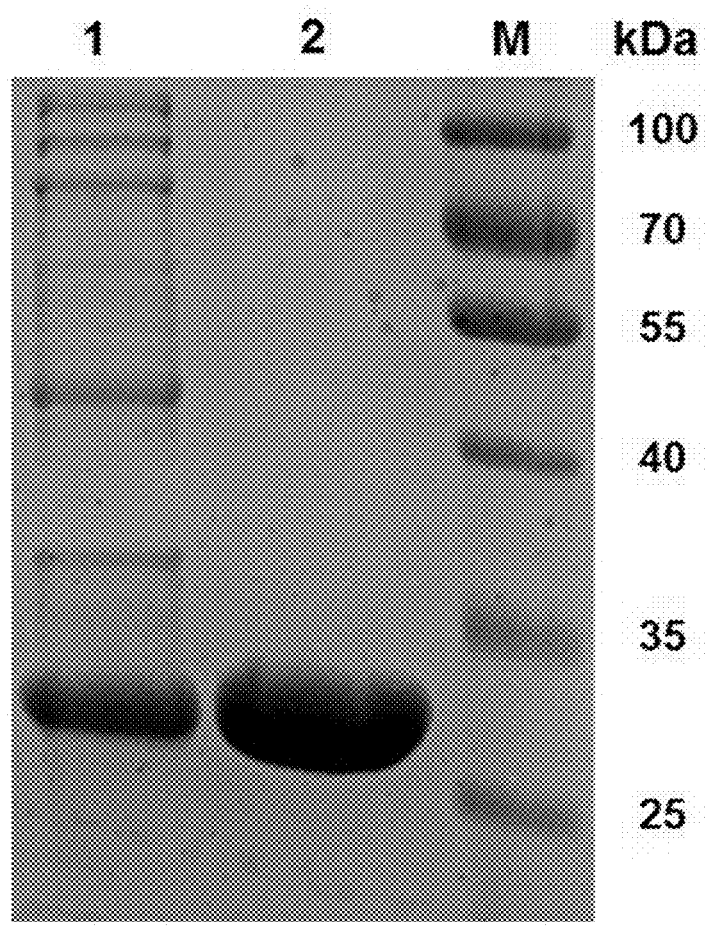
FIG. 2: SDS-PAGE analysis of the heterologous expression and purification of 7α-hydroxysteroid dehydrogenase from *C. difficile*. 10 µg protein was applied onto SDS-PAGE gel. Lane M, molecular weight marker, lane 1 crude extract, lane 2 purified Cd7α-HSDH.

The invention relates in particular to the following special embodiments:
1. A coupled, preferably self-sufficient, biocatalytic process for preparing an UDCA compound of the general Formula (1),

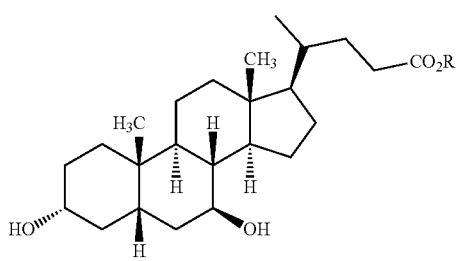

(1)

wherein
R represents alkyl, H an alkali metal ion or $N(R^3)_4^+$ wherein residue $R^3$ are the same or different and represent H or alkyl, or wherein group —$CO_2R$ is replaced by an acid amide group —$CONR^1R^2$, wherein $R^1$ and $R^2$ independently of each other represent an alkyl residue; wherein R preferably represents H;
which method comprises
a) reacting a CDCA compound of general Formula (2)

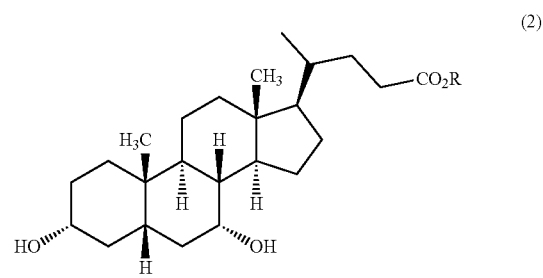

(2)

wherein
R has the same meanings as defined above for group —$CO_2R$ or is replaced by an acid amide group —$CONR_1R_2$,
in the presence of a 7α-HSDH and a 7β-HSDH and, preferably at least a catalytic amount of a cofactor selected from NAD+ and NADP+, wherein said 7α-HSDH and said 7β-HSDH have the ability of utilizing the same cofactor system selected from NAD+/NADH and NADP+/NADPH, and
wherein
a1) said 7α-HSDH catalyzes the oxidation of said CDCA compound of general Formula (2) to the corresponding intermediate 7-KLCA compound of general Formula (3)

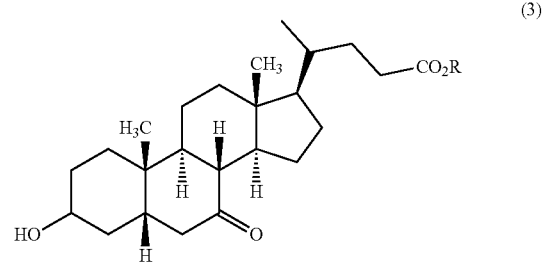

(3)

wherein R is as identified above or wherein group —$CO_2R$ or is replaced by an acid amide group —$CONR_1R_2$ as defined above, and
a2) said 7β-HSDH catalyzes the reduction of said 7-KLCA compound of general Formula (3) as formed in reaction step a1) to said UDCA compound of general Formula (1) and under regeneration of the cofactor consumed in reaction step a1);
and
b) optionally further purifying the reaction product.
2. The process of embodiment 1, wherein step a) is performed in the presence of isolated (purified, enriched or crude, preferably pure) 7α-HSDH enzyme and an isolated (purified, enriched or crude, preferably pure) β-HSDH enzyme or in the presence of one or more recombinant microorganism functionally expressing said enzymes.

3. The process of embodiment 1 or 2, wherein said 7α-HSDH and said 7β-HSDH both utilize the cofactor system NAD⁺/NADH; or wherein said 7α-HSDH and said 7β-HSDH both utilize the cofactor system NADP⁺/NADPH.

4. The process of one of the preceding embodiments wherein said 7α-HSDH and said 7β-HSDH both utilize the cofactor system NAD⁺/NADH; wherein
   a) said 7α-HSDH is selected from
      (1) a 7α-HSDH comprising an amino acid sequence according to SEQ ID NO: 37 which is isolated from *Escherichia coli*, which catalyzes at least the stereospecific enzymatic oxidation of 7α-hydroxysteroids to the corresponding 7-ketosteroids (in particular CDCA to 7-KLCA), and a mutant thereof having at least 80%, as for example 85, 90, 91, 92, 93, 94, 95, 96, 97, 98, 99 or 99.5%, sequence identity to SEQ ID NO: 37 and retaining the ability to utilize NAD⁺/NADH and the ability to catalyze at least the stereospecific enzymatic oxidation of 7α-hydroxysteroids to the corresponding 7-ketosteroids (in particular CDCA to 7-KLCA); and
      (2) a 7α-HSDH which is a mutant of *Clostridium difficile* 7α-HSDH comprising an amino acid sequence according SEQ ID NO: 34, which mutant catalyzes at least the stereospecific enzymatic oxidation of 7α-hydroxysteroids to the corresponding 7-ketosteroids (in particular CDCA to 7-KLCA), under consumption of NAD⁺ as cofactor (i.e. by utilization of the cofactor system NAD⁺/NADH), wherein said 7α-HSDH comprises at least one mutation in a position selected from K16, A37 and R38 of SEQ ID NO: 34 and shows a sequence identity of at least 80%, as for example 85, 90, 91, 92, 93, 94, 95, 96, 97, 98, 99 or 99.5%, to SEQ ID NO:34; which mutants are further defined herein below.
   b) said 7β-HSDH is selected from
      (1) a 7ß-HSDH, which is a mutant of *Collinsella aerofaciens* 7β-HSDH with SEQ ID NO: 54, which mutant catalyzes at least the stereospecific enzymatic reduction of a 7-ketosteroid to the corresponding 7β-hydroxysteroid (in particular 7-KCLA to UDCA) under consumption of NADH as cofactor (i.e. by utilization of the cofactor system NAD⁺/NADH), wherein said 7β-HSDH comprises at least one mutation in a position selected from T17, G39, R40, R41 and K44 of SEQ ID NO: 54 and shows a sequence identity of at least 80%, as for example 85, 90, 91, 92, 93, 94, 95, 96, 97, 98, 99 or 99.5%, to SEQ ID NO:54; which mutants are further defined herein below;

5. The process of one of the embodiments 1 to 3 wherein said 7α-HSDH and said 7β-HSDH both utilize the cofactor system NADP⁺/NADPH, wherein
   a) said 7α-HSDH is selected from
      (1) a 7α-HSDH comprising an amino acid sequence according to SEQ ID NO: 34, which is isolated from *Clostridium difficile*, which catalyzes at least the stereospecific enzymatic oxidation of 7α-hydroxysteroid to the corresponding 7-ketosteroids (in particular CDCA to 7-KLCA), under consumption of NADP⁺ as cofactor (i.e. by utilization of the cofactor system NADP⁺/NADPH), and a mutant thereof having at least 80%, as for example 85, 90, 91, 92, 93, 94, 95, 96, 97, 98, 99 or 99.5%, sequence identity to SEQ ID NO: 34 and retaining the ability to utilize NADP⁺/NADPH and the ability to catalyze at least the stereospecific enzymatic oxidation of 7α-hydroxysteroids to the corresponding 7-ketosteroids;
      (2) a 7α-HSDH which is a mutant of *Escherichia coli* 7α-HSDH with SEQ ID NO: 37 which mutant catalyzes at least the stereospecific enzymatic oxidation of 7α-hydroxysteroids to the corresponding 7-ketosteroids (in particular CDCA to 7-KLCA), under consumption of NADP⁺ as cofactor (i.e. by utilization of the cofactor system NADP⁺/NADPH), wherein said 7α-HSDH comprises at least one mutation in a position selected from D42 and I43 of SEQ ID NO: 37, and shows a sequence identity of at least 80%, as for example 85, 90, 91, 92, 93, 94, 95, 96, 97, 98, 99 or 99.5%, to SEQ ID NO: 37; which mutants are further defined herein below;
   b) said 7β-HSDH is selected from
      (1) a 7ß-HSDH, comprises an amino acid sequence according to SEQ ID NO: 54, and is isolated from *Collinsella aerofaciens* which catalyzes at least the stereospecific enzymatic reduction of a 7-ketosteroid to the corresponding 7ß-hydroxysteroid under consumption of NADPH as cofactor (i.e. by utilization of the cofactor system NADP⁺/NADPH, and a mutant thereof having at least 80%, as for example 85, 90, 91, 92, 93, 94, 95, 96, 97, 98, 99 or 99.5%, sequence identity to SEQ ID NO: 54 and retaining the ability to utilize NADP⁺/NADPH and the ability to catalyze at least the stereospecific enzymatic reduction of a 7-ketosteroid to the corresponding 7ß-hydroxysteroid;
      (2) a 7ß-HSDH, which is a mutant of *Collinsella aerofaciens* 7β-HSDH with SEQ ID NO: 54, which mutant catalyzes at least the stereospecific enzymatic reduction of a 7-ketosteroid to the corresponding 7ß-hydroxysteroid hydroxysteroid (in particular 7-KCLA to UDCA) under consumption of NADPH as cofactor (i.e. by utilization of the cofactor system NADP⁺/NADPH),), wherein said 7ß-HSDH comprises at least one mutation in a position selected from T17, G39, and R64 of SEQ ID NO: 54 and shows a sequence identity of at least 80%, as for example 85, 90, 91, 92, 93, 94, 95, 96, 97, 98, 99 or 99.5%, to SEQ ID NO:54; which mutants are further defined herein below
      (3) a 7ß-HSDH, comprises an amino acid sequence according to SEQ ID NO: 56, and is isolated from Ruminococcus gnavus which catalyzes at least the stereospecific enzymatic reduction of a 7-ketosteroid to the corresponding 7ß-hydroxysteroid hydroxysteroid (in particular 7-KCLA to UDCA) under consumption of NADPH as cofactor (i.e. by utilization of the cofactor system NADP⁺/NADPH, and a mutant thereof having at least 80%, as for example 85, 90, 91, 92, 93, 94, 95, 96, 97, 98, 99 or 99.5%, sequence identity to SEQ ID NO: 56, and retaining the ability to utilize NADP⁺/NADPH and the ability to catalyze at least the stereospecific enzymatic reduction of a 7-ketosteroid to the corresponding 7ß-hydroxysteroid.

6. A 7α-HSDH which is a mutant of *E. coli* 7α-HSDH with SEQ ID NO: 37, which mutant catalyzes at least the stereospecific enzymatic oxidation of 7α-hydroxysteroids to the corresponding 7-ketosteroids (in particular CDCA to 7-KLCA), under consumption of NADP⁺ as cofactor (i.e. by utilization of the cofactor system NADP⁺/NADPH), wherein the enzyme comprises at least one mutation at an amino acid sequence position selected from D42 and I43 of SEQ ID NO: 37 and shows a sequence identity of at least 80%, as for example 85, 90, 91, 92, 93, 94, 95, 96, 97, 98, 99 or 99.5%, to SEQ ID NO:37.

7. The 7α-HSDH of embodiment 6, wherein the amino acid sequence mutation is selected from single or multiple mutations comprising:
   a) D42$X_1$ and/or
   b) I43$X_2$
   wherein $X_1$ represents an amino acid residue different from aspartic acid (D), in particular a proteinogenic amino acid residue, in particular any, the specific activity increasing and/or the substrate inhibition decreasing and/or the cofactor utilization or cofactor specificity modifying, in particular natural amino acid; and $X_2$ represents an amino acid residue different from isoleucine (I), in particular a proteinogenic amino acid residue, in particular any, the specific activity increasing and/or the substrate inhibition decreasing and/or the cofactor utilization or cofactor specificity modifying, in particular natural amino acid.

8. 7α-HSDH according to any one of the preceding embodiments 6 and 7, wherein said mutation is selected from
   a) the single mutations
      D42$X_1$ and
      I43$X_2$ and the
   b) double mutations
      D42$X_1$/I43 $X_2$
   wherein
   $X_1$ represents G, A or V and
   $X_2$ represents R, H or K
   Non-limiting examples of such double mutants are: (D42G/I43R); (D42G/I43H); (D42G/I43K); (D42A/I43R); (D42A/I43H); (D42A/I43K); (D42V/I43R); (D42V/I43H); (D42V/I43K)

9. 7α-HSDH according to any one of the embodiments 6 to 8 which, if compared to 7α-HSDH of SEQ ID NO:37 show the following feature profile:
   a) an increased specific activity (Vmax [U/mg]) for NADP$^+$ during the enzymatic oxidation of CDCA with NADP$^+$ as cofactor;
   wherein the specific activity, if compared to the non-mutated enzyme, is increased by at least 1, 5 or 10%, in particular at least 1-fold, more particularly 2- to 10-fold;
   b) a modified cofactor specificity with regard to NADH and NADPH, as for example a more pronounced specificity for NADP(H), and a reduced, more particularly a diminished or missing specificity for NAD(H)
   c) wherein features a) to b) may be present individually or in any combination.

10. A 7α-HSDH which is isolated from *C. difficile* and has an amino acid sequence according to SEQ ID NO: 34 or a functional variant thereof which shows a sequence identity of at least 80%, as for example 85, 90, 91, 92, 93, 94, 95, 96, 97, 98, 99 or 99.5%, to SEQ ID NO:34; or which is a mutant of *C. difficile* 7α-HSDH with SEQ ID NO: 34, which mutant catalyzes at least the stereospecific enzymatic oxidation of 7α-hydroxysteroids to the corresponding 7-ketosteroids (in particular CDCA to 7-KLCA), under consumption of NAD$^+$ as cofactor (i.e. by utilization of the cofactor system NAD$^+$/NADH), wherein the enzyme mutant comprises a mutation in at least one amino acid position selected from K16, A37 and R38 of SEQ ID NO: 34 and shows a sequence identity of at least 80%, as for example 85, 90, 91, 92, 93, 94, 95, 96, 97, 98, 99 or 99.5%, to SEQ ID NO:34.

11. The 7α-HSDH of embodiment 10 wherein the amino acid sequence mutation is selected from single or multiple mutations comprising:
   a) K16$X_1$
   b) A37$X_2$
   c) R38$X_3$
   wherein $X_1$ represents an amino acid residue different from lysine (K), in particular a proteinogenic amino acid residue, in particular any, the specific activity increasing and/or the substrate inhibition decreasing and/or the cofactor utilization or cofactor specificity modifying, in particular natural amino acid;
   $X_2$ represents an amino acid residue different from alanine (A), in particular a proteinogenic amino acid residue, in particular any, the specific activity increasing and/or the substrate inhibition decreasing and/or the cofactor utilization or cofactor specificity modifying, in particular natural amino acid; and
   $X_3$ represents an amino acid residue different from arginine (R), in particular a proteinogenic amino acid residue, in particular any, the specific activity increasing and/or the substrate inhibition decreasing and/or the cofactor utilization or cofactor specificity modifying, in particular natural amino acid.

12. 7α-HSDH according to any one of the preceding embodiments 10 and 11, wherein said mutation is selected from
   a) the single mutations
      K16$X_1$
      A37$X_2$
      R38$X_3$
      and the
   b) double mutations
      K16$X_1$/A37$X_2$ and
      A37$X_2$/R38$X_3$
   wherein
   $X_1$ represents A, G, or D;
   $X_2$ represents D or E: and
   $X_3$ represents I.
   Non-limiting examples of such double mutants are: (K16A/A37D), (K16A/A37E); (K16G/A37D), (K16G/A37E) (K16D/A37D), (K16D/A37E); (A37D/R38I) and (A37E/R38I).

13. 7α-HSDH according to any one of the embodiments 10 to 12 which, if compared to 7α-HSDH of SEQ ID NO:34 show the following feature profile:
   a) an increased specific activity (Vmax [U/mg]) for CDCA
   wherein the specific activity, if compared to the non-mutated enzyme, is increased by at least 1, 5 or 10%, in particular at least 1-fold, more particularly 2- to 10-fold;
   c) an increased specific activity (Vmax [U/mg]) for NAD$^+$ during the enzymatic oxidation of CDCA with NAD$^+$ as co-factor;
   wherein the specific activity, if compared to the non-mutated enzyme, is increased by at least 1, 5 or 10%, in particular at least 1-fold, more particularly 2- to 10-fold;
   d) a modified co-factor specificity with regard to NAD(H) and NADP(H),
   as for example a more pronounced specificity for NAD (H), and a reduced, more particularly a diminished or missing specificity for NADP(H)
   e) a reduced or preferably essentially missing, more preferably missing, substrate inhibition for at least one bile acid, in particular CA and/or CDCA and/or 7-KLCA, in particular CDCA;
as for example with a Ki-value in the range of >1 mM, as for example in the range of 1 to 200 mM, 2 to 150 mM, 2.5 to 100 mM;
f) wherein features a) to d) may be present individually or in any combination.

14. Nucleotide sequence encoding 7α-HSDH according to any one of the preceding embodiments 6 to 13.

15. Expression cassette, comprising the control of at least one regulative sequence, at least one nucleotide sequence of embodiment 14.

16. Expression vector, comprising at least one expression cassette of embodiment 15.

17. Recombinant microorganism, which carries at least one nucleotide sequence according to embodiment 14 or at least one expression cassette according to embodiment 15 or at least one expression vector according to embodiment 16.

18. The recombinant microorganism according to embodiment 17, which in addition carries the encoding sequence for at least one further enzyme, selected from further hydroxysteroid dehydrogenases (HSDH) suitable for cofactor regeneration.

19. The recombinant microorganism according to embodiment 18, which co-expresses a 7α-HSDH and a 7β-HSDH both utilize the cofactor system NAD$^+$/NADH; or which co-expresses a 7α-HSDH and a 7β-HSDH both utilize the cofactor system NADP$^+$/NADPH.

20. The recombinant microorganism according to embodiment 19, which co-expresses a 7α-HSDH and a 7β-HSDH as defined in one of the embodiments 4 and 5.
Suitable recombinant microorganisms may carry one or more copies of such 7α-HSDH and a 7β-HSDH enzymes as herein defined on one or more expression plasmids. Single plasmid systems or multi-copy plasmid systems are applicable (see WO 2012/080504) As examples there may be mentioned single plasmid systems, like pET21a and multi copy plasmids, like Novagenes Duet-Vectors, like pACYCDuet-1, pETDuet-1, pCDFDuet-1, pRSFDuet-1 and pCOLADuet-1 (see also User Protocol TB340 Rev. E0305 from Novagen).

21. Biocatalytic process for the enzymatic or microbial synthesis of 7α-ketosteroids, wherein the corresponding 7-hydroxysteroid in the presence of a 7α-HSDH mutant according to the definition of one of the embodiments 6 to 13 or in the presence of a recombinant microorganism expressing said 7α-HSDH mutant according to one of the embodiments 17 to 20 is oxidized and optionally one of the formed reaction products is isolated from the reaction mixture.

22. The process of embodiment 21, wherein said 7-hydroxysteroid is selected from
cholic acid (CA)
chenodeoxycholic acid (CDCA),
12-ketochenodeoxycholic acid (12-keto-CDCA) and, preferably by said 7α-HSDH mutant oxidizable, derivatives thereof, in particular a salt, amide or alkyl ester of the acid.

23. The process of embodiment 11 or 12, wherein the oxidation is performed in the presence and in particular under consumption of NAD$^+$ or NADP$^+$.

24. The process of embodiment 23, wherein NAD$^+$ or NADP$^+$ as consumed is regenerated by coupling with an NAD$^+$ or NADP$^+$-regenerating enzyme, wherein said enzyme is selected from 7β-HSDHs, alcohol dehydrogenases (ADH) and formiate dehydrogenases (FDH), glucose dehydrogenase (GDH), NADH-dehydrogenases, alcohol dehydrogenases (ADH), glucose-6-phosphate-dehydrogenases (G6PDH), phosphite dehydrogenases (PtDH).

Any reference to a specific amino acid sequence herein above (like SEQ ID NO: 34, 37 40, 44, 47, 50, 54 and 56), also relates, unless otherwise stated, to any N-terminally or C-terminally extended variant thereof, like in particular variants extended by a His-tag sequence, in particular hexa-His tag sequence.

Non-limiting examples of such His-tag variants are those of SEQ ID NO: 35, 38, 41, 42, 45, 48, 51 and 52.

FURTHER ASPECTS AND EMBODIMENTS OF THE INVENTION

1. General Definitions and Abbreviations Used

The term "self-sufficient" designates a coupled enzymatic redox reaction wherein the cofactor which is consumed by a first partial reduction reaction or oxidation reaction is essentially completely regenerated by a second partial oxidation reaction or reduction reaction, respectively.

Unless stated otherwise, the term "7β-HSDH" denotes a dehydrogenase enzyme, which catalyzes at least the stereo-specific and/or regiospecific reduction of DHCA or 7,12-diketo-3α-CA (7,12-diketo-LCA) to 3,12-diketo-7β-CA or 12-keto-UDCA, in particular with stoichiometric consumption of NAD(P)H and optionally the corresponding reverse reaction. A "7β-HSDH" also catalyses the reduction of 7-ketolithocholic acid (7-KLCA) to UDCA, and optionally the corresponding reverse reaction. The enzyme can be a native or recombinantly produced enzyme, it may be the wild type enzyme or genetically modified by suitable mutations or by C- and/or N-terminal amino acid sequence extensions, like His-tag containing sequences. The enzyme can basically be mixed with cellular, for example protein impurities, but preferably is in pure form. Suitable methods of detection are described for example in the experimental section given below or are known from the literature (e.g. *Characterization of NADP-dependent 7 beta-hydroxysteroid dehydrogenases from Peptostreptococcus productus and Eubacterium aerofaciens*. S Hirano and N Masuda. Appl Environ Microbiol. 1982). Enzymes with this activity are classified under the EC number 1.1.1.201.

Unless stated otherwise, the term "7α-HSDH" denotes a dehydrogenase enzyme, which catalyses at least the stereo-specific and/or regiospecific oxidation of CDCA to 7-KLCA) in particular with stoichiometric consumption of NAD(P)$^+$, and optionally the corresponding reverse reaction. The enzyme can be a native or recombinantly produced enzyme, it may be the wild type enzyme or genetically modified by suitable mutations or by C- and/or N-terminal amino acid sequence extensions, like His-tag containing sequences. The enzyme can basically be mixed with cellular, for example protein impurities, but preferably is in pure form. Suitable methods of detection are described for example in the experimental section given Enzymes with this activity are classified under the EC number 1.1.1.159.

A "pure form" or a "pure" or "substantially pure" enzyme is to be understood according to the invention as an enzyme with a degree of purity above 80, preferably above 90, especially above 95, and quite particularly above 99 wt %, relative to the total protein content, determined by means of usual methods of detecting proteins, for example the biuret method or protein detection according to Lowry et al. (cf.

description in R. K. Scopes, Protein Purification, Springer Verlag, New York, Heidelberg, Berlin (1982)).

A "redox equivalent" means a low-molecular organic compound usable as electron donor or electron acceptor, for example nicotinamide derivatives such as $NAD^+$ and $NADH^+$ or their reduced forms NADH and NADPH respectively. "Redox equivalent" and "cofactor" are used as synonyms in the context of the present invention. Thus, a "cofactor" in the sense of the invention can also be described as "redox-capable cofactor", i.e. as a cofactor that can be present in a reduced and an oxidized form.

A "spent" cofactor is to be understood as the reduced or oxidized form of the cofactor, which in the course of a specified reduction or oxidation reaction of a substrate is transformed into the corresponding oxidized or reduced form. By regeneration, the oxidized or reduced cofactor form that is formed in the reaction is converted back to the reduced or oxidized starting form, so that it is available again for the reaction of the substrate.

An "altered cofactor usage" is to be understood in the context of the present invention as a qualitative or quantitative change compared to a reference. In particular, an altered cofactor usage can be observed by undertaking amino acid sequence mutations. This change can then be determined compared to the unmutated starting enzyme. Moreover, the activity with respect to a particular cofactor can be increased or reduced by undertaking a mutation or can be prevented completely. An altered cofactor usage also comprises, however, changes such that instead of a specificity for an individual cofactor, now at least one further second cofactor, different from the first cofactor, is usable (i.e. there is an extended cofactor usage). Conversely, however, a capacity for usage of two different cofactors that was originally present can be altered so that specificity is only increased for one of these cofactors or only reduced for one of these cofactors or is completely eliminated. For example, an enzyme that is dependent on the cofactor NAD (NADH) can now, owing to a change of the cofactor usage, be dependent both on NAD (NADH) and the cofactor NADP (NADPH) or the original dependence on NAD (NADH) can be completely transformed to a dependence on NADP (NADPH) and vice versa.

The terms "$NAD^+$/NADH dependence" or "$NADP^+$/NADPH dependence", unless stated otherwise, are to be interpreted widely according to the invention. These terms comprise both and preferably "specific" dependences, i.e. exclusively dependence on $NAD^+$/NADH or $NADP^+$/NADPH, as well as, less preferably, the dependence of the enzymes used according to the invention on both cofactors, i.e. dependence on $NAD^+$/NADH and $NADP^+$/NADPH.

This applies correspondingly to the terms "$NAD^+$/NADH-accepting" or "$NADP^+$/NADPH-accepting".

The terms "$NAD^+$/NADH-regenerating" or "$NADP^+$/NADPH-regenerating", unless stated otherwise, are to be interpreted widely according to the invention. These terms comprise both, preferably, "specific" i.e. exclusive capacity for regenerating spent cofactor $NAD^+$/NADH or $NADP^+$/NADPH, and, less preferably, the capacity for regenerating both cofactors, i.e. $NAD^+$/NADH and $NADP^+$/NADPH.

"Proteinogenic" amino acids comprise in particular (single-letter code): G, A, V, L, I, F, P, M, W, S, T, C, Y, N, Q, D, E, K, R and H.

"Immobilization" means, according to the invention, the covalent or noncovalent binding of a biocatalyst used according to the invention, for example a 7β-HSDH on a solid, i.e. essentially insoluble in the surrounding liquid medium, carrier material. According to the invention, whole cells, such as the recombinant microorganisms used according to the invention, can correspondingly also be immobilized by means of such carriers.

A "substrate inhibition reduced in comparison with the non-mutated enzyme" means that the substrate inhibition observed with the non-mutated enzyme for a particular substrate is no longer observed, i.e. essentially is no longer measurable, or only occurs at higher substrate concentration, i.e. the $K_i$ value is increased.

"Cholic acid compound" means compounds according to the invention with the carbon skeleton structure, especially the steroid structure of cholic acid and the presence of keto and/or hydroxy or acyloxy groups in ring position 7 and optionally ring positions 3 and/or 12.

A compound of a special type, for example a "cholic acid compound" or an "ursodeoxycholic acid compound" in particular also means derivatives of the underlying starting compound (for example cholic acid or ursodeoxycholic acid).

Said derivatives comprise "salts", for example alkali metal salts such as lithium, sodium and potassium salts of the compounds; and ammonium salts, wherein an ammonium salt comprises the $NH_4^+$ salt or those ammonium salts in which at least one hydrogen atom can be replaced with a $C_1$-$C_6$-alkyl residue. Typical alkyl residues are, in particular, $C_1$-$C_4$-alkyl residues, such as methyl, ethyl, n- or i-propyl-, n-, sec- or tert-butyl, and n-pentyl and n-hexyl and the singly or multiply branched analogs thereof.

"Alkyl esters" of compounds according to the invention are, in particular, lower alkyl esters, for example $C_1$-$C_6$-alkyl esters. As nonlimiting examples, we may mention methyl, ethyl, nor i-propyl, n-, sec- or tert-butyl esters, or longer-chain esters, for example n-pentyl and n-hexyl esters and the singly or multiply branched analogs thereof.

"Amides" are, in particular, reaction products of acids according to the invention with ammonia or primary or secondary monoamines. Such amines are for example mono- or di-$C_1$-$C_6$-alkyl monoamines, wherein the alkyl residues can optionally be further substituted independently of one another, for example with carboxyl, hydroxyl, halogen (such as F, Cl, Br, I), nitro and sulfonate groups.

"Acyl groups" according to the invention are, in particular, nonaromatic groups with 2 to 4 carbon atoms, for example acetyl, propionyl and butyryl, and aromatic groups with an optionally substituted mononuclear aromatic ring, wherein suitable substituents are selected for example from hydroxyl, halogen (such as F, Cl, Br, I), nitro and $C_1$-$C_6$-alkyl groups, for example benzoyl or toluoyl.

The term "biocatalytic process" refers to any process carried out in the presence of catalytic activity of at least one enzyme according to the invention, i.e. processes in the presence of raw, or purified, dissolved, dispersed or immobilized enzyme, or in the presence of whole microbial cells, which have or express such enzyme activity. Biocatalytic processes therefore include both enzymatic and microbial processes.

The term "stereospecific" means that one of several possible stereoisomers of a compound produced according to the invention is produced with at least one asymmetry center by the action of an enzyme according to the invention in high "enantiomeric excess" or high "enantiomeric purity" or "stereoisomeric pure", for example at least 90% ee, in particular at least 95% ee, or at least 98% ee, or at least 99% ee. The ee % value is calculated from the following formula:

$$ee\ \% = [X_A - X_B]/[X_A + X_B] * 100,$$

in which $X_A$ and $X_B$ stand for the mole fraction of enantiomers A and B respectively.

The hydroxysteroid compounds used or prepared according to the invention, for example cholic acid, ursodeoxycholic acid, 12-keto-chenodeoxycholic acid, chenodeoxycholic acid and 7-keto-lithocholic acid, can be used in stereoisomerically pure form or in a mixture with other stereoisomers in the process according to the invention or obtained therefrom. Preferably, however, the compounds used or prepared are used or isolated in substantially stereoisomerically pure form.

The following Table A gives the structural formulas, chemical names and the abbreviations used for chemical compounds of relevance for the present technical field:

TABLE A

| Formula | Abbreviation | Chemical name |
|---|---|---|
| 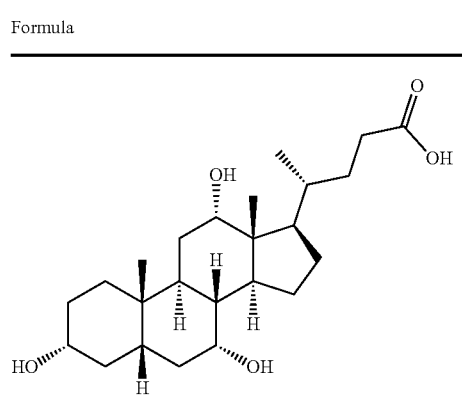<br>Cholic acid | CA | Cholic acid |
| 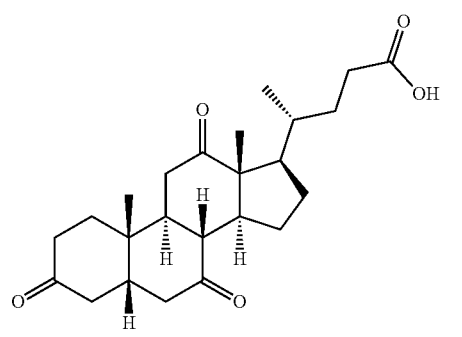<br>Dehydrocholic acid | DHCA | Dehyrocholic acid |
| 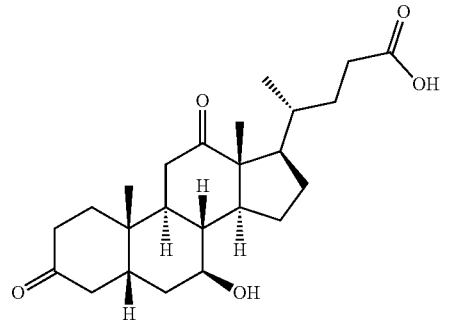<br>3, 12-Diketo-7β-cholanic acid | 3, 12-diketo-7β-CA | 3, 12-Diketo-7β-cholanic acid |

TABLE A-continued
| Formula | Abbreviation | Chemical name |
|---|---|---|
| 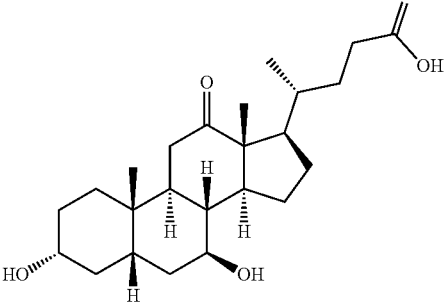<br>12Keto-ursodeoxycholic acid | 12Keto-UDCA | 12Keto-ursodeoxycholic acid |
| 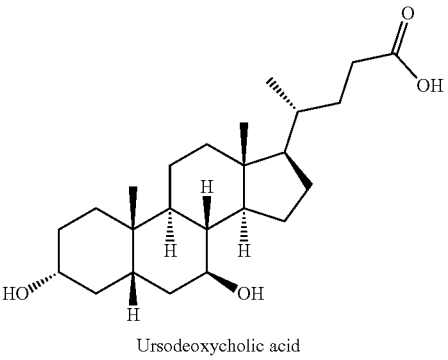<br>Ursodeoxycholic acid | UDCA | Ursodeoxycholic acid |
| 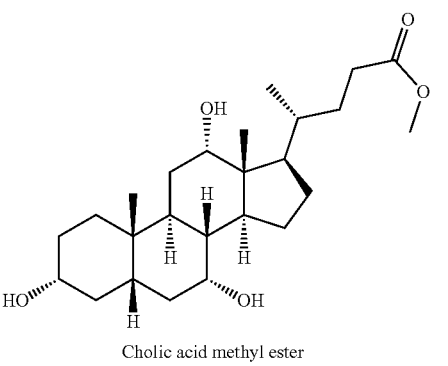<br>Cholic acid methyl ester | CA methyl ester | Cholic acid methyl ester |
| 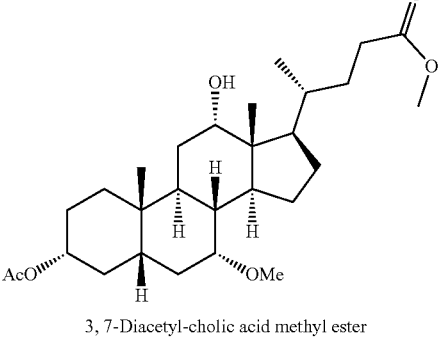<br>3, 7-Diacetyl-cholic acid methyl ester | 3, 7-diacetyl-CA-methyl ester | 3, 7-Diacetyl-cholic acid methyl ester* |

TABLE A-continued

| Formula | Abbreviation | Chemical name |
| --- | --- | --- |
| 12-Keto-3,7-diacetyl cholanic acid methyl ester | 12-keto-3, 7-diacetyl-CA methyl ester | 12-Keto-3, 7-diacetyl cholanic acid methyl ester* |
| Chenodeoxycholic acid | CDCA | Chenodeoxycholic acid |
| 7-Keto-lithocholic acid | 7-Keto-LCA | 7-Keto-lithocholic acid |
| 7, 12-Diketo-lithocholic acid | 7, 12-Diketo-LCA | 7, 12-Diketo-lithocholic acid |

TABLE A-continued

| Formula | Abbreviation | Chemical name |
|---|---|---|
| 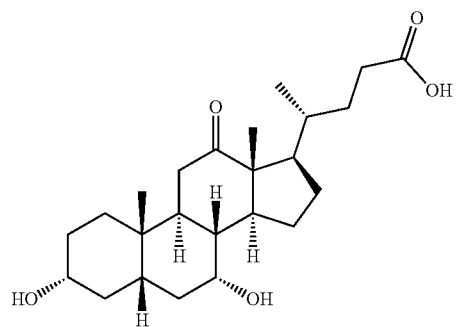 12-Keto-chenodeoxycholic acid | 12-Keto-CDCA | 12-Keto-chenodeoxycholic acid |

2. Proteins or Enzymes

2.1 General

The present invention is not limited to the concretely disclosed proteins or enzymes with 7β-HSDH or 7α-HSDH activity (like SEQ ID NO: 34, 37 40, 44, 47, 54 and 56) or mutants thereof, but rather also extends to functional equivalents thereof.

"Functional equivalents" or analogues of the concretely disclosed enzymes are, in the context of the present invention, polypeptides that are different from them, but still possess the desired biological activity, for example 7β HSDH or 7α-HSDH activity.

For example, "functional equivalents" are to be understood as enzymes that have, in the test used for 7β-HSDH or 7α-HSDH activity, an activity that is higher or lower by at least 1%, e.g. at least 10% or 20%, e.g. at least 50% or 75% or 90% than that of a starting enzyme, comprising an amino acid sequence defined herein.

Functional equivalents are in addition preferably stable in the pH range from 4 to 11 and advantageously possess an optimal pH in a pH range from 6 to 10, such as in particular 8.5 to 9.5, and an optimal temperature in the range from 15° C. to 80° C. or 20° C. to 70° C., for example about 45 to 60° C. or about 50 to 55° C.

The 7β-HSDH activity can be detected using various known tests. Without being restricted to this, we may mention a test using a reference substrate, e.g. CA or DHCA or 7-KLCA, under standardized conditions, as defined in the cross-referenced prior art patent literature or as described in the experimental section.

Tests for determining 7α-HSDH activity are also known per se. Without being restricted to this, we may mention a test using a reference substrate, e.g. CDCA under standardized conditions, as defined in the experimental section.

"Functional equivalents" according to the invention also means, in particular, "mutants", which have in at least one sequence position of the aforementioned amino acid sequences an amino acid other than that concretely stated, but nevertheless possess one of the aforementioned biological activities. "Functional equivalents" therefore comprise the mutants obtainable by one or more, for example 1, 2, 3, 4, 5, 6, 7, 8, 9, 10, 11, 12, 13, 14 or 15, amino acid additions, substitutions, deletions and/or inversions, wherein the stated changes can occur in any sequence position, provided they lead to a mutant with the property profile according to the invention. Functional equivalence in particular also obtains when the patterns of reactivity between mutant and unaltered polypeptide coincide qualitatively, i.e. for example the same substrates are converted at different rates. Examples of suitable amino acid substitutions are presented in the following table:

| Original residue | Examples of substitution |
|---|---|
| Ala | Ser |
| Arg | Lys |
| Asn | Gln; His |
| Asp | Glu |
| Cys | Ser |
| Gln | Asn |
| Glu | Asp |
| Gly | Pro |
| His | Asn; Gln |
| Ile | Leu; Val |
| Leu | Ile; Val |
| Lys | Arg; Gln; Glu |
| Met | Leu; Ile |
| Phe | Met; Leu; Tyr |
| Ser | Thr |
| Thr | Ser |
| Trp | Tyr |
| Tyr | Trp; Phe |
| Val | Ile; Leu |

"Functional equivalents" in the above sense are also "precursors" of the polypeptides described and "functional derivatives" and "salts" of the polypeptides.

"Precursors" are natural or synthetic precursors of the polypeptides with or without the desired biological activity.

The expression "salts" means both salts of carboxyl groups and acid addition salts of amino groups of the protein molecules according to the invention. Salts of carboxyl groups can be prepared in a manner known per se and comprise inorganic salts, for example sodium, calcium, ammonium, iron and zinc salts, and salts with organic bases, for example amines, such as triethanolamine, arginine, lysine, piperidine and the like. Acid addition salts, for example salts with mineral acids, such as hydrochloric acid or sulfuric acid and salts with organic acids, such as acetic acid and oxalic acid, are also an object of the invention.

"Functional derivatives" of polypeptides according to the invention can also be prepared on functional amino acid side groups or on their N- or C-terminal end using known techniques. Such derivatives comprise for example aliphatic esters of carboxylic acid groups, amides of carboxylic acid groups, obtainable by reaction with ammonia or with a primary or secondary amine; N-acyl derivatives of free amino groups, prepared by reaction with acyl groups; or O-acyl derivatives of free hydroxyl groups, prepared by reaction with acyl groups.

"Functional equivalents" naturally also comprise polypeptides that are obtainable from other organisms, and naturally occurring variants. For example, by sequence comparison, homologous sequence regions can be found and equivalent enzymes can be determined based on the concrete instructions of the invention.

"Functional equivalents" also comprise fragments, preferably individual domains or sequence motifs, of the polypeptides according to the invention, which for example have the desired biological function.

"Functional equivalents" are in addition fusion proteins that have one of the aforementioned polypeptide sequences or functional equivalents derived therefrom and at least one further, functionally different therefrom, heterologous sequence in functional N- or C-terminal linkage (i.e. without mutual substantial functional impairment of the fusion protein parts). Nonlimiting examples of said heterologous sequences are e.g. signal peptides, histidine anchors, like His-tags or enzymes.

"Functional equivalents" that are also included according to the invention are homologs of the concretely disclosed proteins. These possess at least 60%, preferably at least 75%, especially at least 85%, for example 90, 91, 92, 93, 94, 95, 96, 97, 98 or 99%, homology (or sequence identity) to one of the concretely disclosed amino acid sequences, calculated according to the algorithm of Pearson and Lipman, Proc. Natl. Acad. Sci. (USA) 85(8), 1988, 2444-2448. A percentage homology or identity of a homologous polypeptide according to the invention means, in particular, percentage identity of the amino acid residues relative to the total length of one of the amino acid sequences concretely described herein.

The percentage identity values can also be determined on the basis of BLAST alignments, the blastp (protein-protein BLAST) algorithm, or using the Clustal settings given below.

In the case of a possible protein glycosylation, "functional equivalents" according to the invention comprise proteins of the type designated above in deglycosylated or glycosylated form and modified forms obtainable by altering the glycosylation pattern.

Homologs of the proteins or polypeptides according to the invention can be produced by mutagenesis, e.g. by point mutation, lengthening or shortening of the protein.

Homologs of the proteins according to the invention can be identified by screening combinatorial libraries of mutants, for example shortened mutants. For example, a variegated database of protein variants can be produced by combinatorial mutagenesis at the nucleic acid level, for example by enzymatic ligation of a mixture of synthetic oligonucleotides. There are a great many methods that can be used for preparing libraries of potential homologs from a degenerated oligonucleotide sequence. The chemical synthesis of a degenerated gene sequence can be carried out in an automatic DNA synthesizer, and the synthetic gene can then be ligated into a suitable expression vector. The use of a degenerated set of genes makes it possible to provide all sequences in one mixture, which encode the desired set of potential protein sequences. Methods of synthesis of degenerated oligonucleotides are known by a person skilled in the art (e.g. Narang, S. A. (1983) Tetrahedron 39: 3; Itakura et al. (1984) Annu. Rev. Biochem. 53: 323; Itakura et al., (1984) Science 198: 1056; Ike et al. (1983) Nucleic Acids Res. 11: 477).

Several techniques are known in the prior art for screening gene products of combinatorial libraries, that have been produced by point mutations or shortening, and for screening cDNA libraries for gene products with a selected property. These techniques can be adapted to the rapid screening of gene banks that have been produced by combinatorial mutagenesis of homologs according to the invention. The techniques used most often for screening large gene banks, which are based on a high-throughput analysis, comprise cloning the gene bank into replicable expression vectors, transforming suitable cells with the resultant vector bank and expressing the combinatorial genes under conditions in which detection of the desired activity facilitates the isolation of the vector that encodes the gene whose product was detected. Recursive ensemble mutagenesis (REM), a technique that increases the frequency of functional mutants in the banks, can be used in combination with the screening tests, in order to identify homologs (Arkin and Yourvan (1992) PNAS 89: 7811-7815; Delgrave et al. (1993) Protein Engineering 6(3): 327-331).

2.2 Particular 7β-HSDH Enzymes 2.2.1 Wildtype *Collinsella aerofaciens* 7β-HSDH and Functional Equivalents The invention further comprises the use of the 7β-HSDH wild type from *Collinsella aerofaciens* ATCC 25986, as described in the applicant's international patent application WO2011/064404, which is expressly referred to hereby.

This 7β-HSDH obtainable from *Collinsella aerofaciens* DSM 3979 is in particular characterized by at least one other of the following properties, for example 2, 3, 4, 5, 6 or 7 or all such properties:

a) molecular weight (SDS-gel electrophoresis): about 28-32 kDa, especially about 29 to 31 kDa or about 30 kDa;

b) molecular weight (gel filtration, in nondenaturing conditions, such as in particular without SDS): about 53 to 60 kDa, especially about 55 to 57 kDa, such as 56.1 kDa. This proves the dimeric nature of the 7β-HSDH from *Collinsella aerofaciens* DSM 3979;

c) stereoselective reduction of the 7-carbonyl group of 7-keto-LCA to a 7β-hydroxyl group;

d) optimal pH for the oxidation of UDCA in the range from pH 8.5 to 10.5, especially 9 to 10;

e) optimal pH for the reduction of DHCA and 7-keto-LCA in the range from pH 3.5 to 6.5, especially at pH 4 to 6;

f) at least one kinetic parameter from the following table for at least one of the substrates/cofactors mentioned there; in the range of ±20%, especially ±10%, ±5%, ±3%, ±2% or ±1% around the value stated concretely in each case in the following table.

|  | $K_M$ (µM) | $V_{max}$ (U/ mg protein)[b] | $k_{cat}$ (1 µmol/ (µmol × min)) |
| --- | --- | --- | --- |
| NADP+ | 5.32 | 30.58 | 944.95 |
| NADPH | 4.50 | 33.44 | 1033.44 |
| UDCA | 6.23 | 38.17 | 1179.39 |
| 7-Keto-LCA | 5.20 | 30.77 | 950.77 |
| DHCA | 9.23 | 28.33 | 875.35 |
| NAD+ | —[a] | — | Traces |
| NADH | — | — | Traces |

[a] could not be determined, owing to the very low activity
[b] 1 U = 1 µmol/min g) phylogenetic sequence similarity of the prokaryotic 7β-HSDH from *Collinsella aerofadens* DSM 3979, related to the animal 11β-HSDH subgroup, comprising *Cavia porcellus*, *Homo sapiens* and *Mus musculus*.

For example, this 7β-HSDH shows the following properties or combinations of properties: a); b); a) and b); a) and/or b) and c); a) and/or b) and c) and d); a) and/or b) and c) and d) and e); a) and/or b) and c) and d) and e) and f).

A 7β-HSDH of this kind or a functional equivalent derived therefrom is moreover characterized by
a) the stereospecific reduction of a 7-ketosteroid to the corresponding 7(3-hydroxysteroid, and/or
b) the regiospecific hydroxylation of a ketosteroid comprising a keto group in 7-position and at least one further keto group on the steroid skeleton to the corresponding 7β-hydroxysteroid, such as in particular catalyzed by dehydrocholic acid (DHCA) in 7-position to the corresponding 3,12-diketo-7β-cholanic acid, and e.g. is NADPH-dependent.

Said 7β-HSDH has in particular an amino acid sequence according to SEQ ID NO:54 (accession No.: ZP_01773061) or a sequence derived therefrom with a degree of identity of at least 60%, e.g. at least 65, 70, 75, 80, 85, or 90, e.g. at least 91, 92, 93, 94, 95, 96, 97, 98, 99 or 99.5% to this sequence; optionally additionally characterized by one of the following properties or combinations of properties: a); b); a) and b); a) and/or b) and c); a) and/or b) and c) and d); a) and/or b) and c) and d) and e); a) and/or b) and c) and d) and e) and f) according to the above definition.

2.2.2 Particular *Collinsella aerofaciens* 7β-HSDH Mutants

The invention further comprises the use of mutants of the 7β-HSDH wild type from *Collinsella aerofaciens* ATCC 25986, as described in WO2012/080504, WO2015/197698 and WO2016/016213, which is expressly referred to hereby.

3. Nucleic acids and constructs 3.1 Nucleic Acids

The invention also relates to nucleic acid sequences that code for an enzyme with 7β-HSDH or 7α-HSDH activity and the mutants thereof.

The present invention also relates to nucleic acids with a specified degree of identity to the concrete sequences described herein.

"Identity" between two nucleic acids means the identity of the nucleotides over the total nucleic acid length in each case, especially the identity that is calculated by comparison by means of the Vector NTI Suite 7.1 software of the company Informax (USA) employing the Clustal method (Higgins D G, Sharp P M. Fast and sensitive multiple sequence alignments on a microcomputer. Comput Appl Biosci. 1989 April; 5(2): 151-1) setting the following parameters:

Multiple Alignment Parameters:

| | |
|---|---|
| Gap opening penalty | 10 |
| Gap extension penalty | 10 |
| Gap separation penalty range | 8 |
| Gap separation penalty | off |
| % identity for alignment delay | 40 |
| Residue specific gaps | off |
| Hydrophilic residue gap | off |
| Transition weighting | 0 |

TABLE B

7β-HSDH single and multiple mutants

| Position of Mutations | Type | Preferred Mutations | Cofactor usage |
|---|---|---|---|
| WT | — | none | NADPH |
| T17 | S | T17 F, A, I, or S | NADPH/NADH |
| G39 | S | G39 S, A, D, V, I, L, C, K, Y, F, R, T, P, N, E, Q, H, or W | NADPH/NADH |
| R64 | S | R64 E, D, T, L, S, P, V, K, C, A, G, Q, F, W, I, Y, H or N | NADPH |
| G39/R64 | D | G39S/R64E, G39S/R64D | NADPH |
| G39/R40 | D | G39D/R40F, G39D/R40I, G39D/R40L, G39D/R40W, | NADH |
| G39/R40/R41 | T | G39D/R40F/R41(K, Q, S or R) G39D/R40I/R41N | NADH |
| G39/R40/R41/K44 | Q | G39D/R40F/R41K/K44(G, N or Q) | NADH |
| R40 | S | R40D, E, I, V, L, G or A. | NADH |
| R41 | S | R41N, I, L or V | NADH |
| G39/R40 R40/R41 G39/R41 | D | G39D/R40I, G39D/R40V, G39D/R40L R40D/R41I | NADH |

WT = wild type;
S = singe;
D = double;
T = triple;
Q = quadruple

The above mentioned examples also cover variants C- and/or N-terminally extended, in particular extended by a His-Tag sequence, more particularly by Hexa-His-tag sequences.

Any of the above mutants may additional be mutated in any of the following positions K44, R53, K61, R64.

2.2.3 Further 7β-HSDHs

The invention further comprises the use of the 7β-HSDH wild type from Ruminococcus gnavus and of mutants, in particular NADP⁺ dependent mutants, thereof, as described in Chinese patent Application, published under CN105274070 which is expressly referred to hereby.

Pairwise Alignment Parameters:

| | |
|---|---|
| FAST algorithm | on |
| K-tuple size | 1 |
| Gap penalty | 3 |
| Window size | 5 |
| Number of best diagonals | 5 |

As an alternative, the identity can also be determined according to Chenna, Ramu, Sugawara, Hideaki, Koike, Tadashi, Lopez, Rodrigo, Gibson, Toby J, Higgins, Desmond G, Thompson, Julie D. Multiple sequence alignment with the Clustal series of programs. (2003) Nucleic Acids Res 31 (13): 3497-500, and with the following parameters:

| | |
|---|---|
| DNA gap open penalty | 15.0 |
| DNA gap extension penalty | 6.66 |
| DNA matrix | Identity |
| Protein gap open penalty | 10.0 |
| Protein gap extension penalty | 0.2 |
| Protein matrix | Gonnet |
| Protein/DNA ENDGAP | −1 |
| Protein/DNA GAPDIST | 4 |

All nucleic acid sequences mentioned herein (single- and double-stranded DNA and RNA sequences, for example cDNA and mRNA) can be produced in a manner known per se by chemical synthesis from the nucleotide building blocks, for example by fragment condensation of individual overlapping, complementary nucleic acid building blocks of the double helix. The chemical synthesis of oligonucleotides can be carried out for example in a known manner by the phosphoroamidite method (Voet, Voet, 2nd edition, Wiley Press New York, pages 896-897). The adding on of synthetic oligonucleotides and filling of gaps using the Klenow fragment of DNA polymerase and ligation reactions and general cloning techniques are described in Sambrook et al. (1989), Molecular Cloning: A Laboratory Manual, Cold Spring Harbor Laboratory Press.

The invention also relates to nucleic acid sequences (single- and double-stranded DNA and RNA sequences, for example cDNA and mRNA) coding for one of the above polypeptides and functional equivalents thereof, which are accessible for example using artificial nucleotide analogs.

The invention relates both to isolated nucleic acid molecules, which code for polypeptides or proteins according to the invention or biologically active segments thereof, and to nucleic acid fragments that can be used e.g. as hybridization probes or primers for identification or amplification of coding nucleic acids according to the invention.

The nucleic acid molecules according to the invention can moreover contain untranslated sequences from the 3'- and/or 5'-end of the coding gene region.

The invention further comprises the nucleic acid molecules complementary to the concretely described nucleotide sequences, or a segment thereof.

The nucleotide sequences according to the invention make it possible to produce probes and primers that can be used for identification and/or cloning of homologous sequences in other cell types and organisms. These probes or primers usually comprise a nucleotide sequence region, which hybridizes under "stringent" conditions (see below) to at least about 12, preferably at least about 25, for example about 40, 50 or 75 successive nucleotides of a sense strand of a nucleic acid sequence according to the invention or a corresponding antisense strand.

An "isolated" nucleic acid molecule is separated from other nucleic acid molecules that are present in the natural source of the nucleic acid and can moreover be essentially free from other cellular material or culture medium, when it is produced by recombinant techniques, or free from chemical precursors or other chemicals, when it is synthesized chemically.

A nucleic acid molecule according to the invention can be isolated using standard techniques of molecular biology and the sequence information provided according to the invention. For example, cDNA can be isolated from a suitable cDNA library, using one of the concretely disclosed complete sequences or a segment thereof as hybridization probe and standard hybridization techniques (as described for example in Sambrook, J., Fritsch, E. F. and Maniatis, T. Molecular Cloning: A Laboratory Manual. 2nd ed., Cold Spring Harbor Laboratory, Cold Spring Harbor Laboratory Press, Cold Spring Harbor, N.Y., 1989). Moreover, a nucleic acid molecule, comprising one of the disclosed sequences or a segment thereof, can be isolated by polymerase chain reaction, using the oligonucleotide primers that are prepared on the basis of this sequence. The nucleic acid thus amplified can be cloned into a suitable vector and can be characterized by DNA sequence analysis. The oligonucleotides according to the invention can also be produced by standard synthesis techniques, e.g. with an automatic DNA synthesizer.

Nucleic acid sequences according to the invention or derivatives thereof, homologs or parts of these sequences can be isolated for example with usual hybridization methods or PCR technology from other bacteria, e.g. via genomic or cDNA libraries. These DNA sequences hybridize under standard conditions to the sequences according to the invention.

"Hybridize" means the capacity of a polynucleotide or oligonucleotide for binding to an almost complementary sequence under standard conditions, whereas under these conditions nonspecific bindings do not occur between non-complementary partners. For this, the sequences can be complementary to 90-100%. The property of complementary sequences of being able to bind specifically to one another is utilized for example in Northern or Southern blotting or in primer binding in PCR or RT-PCR.

Advantageously, short oligonucleotides of the conserved regions are used for hybridization. It is also possible, however, to use longer fragments of the nucleic acids according to the invention or the complete sequences for hybridization. These standard conditions vary depending on the nucleic acid used (oligonucleotide, longer fragment or complete sequence) or depending on which type of nucleic acid, DNA or RNA, is used for the hybridization. Thus, for example, the melting points for DNA:DNA hybrids are approx. 10° C. lower than those of DNA:RNA hybrids of the same length.

Standard conditions mean for example, depending on the nucleic acid, temperatures between 42 and 58° C. in an aqueous buffer solution with a concentration between 0.1 and 5×SSC (1×SSC=0.15 M NaCl, 15 mM sodium citrate, pH 7.2) or additionally in the presence of 50% formamide such as for example 42° C. in 5×SSC, 50% formamide. Advantageously the hybridization conditions for DNA:DNA hybrids are 0.1×SSC and temperatures between about 20° C. and 45° C., preferably between about 30° C. and 45° C. For DNA:RNA hybrids the hybridization conditions are advantageously 0.1×SSC and temperatures between about 30° C. and 55° C., preferably between about 45° C. and 55° C. These temperatures stated for the hybridization are for example calculated melting point values for a nucleic acid with a length of approx. 100 nucleotides and a G+C content of 50% in the absence of formamide. The experimental conditions for DNA hybridization are described in relevant genetics textbooks, for example Sambrook et al.,"Molecular Cloning", Cold Spring Harbor Laboratory, 1989, and can be calculated from formulas known by a person skilled in the art for example depending on the length of the nucleic acids, the type of hybrids or the G+C content. A person skilled in the art can find further information on hybridization from the following textbooks: Ausubel et al. (eds), 1985, Current Protocols in Molecular Biology, John Wiley & Sons, New York; Hames and Higgins (eds), 1985, Nucleic Acids Hybridization: A Practical Approach, IRL Press at Oxford University Press, Oxford; Brown (ed), 1991, Essential Molecular Biology: A Practical Approach, IRL Press at Oxford University Press, Oxford.

"Hybridization" can in particular take place under stringent conditions. These hybridization conditions are described for example in Sambrook, J., Fritsch, E. F., Maniatis, T., in: Molecular Cloning (A Laboratory Manual), 2nd edition, Cold Spring Harbor Laboratory Press, 1989, pages 9.31-9.57 or in Current Protocols in Molecular Biology, John Wiley & Sons, N.Y. (1989), 6.3.1-6.3.6.

"Stringent" hybridization conditions are understood in particular as: incubation at 42° C. overnight in a solution consisting of 50% formamide, 5×SSC (750 mM NaCl, 75 mM trisodium citrate), 50 mM sodium phosphate (pH7.6), 5×Denhardt solution, 10% dextran sulfate and 20 g/ml denatured, sheared salmon sperm DNA, followed by a filter washing step with 0.1×SSC at 65° C.

The invention also relates to derivatives of the concretely disclosed or derivable nucleic acid sequences.

Thus, further nucleic acid sequences according to the invention can be derived e.g. from SEQ ID NO: 33, 36, 39, 43, 46, 49, 53 or 55 and differ from them by addition, substitution, insertion or deletion of individual or several nucleotides, but furthermore code for polypeptides with the desired property profile.

The invention also covers those nucleic acid sequences that comprise so-called silent mutations or are altered corresponding to the codon usage of a special original or host organism, compared to a concretely stated sequence, as well as naturally occurring variants, for example splice variants or allele variants, thereof.

The invention also relates to sequences obtainable by conservative nucleotide substitutions (i.e. the amino acid in question is replaced with an amino acid of the same charge, size, polarity and/or solubility).

The invention also relates to the molecules derived by sequence polymorphisms from the concretely disclosed nucleic acids. These genetic polymorphisms can exist between individuals within a population owing to natural variation. These natural variations usually bring about a variance from 1 to 5% in the nucleotide sequence of a gene.

Derivatives of the nucleic acid sequence according to the invention with the sequence SEQ ID NO: 33, 36, 39, 43, 46, 49, 53 or 55 mean for example allele variants that have at least 60% homology at the derived amino acid level, preferably at least 80% homology, quite especially preferably at least 90% homology over the total sequence region (regarding homology at the amino acid level, reference may be made to the above information for the polypeptides). The homologies can advantageously be higher on partial regions of the sequences.

Furthermore, derivatives are also to be understood as homologs of the nucleic acid sequences according to the invention, especially of SEQ ID NO: 33, 36, 39, 43, 46, 49, 53 or 55, for example fungal or bacterial homologs, shortened sequences, single-stranded DNA or RNA of the coding and noncoding DNA sequence. For example, homologs to SEQ ID NO: 33, 36, 39, 43, 46, 49, 53 or 55 possess, at DNA level, a homology of at least 40%, preferably of at least 60%, especially preferably of at least 70%, quite especially preferably of at least 80% over the whole DNA region given in SEQ ID NO: 33, 36, 39, 43, 46, 49, 53 or 55.

In addition, derivatives are to be understood for example as fusions with promoters. The promoters that precede the stated nucleotide sequences can be altered by at least one nucleotide exchange, at least one insertion, inversion and/or deletion, but without the functionality or effectiveness of the promoters being impaired. Moreover, the effectiveness of the promoters can be increased by altering their sequence or they can be exchanged completely with more effective promoters even of organisms of a different species.

Furthermore, methods for producing functional mutants are known by a person skilled in the art.

Depending on the technology used, a person skilled in the art can insert completely random or even more targeted mutations in genes or also noncoding nucleic acid regions (which are for example important for the regulation of expression) and then prepare gene banks. The methods of molecular biology required for this are known by a person skilled in the art and for example are described in Sambrook and Russell, Molecular Cloning. 3rd edition, Cold Spring Harbor Laboratory Press 2001.

Methods for modifying genes and therefore for modifying the protein that these encode have long been familiar to a person skilled in the art, such as for example

- site-directed mutagenesis, giving targeted exchange of individual or several nucleotides of a gene (Trower M K (Publ.) 1996; In vitro mutagenesis protocols. Humana Press, New Jersey),
- saturation mutagenesis, in which a codon for any amino acid can be exchanged or added at any site of a gene (Kegler-Ebo D M, Docktor C M, DiMaio D (1994) Nucleic Acids Res 22: 1593; Barettino D, Feigenbutz M, Valcárel R, Stunnenberg H G (1994) Nucleic Acids Res 22: 541; Bark S (1995) Mol Biotechnol 3: 1),
- the error-prone polymerase chain reaction (error-prone PCR), in which nucleotide sequences are mutated by incorrectly functioning DNA polymerases (Eckert K A, Kunkel T A (1990) Nucleic Acids Res 18: 3739);
- the passaging of genes in mutator strains, in which, for example owing to defective DNA-repair mechanisms, there is an increased mutation rate of nucleotide sequences (Greener A, Callahan M, Jerpseth B (1996) An efficient random mutagenesis technique using an *E. coli* mutator strain. In: Trower M K (Publ.) In vitro mutagenesis protocols. Humana Press, New Jersey), or
- DNA shuffling, in which a pool of closely related genes is formed and digested and the fragments are used as template for a polymerase chain reaction, in which through repeated strand separation and bringing together again, finally mosaic genes of full length are produced (Stemmer WPC (1994) Nature 370: 389; Stemmer WPC (1994) Proc Natl Acad Sci USA 91: 10747).

Using so-called directed evolution (described inter alia in Reetz M T and Jaeger K-E (1999), Topics Curr Chem 200: 31; Zhao H, Moore J C, Volkov A A, Arnold F H (1999), Methods for optimizing industrial enzymes by directed evolution, In: Demain A L, Davies J E (Publ.) Manual of industrial microbiology and biotechnology. American Society for Microbiology), a person skilled in the art can produce functional mutants in a targeted manner and on a large scale. In a first step, firstly gene banks of the respective proteins are produced, for example using the methods given above. The gene banks are expressed in a suitable manner, for example by bacteria or by phage-display systems.

The relevant genes of host organisms that express functional mutants with properties that largely correspond to the desired properties can be submitted to another round of mutation. The steps of mutation and of selection or screening can be repeated iteratively until the functional mutants present have the desired properties to a sufficient degree. With this iterative procedure, a limited number of mutations, for example 1 to 5 mutations, can be performed in steps and assessed and selected for their influence on the relevant enzyme property. The selected mutant can then be submitted to another mutation step in the same way. As a result, the number of individual mutants to be investigated can be reduced significantly.

The results according to the invention provide important information regarding structure and sequence of the enzymes in question, which is necessary for targeted generation of further enzymes with desired modified properties. In particular, so-called "hot spots" can be defined, i.e. sequence segments that are potentially suitable for modifying an enzyme property by introducing targeted mutations.

3.2 Constructs

The invention further relates to expression constructs containing, under the genetic control of regulatory nucleic acid sequences, a nucleic acid sequence coding for at least one polypeptide according to the invention; and vectors, comprising at least one of these expression constructs.

"Expression unit" means, according to the invention, a nucleic acid with expression activity, which comprises a promoter, as defined herein, and, after functional linking with a nucleic acid to be expressed or a gene, regulates the expression, i.e. the transcription and the translation of this nucleic acid or of this gene. Therefore the term "regulatory nucleic acid sequence" is also used in this context. In addition to the promoter, other regulatory elements, for example enhancers, can be present.

"Expression cassette" or "expression construct" means, according to the invention, an expression unit that is functionally linked to the nucleic acid to be expressed or the gene to be expressed. In contrast to an expression unit, an expression cassette therefore comprises not only nucleic acid sequences that regulate transcription and translation, but also the nucleic acid sequences that should be expressed as protein as a result of the transcription and translation.

The terms "expression" or "overexpression" describe, in the context of the invention, the production or increase in the intracellular activity of one or more enzymes in a microorganism, which are encoded by the corresponding DNA. For this, for example a gene can be inserted in an organism, a gene that is present can be replaced with another gene, the copy number of the gene or genes can be increased, a strong promoter can be used or a gene can be used that codes for a corresponding enzyme with a high activity, and these measures can optionally be combined.

Preferably said constructs according to the invention comprise a promoter 5'-upstream of the respective coding sequence and 3'-downstream a terminator sequence and optionally further usual regulatory elements, in each case operatively linked with the coding sequence.

"Promoter", a "nucleic acid with promoter activity" or a "promoter sequence" mean, according to the invention, a nucleic acid, which in functional linkage with a nucleic acid to be transcribed, regulates the transcription of said nucleic acid.

"Functional" or "operational" linkage means in this context for example the sequential arrangement of one of the nucleic acids with promoter activity and a nucleic acid sequence to be transcribed and optionally further regulatory elements, for example nucleic acid sequences that ensure the transcription of nucleic acids, and for example a terminator, in such a way that each of the regulatory elements can fulfil its function in the transcription of the nucleic acid sequence. This does not necessarily require a direct linkage in the chemical sense. Genetic control sequences, for example enhancer sequences, can exert their function on the target sequence even from more remote positions or even from other DNA molecules. Arrangements are preferred in which the nucleic acid sequence to be transcribed is positioned behind the promoter sequence (i.e. at the 3'-end), so that the two sequences are linked together covalently. The distance between the promoter sequence and the nucleic acid sequence that is to undergo transgene expression can be less than 200 base pairs, or less than 100 base pairs or less than 50 base pairs.

In addition to promoters and terminators, examples of other regulatory elements that may be mentioned are targeting sequences, enhancers, polyadenylation signals, selectable markers, amplification signals, replication origins and the like. Suitable regulatory sequences are described for example in Goeddel, Gene Expression Technology: Methods in Enzymology 185, Academic Press, San Diego, Calif. (1990).

Nucleic acid constructs according to the invention comprise, in particular, sequence SEQ ID NO: 33, 36, 39, 43, 46, 49, 53 or 55 or derivatives and homologs thereof, and the nucleic acid sequences that can be derived therefrom, which can advantageously be linked operationally or functionally with one or more regulatory signals for controlling, e.g. increasing, gene expression.

In addition to these regulatory sequences, the natural regulation of these sequences can still be present before the actual structural genes and optionally can have been genetically modified, so that the natural regulation is switched off and expression of the genes is increased. However, the nucleic acid construct can also be of simpler construction, i.e. no additional regulatory signals have been inserted before the coding sequence and the natural promoter with its regulation has not been removed. Instead, the natural regulatory sequence is mutated so that regulation no longer occurs and gene expression is increased.

A preferred nucleic acid construct advantageously also contains one or more of the aforementioned "enhancer" sequences, functionally linked to the promoter, which make increased expression of the nucleic acid sequence possible. Additional advantageous sequences can also be inserted at the 3'-end of the DNA sequences, such as further regulatory elements or terminators. The construct can contain one or more copies of the nucleic acids according to the invention. The construct can also contain further markers, such as antibiotic resistances or auxotrophic complementation genes, optionally for selection of the construct.

Examples of suitable regulatory sequences are contained in promoters such as cos, tac, trp, tet, trp-tet, Ipp, lac, lpp-lac, lacI$^{q-}$, T7, T5, T3, gal, trc, ara, rhaP (rhaP$_{BAD}$)SP6, lambda-P$_R$ or in the lambda-P$_L$ promoter, which advantageously find application in Gram-negative bacteria. Further advantageous regulatory sequences are contained for example in the Gram-positive promoters amy and SPO2, in the yeast or fungus promoters ADC1, MFalpha, AC, P-60, CYC1, GAPDH, TEF, rp28, ADH. Artificial promoters can also be used for regulation.

For expression in a host organism, the nucleic acid construct is advantageously inserted into a vector, for example a plasmid or a phage, which makes optimal expression of the genes in the host possible. Apart from plasmids and phages, vectors are also to be understood as all other vectors known by a person skilled in the art, e.g. viruses, such as SV40, CMV, baculovirus and adenovirus, transposons, IS elements, phasmids, cosmids, and linear or circular DNA. These vectors can be replicated autonomously in the host organism or can be replicated chromosomally. These vectors represent another configuration of the invention.

Suitable plasmids are for example pLG338, pACYC184, pBR322, pUC18, pUC19, pKC30, pRep4, pHS1, pKK223-3, pDHE19.2, pHS2, pPLc236, pMBL24, pLG200, pUR290, pIN-III[113]-B1, λgt11 or pBdCl in *E. coli*, pIJ101, pIJ364, pIJ702 or pIJ361 in *Streptomyces*, pUB110, pC194 or pBD214 in *Bacillus*, pSA77 or pAJ667 in *Corynebacterium*, pALS1, plL2 or pBB116 in fungi, 2alphaM, pAG-1, YEp6, YEp13 or pEMBLYe23 in yeasts or pLGV23, pGHlac+, pBIN19, pAK2004 or pDH51 in plants. The aforementioned plasmids represent a small selection of the possible plasmids. Further plasmids are well known by a person skilled in the art and can for example be found in the book Cloning Vectors (eds. Pouwels P. H. et al. Elsevier, Amsterdam-New York-Oxford, 1985, ISBN 0 444 904018).

In another configuration of the vector, the vector containing the nucleic acid construct according to the invention or the nucleic acid according to the invention can also advantageously be inserted in the form of a linear DNA into the microorganisms and can be integrated by heterologous or homologous recombination into the genome of the host organism. This linear DNA can consist of a linearized vector such as a plasmid or only of the nucleic acid construct or the nucleic acid according to the invention.

For optimal expression of heterologous genes in organisms, it is advantageous to modify the nucleic acid sequences according to the specific "codon usage" used in the organism. The "codon usage" can easily be determined on the basis of computer evaluations of other known genes of the organism in question.

An expression cassette according to the invention is prepared by fusion of a suitable promoter with a suitable coding nucleotide sequence and a terminator or polyadenylation signal. For this, usual recombination and cloning techniques are used, such as are described for example in T. Maniatis, E. F. Fritsch and J. Sambrook, Molecular Cloning: A Laboratory Manual, Cold Spring Harbor Laboratory, Cold Spring Harbor, N.Y. (1989) and in T. J. Silhavy, M. L. Berman and L. W. Enquist, Experiments with Gene Fusions, Cold Spring Harbor Laboratory, Cold Spring Harbor, N.Y. (1984) and in Ausubel, F. M. et al., Current Protocols in Molecular Biology, Greene Publishing Assoc. and Wiley Interscience (1987).

For expression in a suitable host organism, the recombinant nucleic acid construct or gene construct is advantageously inserted into a host-specific vector, which makes optimal expression of the genes in the host possible. Vectors are well known by a person skilled in the art and can be found for example in "Cloning Vectors" (Pouwels P. H. et al., Publ., Elsevier, Amsterdam-New York-Oxford, 1985).

4. Microorganisms

Depending on context, the term "microorganism" means the starting (wild-type) microorganism or a genetically modified, recombinant microorganism, or both.

Using the vectors according to the invention, recombinant microorganisms can be produced, which for example have been transformed with at least one vector according to the invention and can be used for producing the polypeptides according to the invention. Advantageously, the recombinant constructs according to the invention described above are introduced into a suitable host system and expressed. Preferably, common cloning and transfection methods known by a person skilled in the art are used, for example coprecipitation, protoplast fusion, electroporation, retroviral transfection and the like, to bring about expression of the stated nucleic acids in the respective expression system. Suitable systems are described for example in Current Protocols in Molecular Biology, F. Ausubel et al., Publ., Wiley Interscience, New York 1997, or Sambrook et al. Molecular Cloning: A Laboratory Manual. 2nd ed., Cold Spring Harbor Laboratory, Cold Spring Harbor Laboratory Press, Cold Spring Harbor, N.Y., 1989. A review of bacterial expression systems for the heterologous expression of proteins is also provided for example by Terpe, K. Appl. Microbiol. Biotechnol. (2006) 72: 211-222.

In principle, all prokaryotic or eukaryotic organisms may come into consideration as recombinant host organisms for the nucleic acid according to the invention or the nucleic acid construct. Advantageously, microorganisms such as bacteria, fungi or yeasts are used as host organisms. Advantageously, Gram-positive or Gram-negative bacteria are used, preferably bacteria of the families Enterobacteriaceae, Pseudomonadaceae, Rhizobiaceae, Streptomycetaceae or Nocardiaceae, especially preferably bacteria of the genera *Escherichia, Pseudomonas, Streptomyces, Nocardia, Burkholderia, Salmonella, Agrobacterium, Clostridium* or *Rhodococcus*. The genus and species *Escherichia coli* is quite especially preferred. Further advantageous bacteria can be found, moreover, in the group of alpha-proteobacteria, beta-proteobacteria or gamma-proteobacteria.

The host organism or the host organisms according to the invention preferably contain at least one of the nucleic acid sequences, nucleic acid constructs or vectors described in this invention, which code for an enzyme with 7β-HSDH activity according to the above definition.

The organisms used in the process according to the invention are grown or cultured in a manner known by a person skilled in the art, depending on the host organism. Microorganisms are as a rule grown in a liquid medium, which contains a carbon source generally in the form of sugars, a nitrogen source generally in the form of organic nitrogen sources such as yeast extract or salts such as ammonium sulfate, trace elements such as iron, manganese, magnesium salts and optionally vitamins, at temperatures between 0° C. and 100° C., preferably between 10° C. and 60° C. with oxygen aeration. The pH of the liquid nutrient medium can be maintained at a fixed value, i.e. during growing it may or may not be regulated. Culture can be batchwise, semi-batchwise or continuous. Nutrients can be supplied at the start of fermentation or can be replenished semi-continuously or continuously.

5. Recombinant Production of the Enzymes and Mutants

The invention further relates to processes for recombinant production of polypeptides according to the invention or functional, biologically active fragments thereof, wherein a polypeptide-producing microorganism is cultured, optionally expression of the polypeptides is induced and the latter are isolated from the culture. The polypeptides can also be produced on an industrial scale in this way, if this is desirable.

The microorganisms produced according to the invention can be cultured continuously or discontinuously in the batch method (batch culture) or in the fed batch or repeated fed batch method. A summary of known cultivation methods can be found in Chmiel's textbook (Bioprozeßtechnik 1. Einführung in die Bioverfahrenstechnik [Bioprocess technology 1. Introduction to bioprocess engineering] (Gustav Fischer Verlag, Stuttgart, 1991)) or in the textbook by Storhas (Bioreaktoren and periphere Einrichtungen [Bioreactors and peripheral equipment]) (Vieweg Verlag, Brunswick/Wiesbaden, 1994)).

The culture medium to be used must suitably fulfill the requirements of the respective strains. Descriptions of culture media for various microorganisms are given in the manual "Manual of Methods for General Bacteriology" of the American Society for Bacteriology (Washington D.C., USA, 1981).

These media usable according to the invention usually comprise one or more carbon sources, nitrogen sources, inorganic salts, vitamins and/or trace elements.

Preferred carbon sources are sugars, such as mono-, di- or polysaccharides. Very good carbon sources are for example glucose, fructose, mannose, galactose, ribose, sorbose, ribulose, lactose, maltose, sucrose, raffinose, starch or cellulose. Sugars can also be added to the media via complex compounds, such as molasses, or other by-products of sugar refining. It may also be advantageous to add mixtures of various carbon sources. Other possible carbon sources are oils and fats such as soybean oil, sunflower oil, peanut oil and coconut oil, fatty acids such as palmitic acid, stearic acid or linoleic acid, alcohols such as glycerol, methanol or ethanol and organic acids such as acetic acid or lactic acid.

Nitrogen sources are usually organic or inorganic nitrogen compounds or materials that contain these compounds. Examples of nitrogen sources comprise ammonia gas or ammonium salts, such as ammonium sulfate, ammonium chloride, ammonium phosphate, ammonium carbonate or ammonium nitrate, nitrates, urea, amino acids or complex nitrogen sources, such as corn-steep liquor, soybean flour, soybean protein, yeast extract, meat extract and others. The nitrogen sources can be used individually or as a mixture.

Inorganic salt compounds that can be contained in the media comprise the chloride, phosphorus or sulfate salts of calcium, magnesium, sodium, cobalt, molybdenum, potassium, manganese, zinc, copper and iron.

The sulfur source used can be inorganic sulfur compounds such as sulfates, sulfites, dithionites, tetrathionates, thiosulfates, sulfides but also organic sulfur compounds, such as mercaptans and thiols.

The phosphorus source used can be phosphoric acid, potassium dihydrogen phosphate or dipotassium hydrogen phosphate or the corresponding sodium-containing salts.

Chelating agents can be added to the medium in order to keep the metal ions in solution. Especially suitable chelating agents comprise dihydroxyphenols, such as catechol or protocatechuate, or organic acids, such as citric acid.

The fermentation media used according to the invention usually also contain other growth factors, such as vitamins or growth promoters, which include for example biotin, riboflavin, thiamine, folic acid, nicotinic acid, panthothenate and pyridoxine. Growth factors and salts are often derived from complex components of the media, such as yeast extract, molasses, corn-steep liquor and the like. Moreover, suitable precursors can be added to the culture medium. The exact composition of compounds in the medium is strongly dependent on the particular experiment and is decided individually for each specific case. Information on media optimization can be found in the textbook "Applied Microbiol. Physiology, A Practical Approach" (Publ. P. M. Rhodes, P. F. Stanbury, IRL Press (1997) p. 53-73, ISBN 0 19 963577 3). Growth media can also be obtained from commercial suppliers, such as Standard 1 (Merck) or BHI (brain heart infusion, DIFCO) and the like.

All components of the media are sterilized, either with heat (20 min at 1.5 bar and 121° C.) or by sterile filtration. The components can either be sterilized together or separately if necessary. All components of the media can be present at the start of culture or can optionally be added continuously or batchwise.

The culture temperature is normally between 15° C. and 45° C., preferably at 25° C. to 40° C. and can be kept constant or varied during the experiment. The pH of the medium should be in the range from 5 to 8.5, preferably around 7.0. The culture pH can be controlled during culture by adding basic compounds such as sodium hydroxide, potassium hydroxide, ammonia or ammonia water or acid compounds such as phosphoric acid or sulfuric acid. To control foaming it is possible to use antifoaming agents, such as fatty acid polyglycol esters. For maintaining the stability of plasmids, suitable selectively acting substances, such as antibiotics, can be added to the medium. To maintain aerobic conditions, oxygen or oxygen-containing gas mixtures, such as ambient air, are fed into the culture. The culture temperature is normally at 20° C. to 45° C. Culture is continued until a maximum of the desired product has formed. This target is normally reached within 10 hours to 160 hours.

The fermentation broth is then processed further. Depending on the requirements, the biomass is removed from the fermentation broth completely or partially by separation techniques, such as centrifugation, filtration, decanting or a combination of these methods or can be left in it completely.

If the polypeptides are not secreted into the culture medium, the cells can also be disrupted and the product can be obtained from the lysate by known methods of protein isolation. The cells can optionally be disrupted with high-frequency ultrasound, by high pressure, for example in a French press, by osmolysis, by the action of detergents, lytic enzymes or organic solvents, using homogenizers or by a combination of several of the methods listed.

The polypeptides can be purified by known chromatographic methods, such as molecular sieve chromatography (gel filtration), such as Q-sepharose chromatography, ion exchange chromatography and hydrophobic chromatography, and with other usual methods such as ultrafiltration, crystallization, salting-out, dialysis and native gel electrophoresis. Suitable methods are described for example in Cooper, F. G., Biochemische Arbeitsmethoden [Methods of Biochemical Processing], Verlag Walter de Gruyter, Berlin, New York or in Scopes, R., Protein Purification, Springer Verlag, New York, Heidelberg, Berlin.

For isolating the recombinant protein, it may be advantageous to use vector systems or oligonucleotides that lengthen the cDNA with defined nucleotide sequences and therefore code for modified polypeptides or fusion proteins, which for example serve for easier purification. Suitable modifications of this kind are for example so-called "tags" functioning as anchors, for example the modification known as hexa-histidine anchors, or epitopes that can be recognized as antigens by antibodies (described for example in Harlow, E. and Lane, D., 1988, Antibodies: A Laboratory Manual. Cold Spring Harbor (N.Y.) Press). These anchors can serve for attaching the proteins to a solid carrier, for example a polymer matrix, which can for example be packed in a chromatography column, or can be used on a microtiter plate or on some other support.

At the same time, these anchors can also be used for recognizing the proteins. For recognition of the proteins, in addition usual markers, such as fluorescent dyes, enzyme markers, which form a detectable reaction product after reaction with a substrate, or radioactive markers, can be used, alone or in combination with the anchors for derivatization of the proteins.

6. Enzyme Immobilization

In the method described herein, the enzymes according to the invention can be used free or immobilized. An immobilized enzyme is to be understood as an enzyme that is fixed to an inert support. Suitable support materials and the enzymes immobilized thereon are known from EP-A-1149849, EP-A-1 069 183 and DE-OS 100193773 and from the literature references cited therein. Regarding this, full reference is made to the disclosure of these documents. Suitable support materials include for example clays, clay minerals, such as kaolinite, diatomaceous earth, perlite, silicon dioxide, aluminum oxide, sodium carbonate, calcium carbonate, cellulose powder, anion exchanger materials, synthetic polymers, such as polystyrene, acrylic resins, phenol-formaldehyde resins, polyurethanes and polyolefins, such as polyethylene and polypropylene. For preparing the supported enzymes, the support materials are usually used in a finelydivided, particulate form, with porous forms being preferred. The particle size of the support material is usually not more than 5 mm, especially not more than 2 mm (particle-size distribution curve). Similarly, when using dehydrogenase as whole-cell catalyst, a free or immobilized form can be selected. Support materials are for example Ca-alginate, and carrageenan. Enzymes as well as cells can also be crosslinked directly with glutaraldehyde (crosslinking to CLEAs). Corresponding and further methods of immobilization are described for example in J. Lalonde and A. Margolin "Immobilization of Enzymes" and in K. Drauz and H. Waldmann, Enzyme Catalysis in Organic Synthesis 2002, Vol. III, 991-1032, Wiley-VCH, Weinheim.

The invention will now be explained in more detail by means of the following, non-limiting examples.

Experimental Part

Unless stated otherwise, the cloning steps carried out in the context of the present invention, for example restriction cleavage, agarose gel electrophoresis, purification of DNA fragments, transfer of nucleic acids onto nitrocellulose and nylon membranes, linkage of DNA fragments, transformation of microorganisms, culturing of microorganisms, multiplication of phages and sequence analysis of recombinant DNA are, if not otherwise sated, carried out by applying well-known techniques, as for example described in Sambrook et al. (1989) op. cit.

Example I: Cloning, Expression, and Biochemical Characterization of a Novel NADP-Dependent 7α-Hydroxysteroid Dehydrogenase from *Clostridium difficile*, Mutants Thereof, in Particular Cofactor Switch Mutants, and their Application for the Oxidation of Bile Acids In this example, a novel 7α-HSDH from *C. difficile* (DSM 12056) was successfully cloned, expressed, purified, and biochemically characterized. Contrary to all known 7α-HSDH this enzyme does not show a substrate inhibition for bile acids. This Cd7α-HSDH was annotated as a putative steroid oxidoreductase and showed 30% homology to the protein sequence of the 7α-HSDH from *E. coli* (NAD$^+$-dependent) (N. Tanaka, T. Nonaka, T. Tanabe, T. Yoshimoto, D. Tsuru, Y. Mitsui, Crystal structures of the binary and ternary complexes of 7α-Hydroxysteroid Dehydrogenase from *Escherichia coli*., J. Am. Chem. Soc. 35 (1996) 7715-30. doi:10.1021/bi951904d) and 55% to the 7α-HSDH from *C. sordellii* (NADP$^+$-dependent) (J. Coleman, L. Hudson, M. Adams, Characterization and regulation of the NADP-linked 7alpha-Hydroxysteroid Dehydrogenase gene from *Clostridium sordellii*., J. Bacteriol. 176 (1994) 4865-74). HPLC-analysis of a bioconversion of 7-KLCA confirmed that the cloned enzyme catalyses the reversible, stereospecific reduction to the 7α-hydroxy group of bile acid.

1. Materials and Methods 1.1 Chemicals

If not specified otherwise all chemicals were purchased from Sigma Aldrich or Carl Roth. Bile acids were obtained from PharmaZell GmbH (Raubling, Germany). Ni-NTA for protein purification was used from MCLAB (Nimagen, Netherlands), Sephadex G 25 from GE Healthcare. Centrifugation was carried out using the centrifuges RC5BPlus, Mikro22 and Rotina 35 R (Thermo Scientific, Dreieich, Germany). For analytical methods HPLC-column was purchased from Merck (Darmstadt, Germany). Restriction enzymes were purchased from Thermo Scientific (Dreieich, Germany).

1.2 Molecular Cloning

The 7α-hsdh gene (Genbank: YP_001086529.1) was obtained via standard PCR– techniques from genomic DNA from *Clostridium difficile* (DSM 12056) provided by Deutsche Sammlung von Mikroorgansimen and Zellkulturen (DSMZ, Braunschweig, Germany). For the following cloning steps primers with recognition sites for the restriction enzymes NdeI and NotI were used for amplification (for: 5'-CCGCCGCAT ATGGAAAAATTACAAGGAAAAATT-3' SEQ ID NO:1 and rev: 5'-CGCCTAGCGGCCGC TTATCCTAATTATCCTAATATAT-3' SEQ ID NO:2). The restriction endonuclease sites for NdeI and NotI are written in bold and the methionine/stop-codon were underlined. The created NdeI-NotI fragment was ligated into the commercially available vector pET28a(+) (Novagen, Madison, Wis., USA) which is under the control of T7-promoter. Thereby the constructed vector has at the N-terminus an 6×His-tag and was named pET28a_Cd7α-HSDH.

The nox2 gene (encoding a NAD(P)H oxidase) was amplified using genomic DNA from *Lactobacillus sanfranciscensis* (DSM 20451) as template and primers with recognition sites for the restriction enzymes NcoI and XhoI were used for the construction of the enzyme with C-terminal 6×His-tag in pET28a(+) (for: 5'-AACCAACCATGGGA ATGAAAGTTATTGTAGTA-3' SEQ ID NO:3, rev: 5'-ATAATAACTCGAGCGTATAGTTTAAGAC-3' SEQ ID NO:4). The restriction endonuclease sites for NcoI and XhoI were in bolt and the methionine-codon was underlined. The created NcoI-XhoI fragment was ligated into the commercially vector pET28a(+)(Novagen, Madison, Wis., USA), which is under the control of T7-promoter. The constructed vector is named pET28a_LsNOX. The correct in-frame DNA sequence and the absence of any mutations were confirmed by sequencing. The corresponding nucleotide- and amino acid sequence of said NAD(P)H oxidase from *Lactobacillus sanfranciscensis* are shown in SEQ ID NO: 49 and 50, respectively.

1.3 Site-Directed Mutagenesis of Cd7α-HSDH

Single mutations were performed on residues Lys16 and Ala37 and double mutations on residue Ala37/Arg38 of SEQ ID NO:34 through Quikchange® PCR protocol. The forward and their complementary reverse primers used for the introduction of the mutations are shown in Table 2. The resulted plasmids from PCR were transformed into *E. coli* DH5a and colonies were picked from LB-agar plates for performing a plasmid preparation followed by sequencing by LGC Genomics (Berlin, Germany).

TABLE 2

Oligonucleotides used for the creation of the NAD-dependent mutants.
Mutation introducing triplets are shown in bold.

| Primer | SEQ ID NO | Sequence (5'-3') |
|---|---|---|
| K16A for | 5 | AAATTGCAGTAGTTACTGCAGCAACAGCAGGTATTGGATTAGCATCAG |
| K16A rev | 6 | CTGATGCTAATCCAATACCTGCTGTTGCTGCAGTAACTACTGCAATTT |
| K16G for | 7 | AAATTGCAGTAGTTACTGCAGCAACAGGAGGTATTGGATTAGCATCAG |
| K16G rev | 8 | CTGATGCTAATCCAATACCTCCTGTTGCTGCAGTAACTACTGCAATTT |
| K16D for | 9 | TTGCAGTAGTTACTGCAGCAACAGATGGTATTGGATTAGCATCAG |
| K16D rev | 10 | CTGATGCTAATCCAATACCATCTGTTGCTGCAGTAACTACTGCAA |
| A37E for | 11 | GAGCAACTGTGTACTTAGCAGAGCGTTCAGAAGAATTAGCTCAT |
| A37E rev | 12 | ATGAGCTAATTCTTCTGAACGCTCTGCTAAGTACACAGTTGCTC |
| A37D for | 13 | GCAACTGTGTACTTAGCAGATCGTTCAGAAGAATTAGCT |
| A37D rev | 14 | AGCTAATTCTTCTGAACGATCTGCTAAGTACACAGTTGC |
| A37D/R38I for | 15 | AAATGGAGCAACTGTGTACTTAGCAGATATTTCAGAAGAATTAGCTCATGAAGT |
| A37D/R38I rev | 16 | TAACTTCATGAGCTAATTCTTCTGAAATATCTGCTAAGTACACAGTTGCTCCATTT |
| A37D/R38L for | 17 | GAGCAACTGTGTACTTAGCAGATCTTTCAGAAGAATTAGCTCATGA |
| A37D/R38L rev | 18 | TCATGAGCTAATTCTTCTGAAAGATCTGCTAAGTACACAGTTGCTC |

Mutation positions refer to the amino acid sequence of the native enzyme (SEQ ID NO: 34)

1.4 Bacterial Strains and Growth Conditions

*Escherichia coli* strain DH5α (Novagen, Madison, Wis., USA) was grown at 37° C. in Luria Bertani (LB)-medium containing 50 µg/ml kanamycin. Starting cultures of *E. coli* BL21(DE3) Δ7α-HSDH cells carrying the recombinant plasmid were cultivated overnight at 37° C. in 5 mL LB medium, containing 50 µg/ml kanamycin. These cultures were used to inoculate the main cultures in LB- or TB- medium (TB: 24 g L$^{-1}$ yeast extract, 12 g L$^{-1}$ casein hydrolysate, 5 g L$^{-1}$ glycerol in 100 mM potassium phosphate buffer (KPi) pH 7.0) containing 50 µg/ml kanamycin for expression in shaking flasks at a final concentration of 0.05 optical density at 600 nm (0D600). When the OD$_{600}$ reached a value between 0.6 and 0.8, the production of the recombinant 7α-HSDH was induced by the addition of isopropyl thio-β-D-galactoside (IPTG) to a final concentration of 0.5 mM. The cultures were shaken for 20 h in at 25° C. or and harvested by centrifugation.

1.5 Preparation of Cell-Free Extracts

The bacterial cultures were harvested by centrifugation at 10,000×g for 30 min at 4° C. A cell suspension (20%) was prepared in 50 mM KPi buffer pH 8.0 or lysis buffer (300 mM NaCl, 10 mM imidazole, 50 mM NaH$_2$PO$_4$, pH 8.0), respectively. Cells were disrupted by three sonification cycles of 1 min (25% power output) with cooling periods in-between. The lysed cells were centrifuged at 18,000×g for 30 min at 4° C., and the supernatant was used for determination of HSDH or NOX activity, respectively. Protein concentrations were determined according to Bradford using BSA as a standard (Bradford 1976).

1.6 Purification of Enzymes

Purified Cd7α-HSDH was obtained by Ni-NTA immobilised metal affinity chromatography (IMAC). The column was equilibrated with 25 mL lysis buffer (10 mM imidazole, 300 mM NaCl, 50 mM NaH$_2$PO$_4$, pH 8). The cell lysate containing Cd7α-HSDH his-tag (SEQ ID NO: 35) fusion protein was applied on the column and washed with 40 mL washing buffer (20 mM imidazole, 300 mM NaCl, 50 mM NaH$_2$PO$_4$, pH 8.0). The bound protein was eluted with an 10 mL elution buffer (250 mM imidazole, 300 mM NaCl, 50 mM NaH$_2$PO$_4$, pH 8.0). After a desalting step by gel filtration with PD10 column (Sephadex G25, GE healthcare, Germany) the enzyme was stored in 50 mM KPi pH 8.0 and kept at +4° C. until use.

NAD(P)H oxidase was not further purified and used a crude extract.

1.7 Protein Analysis by SDS-PAGE

Protein overexpression was monitored by SDS-PAGE according to Bradford using BSA as a standard. For the expected mass of 30 kDa, a tris-glycine gel containing 15% acrylamide was used. Samples were incubated for 10 min at 95° C. in loading buffer and 10 µg were loaded on the gel. The gels were stained with Coomassie® Brilliant Blue R-250 and molecular mass under denaturing conditions was determined by comparison with standard markers (Thermo Scientific, Dreieich, Germany).

1.8 Enzyme Assay

The enzyme assay mixture for Cd7α-HSDH contained, in a total volume of 1 mL, 50 mM KPi (pH 8.0), 0.5 mM NADP$^+$ respectively 0.2 mM NADPH, 10 mM bile acid and protein in cuvettes. The enzyme assay mixture for NOX contained in a total volume of 1 mL, 50 mM KPi (pH 7.0), 0.2 mM NADPH and protein in cuvettes. One unit of activity was defined as the amount of enzyme catalysing the reduction of 1 μmol NADP⁺ or the oxidation of 1 μmol NADPH, respectively under standard conditions (340 nm, 30° C., pH 8.0) using a spectrophotometer (UV-1700 PharmaSpec, Shimadzu). The reduction assay mixture contained 874 μL buffer (50 mM KPi buffer pH 8.0), 100 μL 7-KLCA (100 mM in 50 mM KPi buffer pH 8.0), 16 μL NADPH (12.5 mM in a. dest.) and 10 μL enzyme solution for the Cd7α-HSDH. The assay for NOX contains 974 μL buffer (50 mM KPi buffer pH 7.0), 16 μL NADPH (25 mM in a. dest) and 10 μL enzyme solution. The oxidation assay mixture contained 870 μL buffer (50 mM KPi buffer pH 8.0), 100 μL CDCA or CA, respectively (100 mM in 50 mM KPi buffer pH 8.0), 20 μL NADP⁺ (25 mM in a. dest) and 10 μL enzyme solution. Reactions were started by addition of the enzyme solution and measured over 30 seconds. For determination of the kinetic constants ($K_M$ and $v_{max}$) parameters were calculated from multiple measurements (at least as triplicates) according to the Michaelis-Menten equation using a non-linear fitting algorithm (Graph pad software).

1.9 Chromatographic Determination of Product

HPLC analysis was performed on a Purospher® STAR RP-18 column (Merck, Germany) on a HPLC LC-2010AHT-System (Shimadzu, Japan) at a flow rate of 1 ml/min. The mobile phase consisted of two eluents. Eluent A was distilled water (pH 2.6 adjusted with orthophosphoric acid 85%) and eluent B HPLC-grade acetonitrile. The starting condition for the gradient program was 65% eluent A and 35% eluent B. The system was monitored by UV detector at 200 nm. Totally, 20 μl samples with a bile acid concentration in the range of 1 mg/ml were analyzed. Authentic samples of CDCA, 7-KLCA and UDCA at the same concentration were used as references.

1.10 Small-Scale Biotransformation

For the biotransformation in a small-scale 10 mM CDCA in KPi-buffer (100 mM, pH 7.0), 0.1 mM NADP⁺, 0.5 U mL⁻¹ Cd7α-HSDH and 5 U mL⁻¹ NADPH-oxidase were incubated at 25° C. The biotransformation were done in glass vials with a stirring bar in it and a stirrer speed of 500 rpm for 18 hours. Samples were taken periodically and diluted with methanol-water (pH 2.6) (9:1 v/v) for HPLC-analysis.

1.11 Structure Modelling

The structure of Cd7α-HSDH was modelled with "Swiss-model" using fabG as template (PDB code: 4JRO) [22-25]. FabG [3-oxoacyl-(acyl-carrier-protein) reductase from *Bacillus anthracis*] was chosen as starting point due to the highest similarity (38%) for modelling. Using 3DLigandSite, the cofactor NAD(P)H was integrated into the structure for the proteins [26]. Structural alignments and structure comparisons were performed with Yasara (Yasara molecular graphics and modelling program, Version 12.11.25).

2. Experimental Results of Example I

CDCA represents an attractive starting material to synthesize UDCA because only the hydroxyl group at C-7 must be converted from the α- into β-position. This epimerization can be reached in a redox-neutral cascade reaction by coupling the NAD(P)H-producing oxidation of CDCA at C-7 catalyzed by 7α-hydroxysteroid dehydrogenase (HSDH) with the NAD(P)H-consuming reduction of the 7-keto group by 7β-HSDH.

2.1 Sequence and Structural Comparison

An amino acid sequence alignment of four 7α-HSDHs from *E. coli, C. perfringens, C. sordellii* and *B. fragillis* and the HSDH from *C. difficile* of the present invention was performed using the "Clustal Omega" alignment tool (FIG. 1).

Considerable sequence identity was observed over the entire sequence with respect to the different origins of the investigated enzymes from *E. coli* respectively *B. fragillis*. Furthermore, several highly conserved regions are present. Based on these results the Cd7α-HSDH could be classified as a typical member of the short-chain dehydrogenases/reductases (SDR) (P. Lepercq, P. Gérard, F. Béguet, J.-P. Grill, P. Relano, C. Cayuela, et al., Isolates from normal human intestinal flora but not lactic acid bacteria exhibit 7a- and 7β-hydroxysteroid dehydrogenase activities, Microb. Ecol. Heal. Dis. 16 (2004) 195-201. doi:10.1080/08910600410033393). Moreover, we modelled the structure of Cd7α-HSDH to understand the interaction between the enzyme and coenzyme and to alter the specificity from NADP(H) to NAD(H).

2.2 Cloning, Overexpression and Purification

For the recombinant overexpression of Cd7α-HSDH and its mutants, an *E. coli* BL21(DE3) hsd⁻ kan⁺ knock-out mutant (*E. coli* BL21(DE3) Δ7α-HSDH) was used as host, leading to a high level of recombinant Cd7α-HSDH. The purified Cd7α-HSDH (SEQ ID NO: 35) with a calculated molecular weight of 30,154.3 Da (including the N-terminal 6×his-tag) was identified as a single band at 30 kDa as judged by SDS-PAGE analysis (FIG. 2). Already in the crude extract (lane 1), the high over-expression of this enzyme could be demonstrated by this method.

2.3 Enzyme Activity and Kinetic Constants

The activity of Cd7α-HSDH were studied using CDCA as substrate. In cell-free crude extracts the activity was found to be 3.6 U mg⁻¹ and 5.5 U mg⁻¹ of the purified sample measured with CDCA and NADP⁺. With NAD⁺ a slight background activity in the order of 0.11 U mg⁻¹ could be detected. Expression in TB-medium resulted in a slightly increased activity of 4.5 U mg⁻¹ (crude extract) and 7.7 U mg⁻¹ (purified) (NADP⁺ as cofactor).

The kinetic parameters (KM and $v_{max}$) for the substrates and cofactors are summarized in Table 3. These data reveal that CA is oxidized with a 10-times higher activity than CDCA. Unexpectedly, the reduction of 7-ketolithocholic acid (7-KLCA) with NADPH leading to CDCA occurs with a quite low activity of 1.1 U mg⁻¹ compared to 8.5 U mg⁻¹ for the oxidation of CDCA. It is notable that no substrate inhibition was observed neither for higher concentrations of CDCA nor for NADP⁺ Studies concerned that the cofactor dependency of Cd7α-HSDH preferred NADP⁺ over NAD⁺. Using NADP⁺, a 100-fold increase in activity at high CDCA substrate concentration (≥2.5 mM CDCA) was observed compared to the activity achieved with the same concentration of NAD⁺. The reason of this behaviour is an unusual strong substrate inhibition observed with the cofactor NAD⁺. The highest activity occurred only within a small range at 0.1 mM CDCA with a sharp drop at higher concentration; already at 2.5 mM only about 10% residual activity was measured.

TABLE 3

Kinetic parameters for wild-type Cd7α-HSDH. The substrate concentration was varied to determine $K_M$ and $v_{max}$, the co-substrate was held at a constant concentration.

| substrate | Co-substrate | $v_{max}$ (U mg$^{-1}$) | $K_M$ (μM) | $k_{cat}$ (s$^{-1}$) | $k_{cat}/K_M$ (s$^{-1}$ mM$^{-1}$) |
|---|---|---|---|---|---|
| CDCA | NADP$^+$ | 8.5 ± 0.1 | 10.1 ± 1.0 | 4.3 ± 0.1 | 419 ± 33 |
| NADP$^+$ | CDCA | 11.2 ± 0.4 | 42.9 ± 9.1 | 5.6 ± 0.2 | 131 ± 20 |
| 7-KLCA | NADPH | 1.1 ± 0.02 | 24.74 ± 6.4 | 0.6 ± 0.0 | 22 ± 4 |
| CA | NADP$^+$ | 91.9 ± 1.4 | 117.3 ± 13.4 | 46.1 ± 0.7 | 391 ± 35 |
| NADP$^+$ | CA | 159.7 ± 3.2 | 49.5 ± 7.2 | 80.1 ± 1.6 | 1618 ± 178 |

The measurements wre performed in a substrate concentration range of between 5 μM and 30 mM bile acid with constant 0.5 mM NAD(P)$^+$ for the oxidation and 0.2 mM NADPH for the reduction. For the cofactor measurements were performed in a range of between 1 μM and 10mM NADP$^+$ at constant 1 mM bile acid.
$^{a)}$ = According to a strong substrate inhibition at concentration above 0.1 mM CDCA the apparent $v_{max}$ was used to determine the kinetic parameters.

2.4 Dependence of Cd7α-HSDH Activity on Temperature

Figure 3:
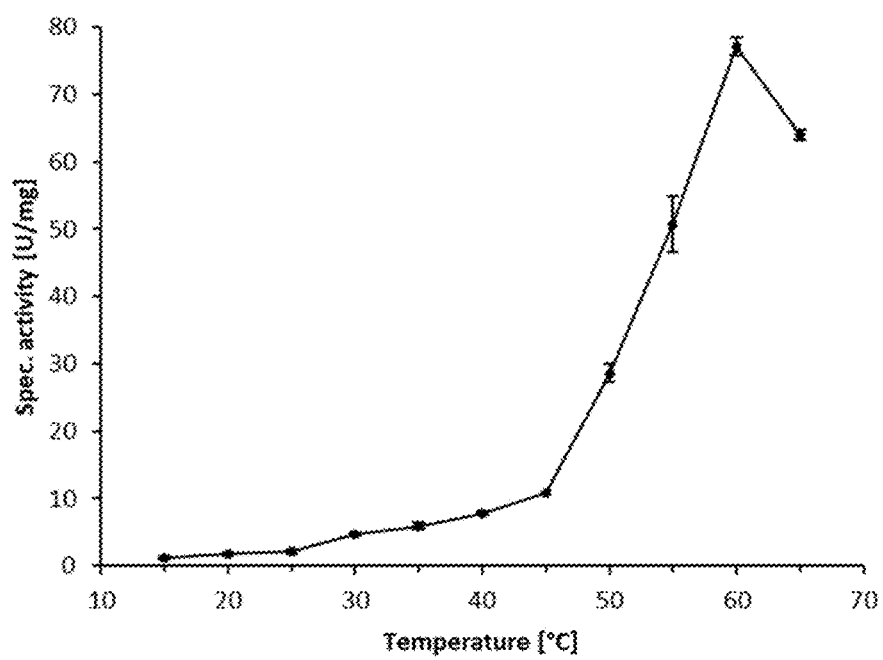
FIG. 3: Specific activity of 7α-HSDH at different temperatures. The effects of temperature on the enzyme activity were measured with crude extract by using a specto-photometrical assay for the oxidation of CDCA (50 mM KPi buffer at pH 8.0, 1 mM CDCA and 0.5 mM NADP$^+$).

The influence of temperature on the enzyme activity was investigated between 15 and 65° C. using CDCA as substrate (FIG. 3). All measurements were carried out with purified protein (with N-His-Tag). Cd7α-HSDH showed a slight increase in activity up to 45° C. with 11 U mg$^{-1}$. From 45° C. to 60° C. the activity increased rapidly with a maximum of 60° C. (77 U mg$^{-1}$) followed by a rapid decrease due to protein denaturation. Regarding the temperature stability a residual activity of only 5% was detected at incubation for 5 min at 60° C.

2.5 Dependence of the Cd7α-HSDH Activity on Product Concentration

Figure 4:
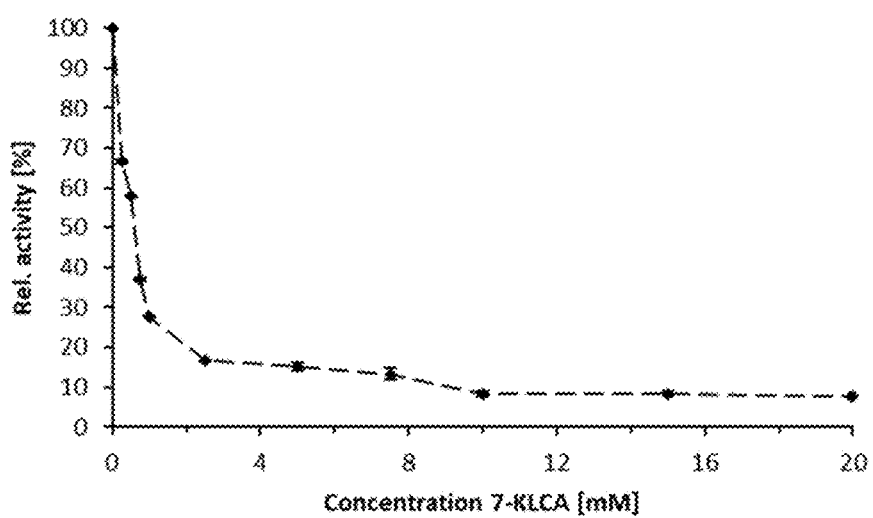
FIG. 4: Relative activity of Cd7α-HSDH with increasing concentration in the range of 0-20 mM of the product 7-KLCA. The standard activity assay with 1 mM CDCA as substrate was used.

The inhibitory effect of the product 7-KLCA on the Cd7α-HSDH is a crucial parameter in processes converting CDCA into UDCA. Therefore, we measured the residual activity of the dehydrogenase in the presence of different concentration of 7-KLCA. The photometric assay is similar to the standard activity assay, only CDCA was used at 1 mM instead of 10 mM. FIG. 4 shows that the product 7-KLCA is a strong inhibitor of Cd7α-HSDH (with N-His-Tag). Already in the presence of 1 mM of the product the activity is reduced to 28% and at 2.5 mM only about 10% residual activity could be measured.

2.6 Biotransformation of CDCA

To confirm the applicability of this enzyme, a 10 mL scale biotransformation of 39 mg (10 mM) CDCA was carried out using the Cd7α-HSDH (with N-His-Tag) (SEQ ID NO: 35) combined with a NAD(P)H oxidase (SEQ ID NO: 51) (with C-His-Tag) from Lactobacillus sanfranciscensis for regeneration of NADP$^+$ according to scheme 2.

Figure 5:
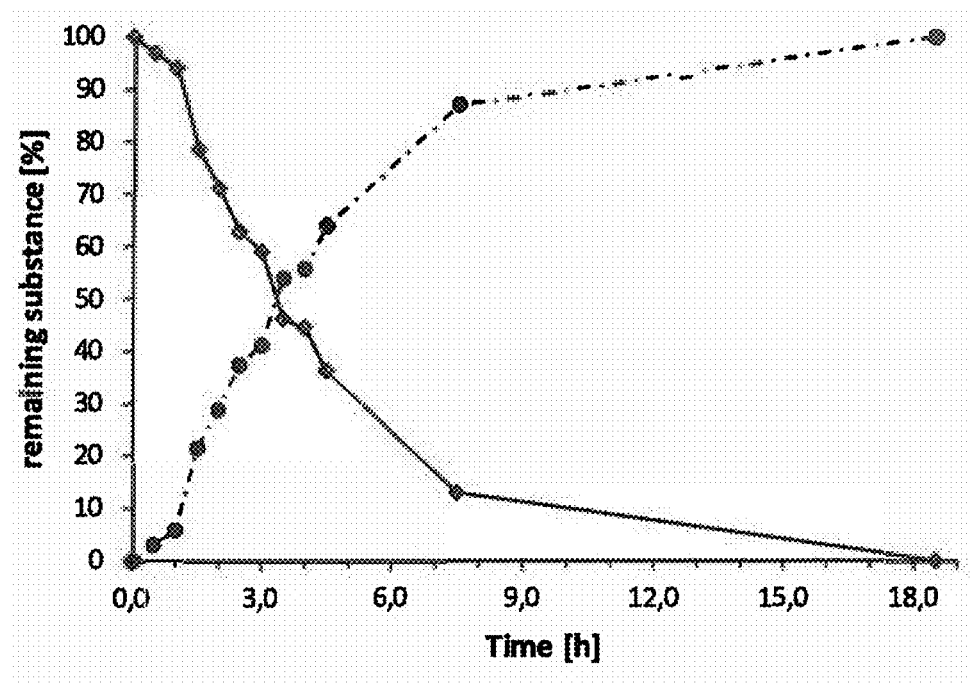
FIG. 5: Biotransfomation of CDCA (10 mM) in aqueous system (KPi, pH 7.0), containing 5 U Cd7α-HSDH and 50 U NOX during 18.5 hours. After 3.5 h and 7 h additional 50 U NOX were added to the reaction. Concentration of CDCA (-○-CDCA) and 7-KLCA (-●-7-KLCA) were determined by HPLC.

The HPLC analysis indicates that 7-KLCA was the only product from CDCA with a conversion of >99% after 18.5 h (FIG. 5). The complete conversion is only possible due the irreversibility and high driving force of the NAD(P)H oxidase. Unfortunately, the oxidase exhibits a limited stability, therefore this enzyme has been replenished after 3 and 7 hours to ensure a full conversion.

2.7 Alteration of Coenzyme Specificity

Figure 6:
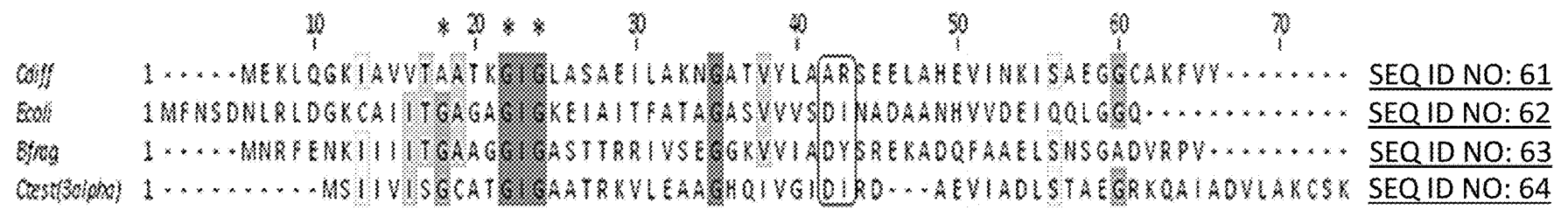

Wild-type Cd7α-HSDH (with our without N-His-tag; SEQ ID NO: 34 or 35) shows a coenzyme preference towards NADP$^+$ with a small side activity (<0.1%) with NAD$^+$. However, due the lower costs and higher stability of NAD$^+$, the application of this coenzyme in industrial uses might be advantageous. In order to increase NAD$^+$ activity, an amino acid sequence alignment of the cofactor binding region of the NADP$^+$-dependent Cd7α-HSDH with NAD-dependent HSDHs from different organisms was carried out (FIG. 6). This alignment revealed that the cofactor binding site is highly conserved showing the typical glycine motif (G/A)XXXGXG (SEQ ID NO: 57) (where X is any amino acid). Ala37 and Arg38 were targeted for mutation aiming at introducing an acid residue at position Ala37 and a small hydrophobic residues instead of Arg38. FIG. 7 demonstrates that the presumable function of Ala37 is to provide space for the 2'-phosphate-group. For the discrimination of NADP$^+$-binding by either unfavourable interactions due to charge repulsion or steric hindrance effects could be possible by introducing an aspartic or glutamic acid (FIG. 7, B).

In fact, the single mutants A37E and A37D showed increased activity against NAD$^+$ (0.2 and 0.9 U mg$^{-1}$) as well as reduced activity against NADP$^+$ (0.2 and 0.4 U mg$^{-1}$) compared to the wild-type enzyme with 0.04 U mg$^{-1}$ Scheme 2

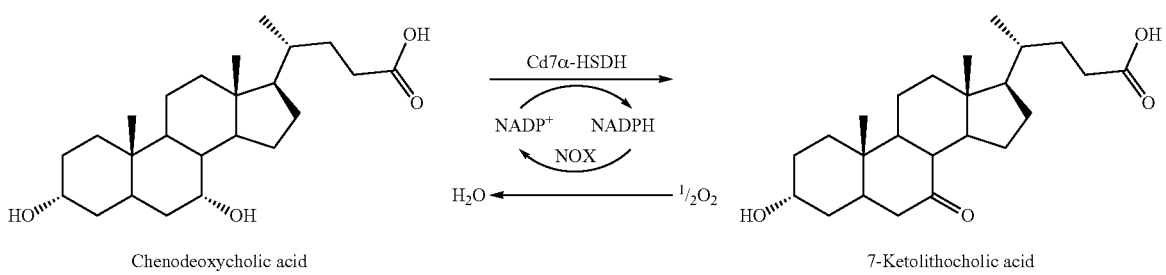

Chenodeoxycholic acid → 7-Ketolithocholic acid

Scheme 2. Oxidation of chenodeoxycholic acid (CDCA) to 7-ketolithocholic acid (7-KLCA) using Cd7α-HSDH with simultaneous regeneration of NADP$^+$ by NAD(P)H oxidase (NOX) from Lacto-bacillus sanfranciscensis.

(NAD$^+$) and 3.2 U mg$^{-1}$ with NADP$^+$. This corresponds to a 22-fold increase of activity with NAD$^+$ for the mutant A37D related to the wild-type. This single mutation resulted in a better NAD$^+$-specific activity than the double mutant A37D/R38I or A37D/R38L (0.1 U/mg for both mutants with NAD$^+$).

Figure 8:
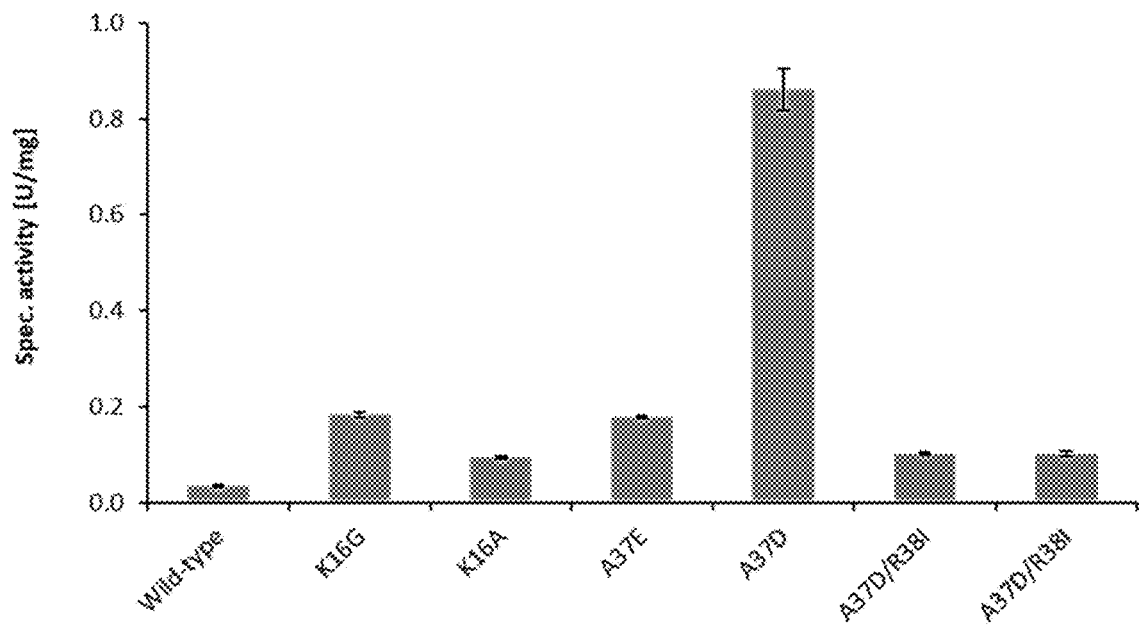
FIG. 8: Comparison of the NAD+-dependent activities of the mutants with the wild-type of Cd7α-HSDH using 10 mM CDCA, 0.5 mM NAD+, and crude extract enzyme.

Due to the structure modelling of this enzyme, another amino acid, Lys16 (SEQ ID NO: 34) was identified to interact possibly with the 2'-phosphate group of NADP$^+$. This consideration led to the creation of new single (K16A, K16G and K16D) and double mutants (K16A/A37D and K16G/A37D) with altered amino acids at position 16. Indeed, it could be shown that the small residue from glycine increased the activity with NAD$^+$ of about 6-fold (0.2 U mg$^{-1}$) in comparison with the wild-type enzyme whereas the introduction of alanine or aspartic acid (in comparison to glycine) decreased the activity (0.09 and 0.01 U mg$^{-1}$, respectively). However, all mutants (K16A, K16G and K16D) have higher activity as compared to the wild type. The double mutant K16G/A37D and K16A/A37D does not have an increasing effect on the activity with NAD$^+$ as cofactor. FIG. 8 summarizes the NAD$^+$-activities for the mutants.

Furthermore, kinetic parameters were determined for the best NAD$^+$-mutant A37D.

The kinetic parameters of the purified recombinant Cd7α-HSDH toward CDCA were determined at 25° C. in 50 mM KPi-buffer (pH 8.0) by increasing the CDCA concentration from 0.05 to 30 mM at a fixed NAD$^+$ concentration of 0.5 mM. Each test was carried out in triplicate. Owing to a strong substrate inhibition with the cofactor NAD$^+$, a fit with the standard Michaelis-Menten equation was not possible. Therefore, the kinetic parameters were calculated using the apparent $v_{max}$. The results are summarized in Table 4:

TABLE 4

Kinetic constants for Cd7α-HSDH [A37D] mutant. The substrate concentration was varied to determine $K_M$ and $v_{max}$, the concentration of the co-substrate was held constant. n.e. = not existing

| co-substrate | substrate | $v_{max}$ | $K_M$ | $k_{cat}$ | $k_{cat}/K_M$ | $K_I$ |
|---|---|---|---|---|---|---|
| CDCA $^{a)}$ | NAD$^+$ | 19.5 ± 3.7 | 0.34 ± 0.08 | 9.8 ± 1.9 | 29 ± 1.4 | 4.9 ± 24.7 |
| NAD$^+$ | CDCA | 44.8 ± 2.3 | 4.0 ± 0.4 | 22.5 ± 1.2 | 6 ± 0.3 | n.e. |

The measurements were performed in a substrate concentration range of between 5 μM and 30 mM CDCA with constant 0.5 mM NAD$^+$. Cofactor measurements were performed in a range between 1 μM and 7.5 mM NAD$^+$ at constant 0.1 mM CDCA.
$^{a)}$ = According to a strong substrate inhibition at concentration above 0.1 mM CDCA the apparent $v_{max}$ was used to determine the kinetic parameters.

3. Summary

Our attempt to switch the coenzyme specificity from NADP$^+$ to NAD$^+$ by structure-based site-directed mutagenesis resulted in in several mutants, and in particular two enzyme single mutants (A37E and A37D) with a significant increase in activity with NAD$^+$ as compared to the wild-type. Especially A37D showed a specific activity of 0.9 U/mg. Moreover, this resulted in a strong decrease in activity with the coenzyme NADP$^+$ for this mutant (0.4 U/mg residual activity in comparison with 3.2 U/mg for the wild-type. In sum, the obtained mutants, and in particular the A37D enzyme variant now offers the possibility to combine 7α-HSDH activity with NADH oxidase to obtain 7-KLCA or with an NADH-dependent 7β-HSDH to produce UDCA.

Example II: Cloning, Expression, and Biochemical Characterization of Novel NADP-Dependent Mutants, in Particular Cofactor Switch Mutants, of 7α-Hydroxysteroid Dehydrogenase from *Escherichia coli* and their Application for the Oxidation of Bile Acids 1. Materials and Methods 1.1 Chemicals All chemicals, as for example, antibiotics, were obtained from Sigma-Aldrich or Carl Roth (Germany). All restriction endonucleases and T4 DNA ligase were obtained from ThermoScientific (Germany) and isopropyl thio-β-D-galactoside (IPTG) was obtained from Gerbu (The Netherlands).

1.2 Media & Buffers:

LB medium: Tryptone 10 g, yeast extract 5 g, NaCl 10 g per liter medium

KPi buffer: (50 mM, pH 8), containing 8.3 g K$_2$HPO$_4$ and 0.3 g KH$_2$PO$_4$ per liter buffer Disintegration buffer: 10 mM Imidazol, 50 mM sodium phosphate, 300 mM NaCl, pH 8

Washing buffer: 20 mM Imidazol, 50 mM sodium phosphate, 300 mM NaCl, pH 8

Eluation buffer: 250 mM Imidazol, 50 mM sodium phosphate, 300 mM NaCl, pH 8

1.3 Microorganisms:

TABLE 5

Applied *Escherichia coli* strains

| Strain | Genotype |
|---|---|
| *Escherichia coli* DH5α | F– endA1 glnV44 thi-1 recA1 relA1 gyrA96 deoR nupG Φ80dlacZΔM15 Δ(lacZYA-argF)U169, hsdR17(rK– mK+),λ– |
| *Escherichia coli* BL21 (DE3) Δ7α-HSDHF– (7α-HSDH Knock-out strain) | ompT gal dcm Ion hsdSB(rB– mB–) λ(DE3 [lacI lacUV5-T7 gene 1 ind1 sam7 nin5]) hshA– KanR+ |

The E. coli strain DH5a (Novagen, Madison, Wis., USA) was grown at 37° C. in LB medium, containing suitable antibiotics.

The E. coli strain BL21(DE3) Δ7α-HSDH (see Pharmazell GmbH patent application WO 2011/147957 in particular relating to 7α-HSDH knock out mutant) was grown at 37° C. in LB medium, containing suitable antibiotics and was incubated after induction at $OD_{600}$=0.6-0.8 with 0.5 mM IPTG, for 20 hours at 25° C. and at 130 rpm.

1.4 Expression Vectors and Vector Constructs:

For expressing recombinant 7α-HSDH, the expression vector pET28a(+) (Novagen, Madison, Wis., USA) has been applied and the following vector constructs have been generated:

pET28a(+)_7α-HSDH(−): pET28a(+)-vector, wherein the corresponding E. coli 7α-HSDH gene was cloned by means of standard procedures into the cleavage sites NcoI and XhoI. The construct contains no 6×His-tag.

pET28a(+)_7α-HSDH(N): pET28a(+)-vector, wherein the corresponding E. coli 7α-HSDH gene was cloned by means of standard procedures into the cleavage sites NdeI and XhoI. This construct contains an N-terminal 6×His-tag.

pET28a(+)_7α-HSDH(C): pET28a(+)-vector, wherein the corresponding E. coli 7α-HSDH gene was cloned by means of standard procedures into the cleavage sites NcoI and XhoI. Said construct contains a C-terminal 6×His-tag.

1.5 Cultivation

Cultivation was performed in a shaking flask in LB medium at 37° C. At an $OD_{600}$=0.6-0.8, gene expression was induced by the addition of 0.5 mM IPTG. Afterwards, the cells were grown at 25° C. for 20 hours and were then harvested.

1.6 Production of Crude Extract

The cultivated cells were disrupted by means of ultrasonication (25% (w/v) cell suspension) and the thus obtained crude extract was applied in activity assays.

1.7 Standard Conditions for 7α-HSDH Activity Measurement

The reaction mixture contained in a total volume of 1 ml:
880 µl 50 mM potassium phosphate ($KP_i$) buffer, pH 8.0
100 µl 100 mM CDCA (dissolved in 50 mM $KP_i$, pH 8)
10 µl Enzyme solution (in buffer as above, in the range of 2 to 6 U/ml)
10 µl 50 mM $NAD^+$ or $NADP^+$ (dissolved in $ddH_2O$)

An increase of extinction was determined at 340 nm over a period of 30 seconds and the activity was expressed as enzyme unit (1 U corresponds to a conversion of 1 µmol NAD(P)H/min). The molar extinction coefficient was 6.22 $mM^{-1} \times cm^{-1}$.

1.8 Protein Determination by Means of Bradford Method

The samples (100 µl) were mixed with 900 µl Bradford reagent and were incubated for at least 15 min in the dark. The protein content was determined at 595 nm with BSA as calibrator in the concentration range of the applied assay.

1.9 Molecular Biological Methods

Unless otherwise indicated, established methods have been applied as, for example, disclosed in: Sambrook, J., Fritsch, E. F. and Maniatis, T. Molecular Cloning: A Laboratory Manual. 2. ed., Cold Spring Harbor Laboratory, Cold Spring Harbor Laboratory Press, Cold Spring Harbor, N.Y., 1989; Ausubel et al. (eds.), Current Protocols in Molecular Biology, John Wiley & Sons, N Y (1993); Kriegler, Gene Transfer and Expression, A Laboratory Manual, Stockton Press, N.Y. (1990).

1.10. QuikChange®-PCR

By means of QuikChange®-PCR (QC-PCR), the directed exchange of individual amino acid residues was performed. The applied primers are summarized in the subsequent Table 6. Said primers cause the intended amino acid exchange in positions 42 and/or 43.

TABLE 6

Primers for QuikChange-PCR.

| Name | 5' → 3' Sequence | Exchanged amino acid | SEQ ID NO. |
|---|---|---|---|
| D42G/I43R_for | catctgtggtggtcagtggtaggaacgccgacgcagctaac | glycine & | 19 |
| D42G/I43R_rev | gttagctgcgtcggcgttcctaccactgaccaccacagatg | asparagine | 20 |
| D42A/I43R_for | catctgtggtggtcagtgctaggaacgccgacgcagctaac | alanine & | 21 |
| D42A/I43R_rev | gttagctgcgtcggcgttcctagcactgaccaccacagatg | asparagine | 22 |
| D42G_for | gtggtggtcagtggtattaacgccgac | glycine | 23 |
| D42G_rev | gtcggcgttaataccactgaccaccac | | 24 |
| I43R_for | gcatctgtggtggtcagtgataggaacgccgacgca | asparagine | 25 |
| I43R_rev | tgcgtcggcgttcctatcactgaccaccacagatgc | | 26 |

For performing said reaction, in a first step, a denaturation step was performed at 95° C. for 2 min. Thereafter followed 23 cycles of denaturation (30 s at 95° C.), primer hybridization and elongation (11 min at 72° C.). As the last step, a final elongation was performed for 10 min at 72° C. before the polymerase chain reaction was terminated by cooling down to 15° C.

TABLE 7

PCR reaction mixture for generating different 7α-HSDH variants
Reaction mixture

| | |
|---|---|
| Buffer (10x) | 5.0 µl |
| dNTP-Mix (10 mM) | 1.5 µl |
| Forward Primer (10 pmol/µl) | 2.0 µl |
| Reverse Primer (10 pmol/µl) | 2.0 µl |
| Template | 1.0 µl |
| Pfu Polymerase | 0.5 µl |
| DMSO | 2.5 µl |
| $ddH_2O$ | 35.5 µl |
| | 50.0 µl |

As template, a pET28a-vector with 7α-HSDH (wildtype) coding sequence was applied. In particular, the N6-adenine-methylated double-stranded plasmid DNA of the gene to be mutated was applied. N6-adenine-methylated plasmid DNA was isolated from the $dam^+$ E. coli strain E. coli DH5α (as listed above).

The PCR was performed as described above. Afterwards, the PCR product was purified by means of the PCR purification kit of Analytik Jena. Parental N6-adenine-methylated DNA was digested by means of the restriction enzyme dpnI. This enzyme has the specific feature that it restricts non-specifically N6-adenine-methylated DNA. However, it does not react with newly formed non-methylated DNA. The restriction was performed by adding 1 µl dpnI to the purified PCR reaction product for at least 2 hours or overnight at 37° C.

8 µl of said reaction mixture were applied for the transformation of 100 µl of chemically competent DH5a cells.

1.11. Expression and Purification

E. coli BL21(DE3)Δ7α-HSDH was transformed with the corresponding expression construct. For this purpose, the E. coli BL21(DE3)Δ7α-HSDH strain containing the expression construct was propagated in LB medium, containing 50 µg/ml Kanamycin. The cells were harvested by centrifugation (10.000×g, 30 min, 4° C.). The pellet was suspended in disintegration buffer (25% (w/v) cell suspension). The cells were sonicated for 2 minutes under cooling (30 W, 10-25% working interval and 1 min break). The ultrasonic apparatus Sonopuls HD2070 (Bandelin, Germany) was applied. The disintegration was repeated for three times. The cell extract was centrifuged (20.000×g, 30 min, 4° C.). The supernatant was applied on a column (Thermo Scientific, USA) which had been equilibrated with 25 ml of disintegration buffer. Weakly binding protein was eluted by washing with 40 to 50 ml of washing buffer. The His-tag-7α-HSDH protein was eluted by means of 10 ml of elution buffer. The process was performed at room temperature. The eluate was concentrated by means of a Centricon ultrafiltration module and a buffer exchange was performed by means of a PD10 column in order to remove imidazole.

The protein concentration determined as described above under item 1.8. In addition, each sample was analyzed by means of 15% SDS-PAGE and Coomassie Brilliant Blue staining.

2. Experimental Results of Example II 2.1 Photometric Activity Assay

The photometric activity assay of the crude extract was performed by means of a UV-1700 spectrophotometer (Shimadzu, Japan) (see method described above under item 1.7). In Table 8, the specific activity values of individual mutants as obtained for NAD$^+$ and NADP$^+$ are summarized.

TABLE 8

Activities of individual mutants (crude extracts) observed for the substrate CDCA and one of the co-factors NAD$^+$ and NADP$^+$.

| No. | Enzyme | SEQ. ID NO: | with NAD$^+$ U/mg | with NADP$^+$ U/mg |
|---|---|---|---|---|
| 1 | 7α-HSDH [wildtype] | 38 | 51.6 | 0 |
| 2 | 7α-HSDH [D42G] |  | 0.4 | 0.3 |
| 3 | 7α-HSDH [I43R] |  | 51.8 | 0.4 |
| 4 | 7α-HSDH [D42G/I43R] | 41 | 0.1 | 6.3 |
| 5 | 7α-HSDH [D42A/I43R] |  | 0 | 2.1 |

Figure 9:
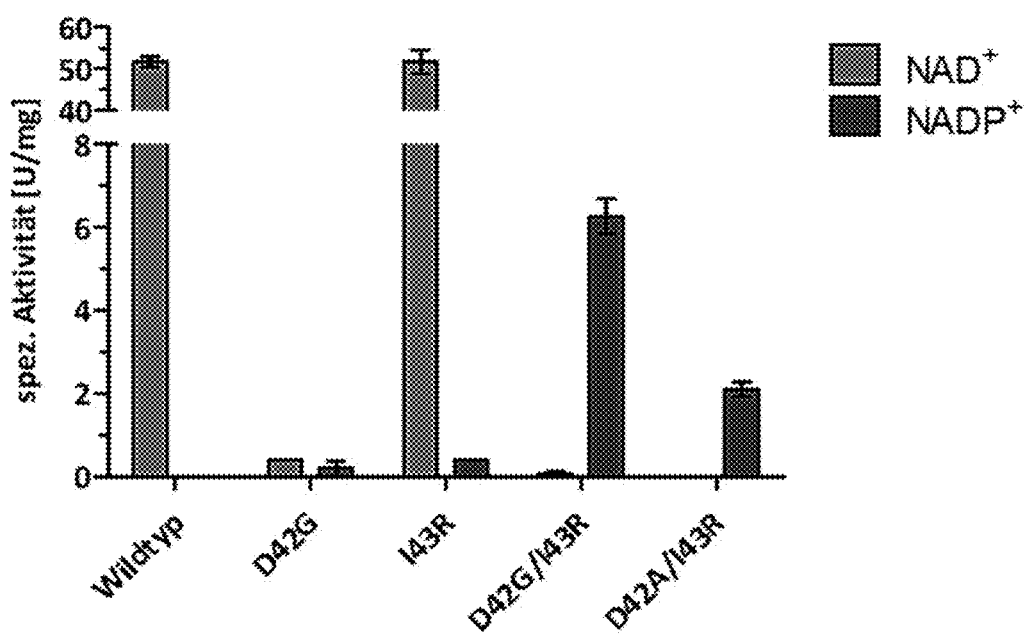
FIG. 9: Comparison of activities of the NADP+-dependent mutants and the wildtype 7α-HSDH of *E. coli* (activity assay with crude extract).

The best mutant (no. 4) shows only marginal activity for the original cofactor NAD$^+$ and an activity of about 6.3 U/mg for the cofactor NADP$^+$. FIG. 9 presents a graphical illustration of the results.

2.2. Biochemical Characterization

Figure 10:
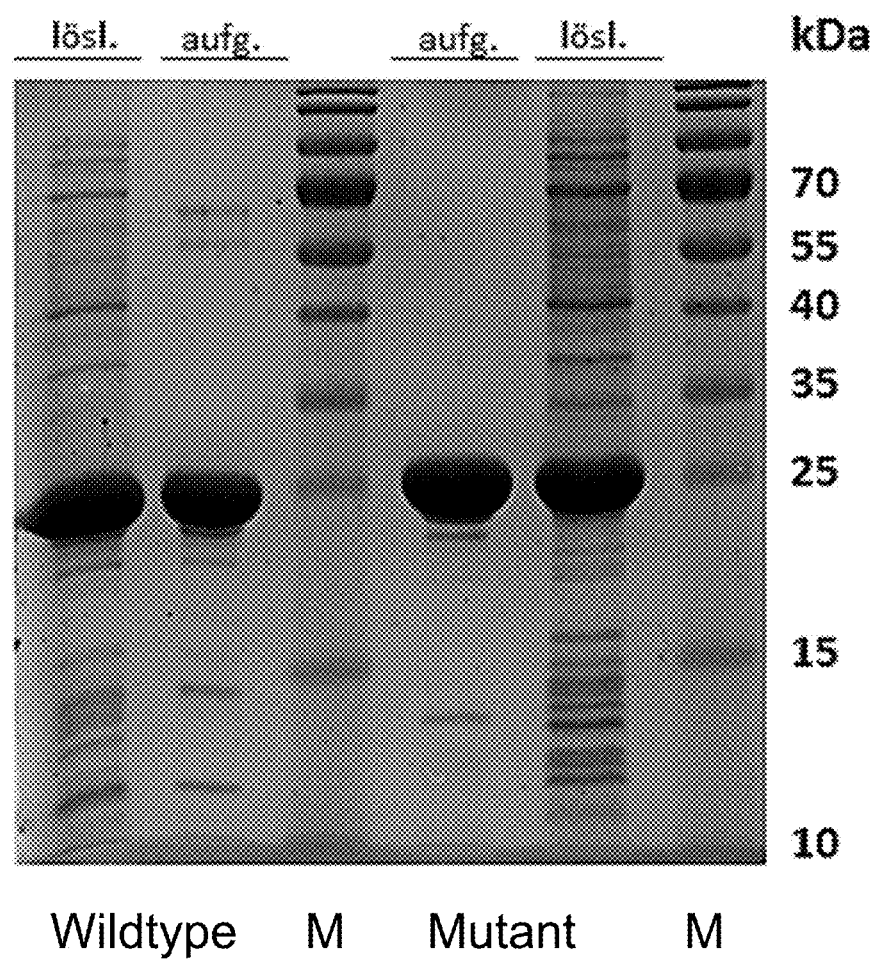
FIG. 10: SDS-PAGE of expression and purification of 7α-HSDH (wildtype and D42G/143R mutant) as observed for crude extract and purified protein. Expression of 7α-HSDH results in approximately 80% of the intended protein. The samples size was about 10 µg protein. Legend: M=Marker; lösl.=crude product; aufg.=purified product.

An SDS-PAGE was performed in order to evaluate the expression power of the homologous expression as well as the quality of the purification. FIG. 10 shows the SDS gel of the mutant 7α-HSDH [D42G/I43R]. The molecular weight of the wildtype as well as of the NADP$^+$ mutant (with an N-term 6×His-tag) (SEQ NO: 41) is about 28.9 kDa. FIG. 10 shows that 7α-HSDHs do not show the theoretical molecular weight. Rather, the bands show a molecular weight of about 25 kDa.

2.3. Michaelis-Menten-Kinetics

The kinetic constants $v_{max}$ and $K_M$ were determined for each mutant as well as for the wildtype enzyme. The measurements were performed for the substrate CDCA and the coenzyme NAD(P)$^+$. The results are also summarized in Table 9. The measurements were performed with purified protein (according to item 7) and at different substrate concentrations in the range of 10 µM and 30 mM for CDCA at a constant concentration of co-factor of 0.5 mM NAD(P)$^+$. The corresponding constants for the co-factor were performed at a CDCA concentration of 1 mM and co-factor concentrations in the range of 10 µM to 5 mM.

TABLE 9

Kinetic constants for 7α-HSDH (wildtype and NADP-dependent mutant).
X = no inhibition; n.d. = not determined

| Variant | Substrate | $v_{max}$ (U/mg) | $K_M$ (µM) | $K_I$ (mM) |
|---|---|---|---|---|
| Wildtype | CDCA | 193.3 ± 7.9 | 56.1 ± 7.8 | 2.96 ± 0.3 |
|  | NAD$^+$ | 151.3 ± 3.1 | 202± | x |
| D42G/I43R | CDCA | a) 167.8 ± 6.3 | a) 327.8 ± 32.2 | n.d. |
|  | NADP$^+$ | 158.7 ± 7.2 | 314.5 ± 45.0 | x | a) = apparent values

The Michaelis-Menten graphs (not depicted) show a substrate inhibition for CDCA for each of said two enzyme variants. For the mutant, inhibition is more pronounced.

Example III: Coupled Self-Sufficient One-Step Conversion of CDCA to UDCA

1. Materials and Methods 1.1 Chemicals

All chemicals as, for example, antibiotics, were obtained from Sigma-Aldrich, Carl Roth or Biomol (Germany). All restriction endonucleases and the T$_4$ DNA ligase were obtained from ThermoScientific (Germany), and isopropyl thio-β-D-galactoside (IPTG) was obtained from Gerbu (The Netherlands).

1.2 Media & Buffers:

LB medium: trypton 10 g, yeast extract 5 g, NaCl 10 g per liter medium

KP$_i$ buffer (50 mM, pH 8): 8.3 g K$_2$HPO$_4$ and 0.3 g KH$_2$PO$_4$ per liter buffer Disintegration buffer: 10 mM imidazole, 50 mM sodium phosphate, 300 mM NaCl, pH 8

Washing buffer: 20 mM imidazole, 50 mM sodium phosphate, 300 mM NaCl, pH 8

Elution buffer: 250 mM imidazole, 50 mM sodium phosphate, 300 mM NaCl, pH 8

1.3 Microorganisms:

TABLE 10

Applied *E. coli* strains

| Strain | Genotype |
| --- | --- |
| *Escherichia coli* DH5α | F– endA1 glnV44 thi-1 recA1 relA1 gyrA96 deoR nupG Φ80dlacZΔM15 Δ(lacZYA-argF)U169, hsdR17(rK– mK+),λ– |
| *Escherichia coli* BL21 (DE3) Δ7α-HSDH (7α-HSDH Knock-out strain) | F– ompT gal dcm lon hsdSB(rB– mB–) λ(DE3 [lacI lacUV5-T7 gene 1 ind1 sam7 nin5]) hshA– KanR+ |

The *E. coli* strain DH5a (Novagen, Madison, Wis., USA) was cultivated in LB medium, containing suitable antibiotics.

The *E. coli* strain BL21(DE3) Δ7α-HSDH was obtained from PharmaZell GmbH (see WO 2011/147957)

1.4 Expression Vectors and Vector Constructs:

For expressing the recombinant 7α and 7β-HSDH enzymes, the per se known expression vectors pET28a(+) as well as pACYCDuet (Novagen, Madison, Wis., USA) have been used to prepare the following vector constructs:

pET28a(+)_7α-HSDH(N) [D42G/I43R]: pET28a(+) vector, in which the gene of 7α-HSDH from *E. coli* was cloned in well-known manner via the restriction sites NdeI and XhoI. By means of QuikChange®-PCR, the mutations D42G and I43R have been introduced. This construct contains a N-terminal 6×His-tag (SEQ NO: 41).

pET28a(+)_Cd7α-HSDH(N): pET28a(+) vector, in which the gene of 7α-HSDH from *C. difficile* was cloned in well-known manner via the restriction sites NdeI and XhoI. This construct contains an N terminal 6×His-tag (SEQ NO: 35).

pA_7β-HSDH: pACYCduet vector, in which the gene of 7β-HSDH from *C. aerofaciens* was cloned in well-known manner via the restriction sites NcoI and XhoI. Said construct contains no 6×His-tag (SEQ NO: 52).

pA_7β-HSDH [G39S/R64E]: pACYCDuet vector, in which the 7β-HSDH gene of *C. aerofaciens* was cloned in well-known manner via the restriction sites NcoI and XhoI. By means of QuikChange®-PCR, the mutations G39S and R64E were introduced. This construct contains no 6×His-tag (SEQ NO: 45).

pET28a(+)_7β-HSDH(C) [G39E]: pET28a(+) vector, in which the gene of 7α-HSDH from *E. coli* was cloned in well-known manner via the restriction sites NcoI and XhoI. By means of QuikChange®-PCR, the mutation G39E was introduced. This construct contains a C terminal 6×His-tag. (SEQ NO: 48)

The recombinant strains which have been used for the one-step synthesis of UDCA from CDCA are listed in Table 11.

TABLE 11

Applied recombinant strains.

| Name | Plasmids |
| --- | --- |
| *E. coli* DB06 | pET28a_CD7α(N) + pA_7β-HSDH [G39S/R64E] |
| *E. coli* DB07 | pET28a_7α-HSDH [D42G/I43R] + pA_7β-HSDH [G39S/R64E] |

The strain *E. coli* BL21(DE3)Δ7α-HSDH was obtained from PharmaZell GmbH and used for preparing said DB06 and DB07strains. (see description below).

1.5 Cultivation

Cultivation was performed in shaking flasks in LB medium at 37° C. At an $OD_{600}$ of 0.6-0.8, the gene expression was induced by the addition of 0.5 mM IPTG. Afterwards, the cells were grown for 20 hours at 25° C. and then harvested.

1.6. Preparation of Crude Extract

The cultivated cells were ultra-sonicated (25% (w/v) cell suspension) and the obtained crude extract was centrifuged (20.000 g, 30 min, 4° C.) in order to remove cell fragments.

1.7. Standard Conditions for HSDH Activity Assay

The reaction mixture contained in a total volume of 1 ml:

880 µl 50 mM potassium phosphate ($KP_i$) buffer, pH 8.0

100 µl 100 mM CDCA or 7-KLCA (dissolved in 50 mM $KP_i$, pH 8)

10 µl enzyme solution (diluted in buffer in the range of 1 to 5 U/ml)

10 µl 50 mM $NAD^+$ or $NADP^+$ (dissolved in $ddH_2O$)

An increase of extinction was determined at 340 nm over a period of 30 seconds and the activity was expressed as enzyme unit (1 U corresponds to a conversion of 1 µmol substrate/min). The molar extinction coefficient was 6.22 $mM^{-1} \times cm^{-1}$.

1.8 Protein Determination by Means of Bradford Method

The samples (100 µl) were mixed with 900 µl Bradford reagent and were incubated for at least 15 min in the dark. The protein content was determined at 595 nm with BSA as calibrator in the concentration range of the applied assay.

1.9 Molecular Biological Methods

Unless otherwise indicated, established methods have been applied as, for example, disclosed in: Sambrook, J., Fritsch, E. F. and Maniatis, T. Molecular Cloning: A Laboratory Manual. 2. ed., Cold Spring Harbor Laboratory, Cold Spring Harbor Laboratory Press, Cold Spring Harbor, N.Y., 1989; Ausubel et al. (eds.), Current Protocols in Molecular Biology, John Wiley & Sons, N Y (1993); Kriegler, Gene Transfer and Expression, A Laboratory Manual, Stockton Press, N.Y. (1990).

1.10. QuikChange®-PCR

By means of QuikChange®-PCR (QC-PCR), the directed exchange of individual amino acid residues was performed. The applied primers are summarized in the subsequent Table 12. Said primers cause the intended amino acid exchange in positions 42 and/or 43.

TABLE 12

Primers for QuikChange-PCR.

| Gene | Name | 5' -> 3'Sequence | SEQ ID NO: | Exchanged amino acid |
|---|---|---|---|---|
| 7α-HSDH | D42G/I43R_for | catctgtggtggtcagtggtaggaacgccgacgcagctaac | 19 | Gly & Asp |
| | D42G/I43R_rev | gttagctgcgtcggcgttcctaccactgaccaccacagatg | 20 | |
| | D42A/I43R_for | catctgtggtggtcagtgctaggaacgccgacgcagctaac | 21 | Ala & Asp |
| | D42A/I43R_rev | gttagctgcgtcggcgttcctagcactgaccaccacagatg | 22 | |
| | D42G_for | gtggtggtcagtggtattaacgccgac | 23 | Gly |
| | D42G_rev | gtcggcgttaataccaactgaccaccac | 24 | |
| | I43R_for | gcatctgtggtggtcagtgataggaacgccgacgca | 25 | Asp |
| | I43R_rev | tgcgtcggcgttcctatcactgaccaccacagatgc | 26 | |
| 7β-HSDH | G395_for | gtcgtcatggtcagccgtcgcgaggag | 27 | Ser |
| | G395_rev | ctcctcgcgacggctgaccatgacgac | 28 | |
| | G39E_for | gtcgtcatggtcgagcgtcgcgaggag | 29 | Glu |
| | G39E_rev | ctcctcgcgacgctcgaccatgacgac | 30 | |
| | R64E_for | accaaggtcgtggaggccgactttagc | 31 | Glu |
| | R64E_rev | gctaaagtcggcctccacgaccttggt | 32 | |

For performing said reaction, in a first step, a denaturation step was performed at 95° C. for 2 min. Thereafter followed 23 cycles of denaturation (30 s at 95° C.), primer hybridization and elongation (11 min at 72° C.). As the last step, a final elongation was performed for 10 min at 72° C. before the polymerase chain reaction was terminated by cooling down to 15° C.

TABLE 13

PCR reaction mixture for generating different 7α-HSDH variants
Reaction mixture

| | |
|---|---|
| Buffer (10x) | 5.0 µl |
| dNTP-Mix (10 mM) | 1.5 µl |
| Forward Primer (10 pmol/µl) | 2.0 µl |
| Reverse Primer (10 pmol/µl) | 2.0 µl |
| Template | 1.0 µl |
| Pfu Polymerase | 0.5 µl |
| DMSO | 2.5 µl |
| ddH$_2$O | 35.5 µl |
| | 50.0 µl |

As template, a pET28a vector with the corresponding wildtype gene was applied. In particular, the N6-adenine-methylated double-stranded plasmid DNA of the gene to be mutated was applied. N6-adenine-methylated plasmid DNA was isolated from the dam$^+$ E. coli strain as, for example, the strain E. coli DH5α.

The PCR was performed as described above. The PCR was performed as described above. Afterwards, the PCR product was purified by means of the PCR purification kit of Analytik Jena. Parental N6-adenine-methylated DNA was digested by means of the restriction enzyme dpnI. This enzyme has the specific feature that it restricts non-specifically N6-adenine-methylated DNA. However, it does not react with newly formed non-methylated DNA. The restriction was performed by adding 1 µl dpnI to the purified PCR reaction product for at least 2 hours or overnight at 37° C.

8 µl of said reaction mixture were applied for the transformation of 100 µl of chemically competent DH5a cells.

1.11. Expression of Individual Genes as Well as of the Whole Cell Biocatalyst

E. coli BL21(DE3)Δ7α-HSDH was transformed with the expression construct. For this purpose, the E. coli BL21 (DE3)Δ7α-HSDH strain containing the expression construct was cultivated in LB medium in the presence of the corresponding antibiotic (50 µg/ml kanamycin for pET28a, 36 µ/ml chloramphenicol for pACYCDuet or 40 µg/ml kanamycin+29 µg/ml chloramphenicol for the whole cell biocatalyst) (see E. coli DB 06 and DB07 above.

Cultivation of the cells was performed overnight in LB medium at 37° C. From this culture, a expression culture (1% volume of the overnight culture) was inoculated and at an OD$_{600}$ of about 0.6-0.8 gene expression was induced by addition of 0.5 mM IPTG. Afterwards, the cells were grown for 20 hours at 25° C. until harvested. The cells were harvested by centrifugation (10.000×g, 30 min, 4° C.). The protein concentration was determined as described above.

1.12. HPLC Analyses: Method and Condition

Bile acids and the resulting biotransformation products were analyzed by normal phase RP-HPLC (HPLC-System LC-2010AHT, Shimadzu) using a gradient of acetonitrile/water (adjusted to pH 2.6 with phosphoric acid).

The gradient is:
0-15 min constant 40% acetonitrile,
15-17 min linear increasing to 90% acetonitrile,
17-27 min constant 90% acetonitrile,
27-29 min linear increasing to 40% acetonitrile,
29-35 min constant 40% acetonitrile.

A Purospher STAR® column RP-18 endcapped (Merck, Darmstadt, Germany) served as a stationary phase and 20 µl of diluted (with 90% v/v methanol) samples were loaded onto the column.

The flow rate was maintained at 1 mL min$^{-1}$ and elutes were detected by the UV-detector at a wavelength of 200 nm.

Retention times: UDCA: 8.0 min; 7-KLCA: 11.7 min; CDCA: 17.5 min

Figure 11:
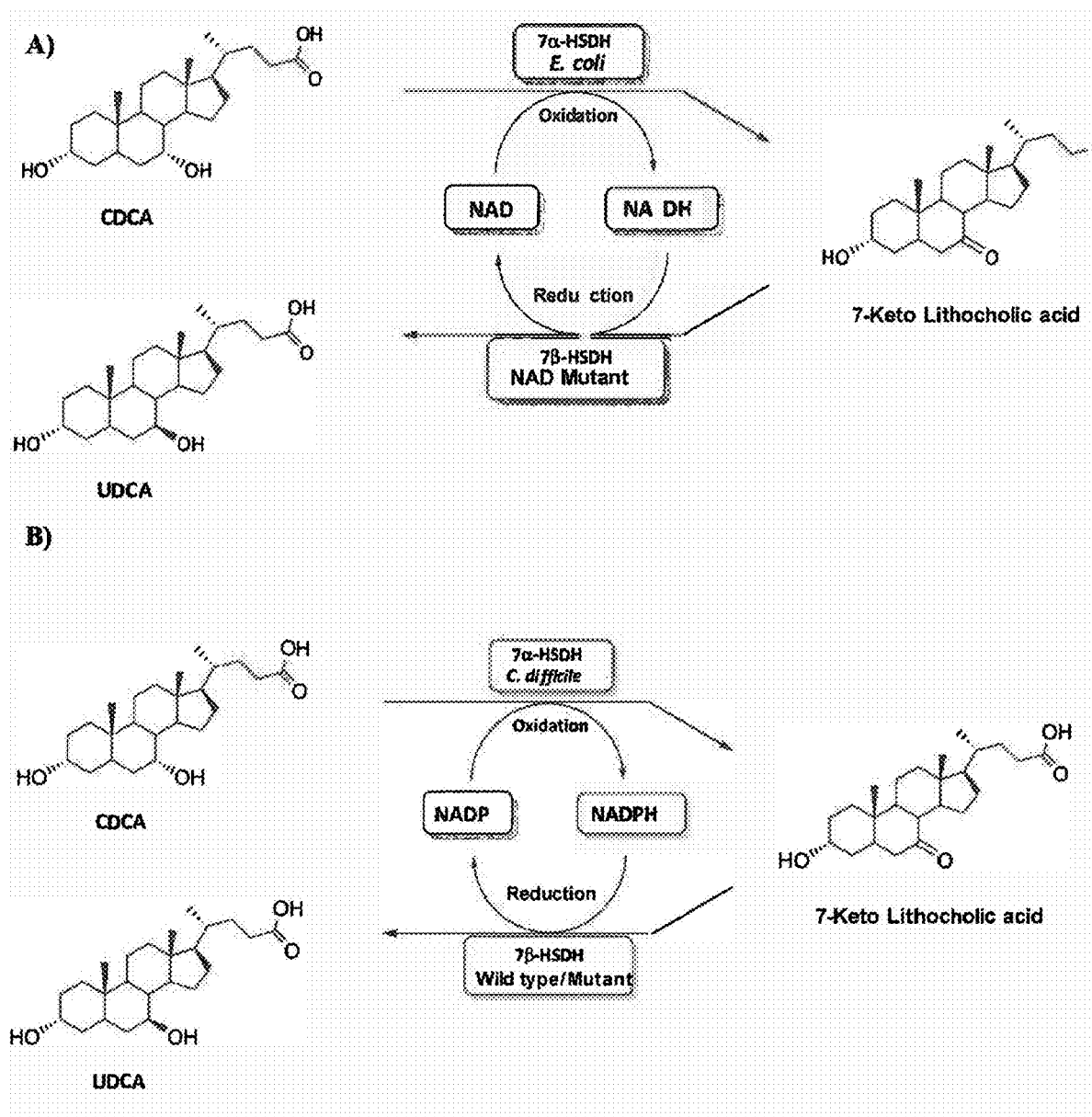
FIG. 11: Reaction scheme for the biotransformation of CDCA to UDCA in a one-step process. Both enzymes have to use the same cofactor. Figure A illustrates the reaction variant based on NAD(H) as coenzyme, while Figure B illustrates the NADP(H)-based variant.

2. Experimental Results of Example III 2.1 Reaction Principle of the One-Step Biotransformation of CDCA Two couples systems as depicted in FIG. 11 have been established. CDCA is oxidized to 7-KLCA with a 7α-HSDH and 7-KCLA is then reduced with a 7β-HSDH to UDCA under cofactor regeneration. FIG. 11A illustrates the reaction variant based on NAD(H) as coenzyme, while FIG. 11B illustrates the NADP(H)-based variant. The coupled process was performed with isolated enzymes or with whole cells, expressing the required HSDH enzymes.

2.2 Synthesis of UDCA by Means of Isolated Enzymes

The enzymatic synthesis of UDCA with isolated enzymes was performed standardized in 100 mM KPi buffer (pH 7.0) at 25° C. The reaction mixtures were magnetically stirred at 500 to 700 rpm. The cofactor concentration was 0.25 mM $NAD^+$. For the biotransformation with $NAD^+$ as cofactor, the reaction was performed with 1 J/ml enzyme, and for the biotransformation with $NADP^+$ as cofactor the reaction was performed with 0.5 U/ml 7α-HSDH and 1.0 U/ml 7β-HSDH. After pre-determined time intervals, samples were taken and analyzed by means of HPLC.

Figure 12:
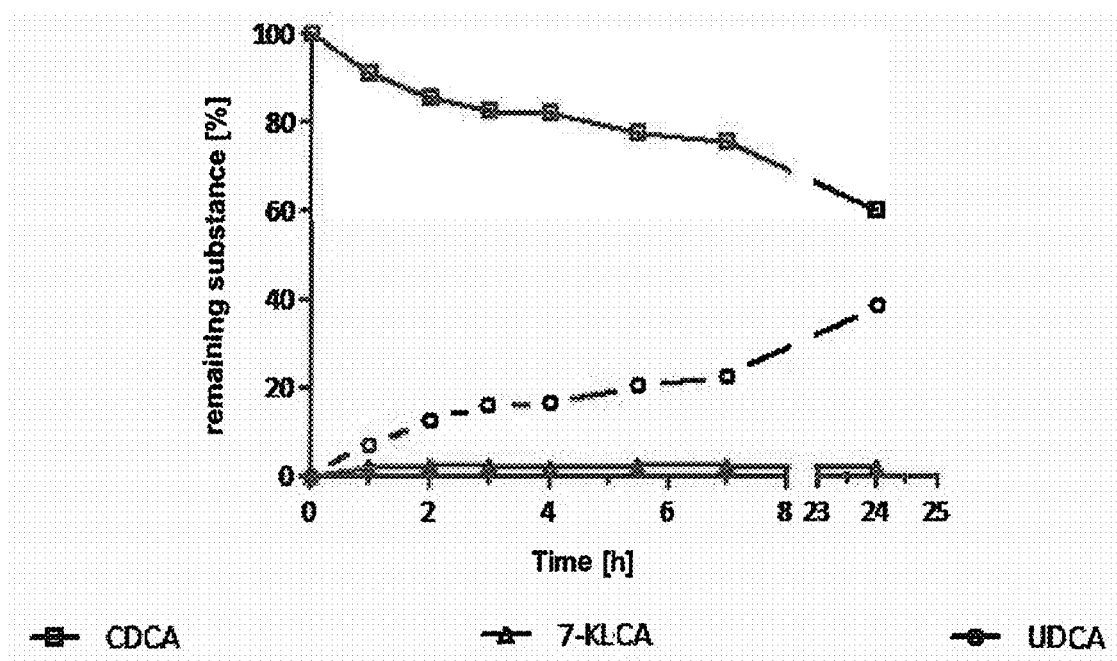
FIG. 12: Conversion of CDCA with NAD-dependent 7β-HSDH [G39E] and a 7α-HSDH from *E. coli* in a one-step process.

In a first experiment a conversion of 25 mM CDCA was performed in 100 mM KPi buffer pH 7.0 at 25° C. with NAD(H)-dependent 7β-HSDH [G39E] (SEQ ID NO:48) (for the 7-KLCA reduction) and a 7α-HSDH from E. coli (Wild type SEQ ID NO:37) (for the CDCA oxidation) in a coupled one-step process. The cofactor concentration was 0.25 mM $NAD^+$. The results are shown in FIG. 12. As illustrated a one-step conversion of CDCA in a directly coupled oxidation and reduction reaction with a $NAD^+$-dependent 7β-HSDH is operable.

Figure 13:
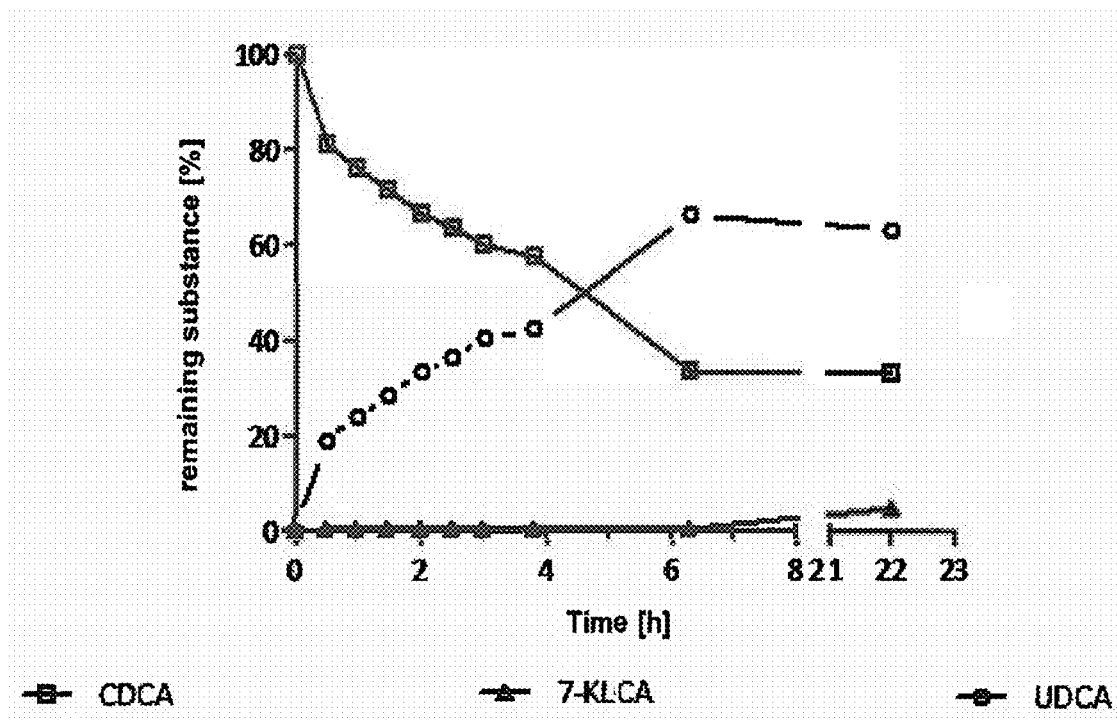
FIG. 13: Conversion of CDCA with the 7β-HSDH [G39S/R64E] and the CD7α-HSDH from *C. difficile* in a one-step process.

In a second experiment, the biotransformation was performed in a one-step process with NADP(H) as cofactor. The enzymatic conversion of 10 mM CDCA was performed in 100 mM KPi buffer pH 6.0 at 25° C. with the 7β-HSDH [G39S/R64E] (SEQ ID NO:45) and the Cd7α-HSDH from C. difficile (SEQ ID NO:35) in a one-step process. The cofactor concentration was 0.5 mM $NADP^+$. The results are shown in FIG. 13. For the 7-KLCA reduction, a $NADP^-$-dependent 7β-HSDH from C. aerofaciens was applied and for the CDCA oxidation step the 7α-HSDH from C. difficile was applied. As illustrated a one-step conversion of CDCA in a directly coupled oxidation and reduction reaction with a $NADP^+$-dependent 7β-HSDH is operable.

2.3 UDCA Synthesis by Means of a Recombinant Whole Cell Catalyst Expressing NADP-dependent 7β-HSDH and 7α-HSDH Enzymes The synthesis of UDCA by means of 5 mg/ml cells (CWW=cell wet weight) was performed standardized in 100 mM KPi buffer (pH 6.0) at 25° C. The reaction mixtures were magnetically stirred at 700 rpm. The reaction mixtures contained 0.5 mM $NADP^+$ as cofactor. After predetermined time intervals, samples were taken and analyzed by means of HPLC.

The following whole cell catalysts have been applied:

E. coli DB06 (pET28a_CD7α(N)+pA_7β-HSDH [G39S/R64E])
  expressing the $NADP^+$ dependent wildtype 7α-HSDH from C. difficile(SEQ ID NO:35) and a $NADP^+$ dependent 7β-HSDH double mutant [G39S/R64E] from C. aerofaciens (SEQ ID NO:44).

and

E. coli DB07 (pET28a_7α-HSDH(N) [D42G/I43R]+pA_7β-HSDH [G39S/R64E])
  expressing the $NADP^+$ dependent 7α-HSDH double mutant [D42G/I43R] from E. coli (SEQ ID NO:41). and a $NADP^+$ dependent 7β-HSDH double mutant [G39S/R64E] from C. aerofaciens. (SEQ ID NO:44).

Figure 14:
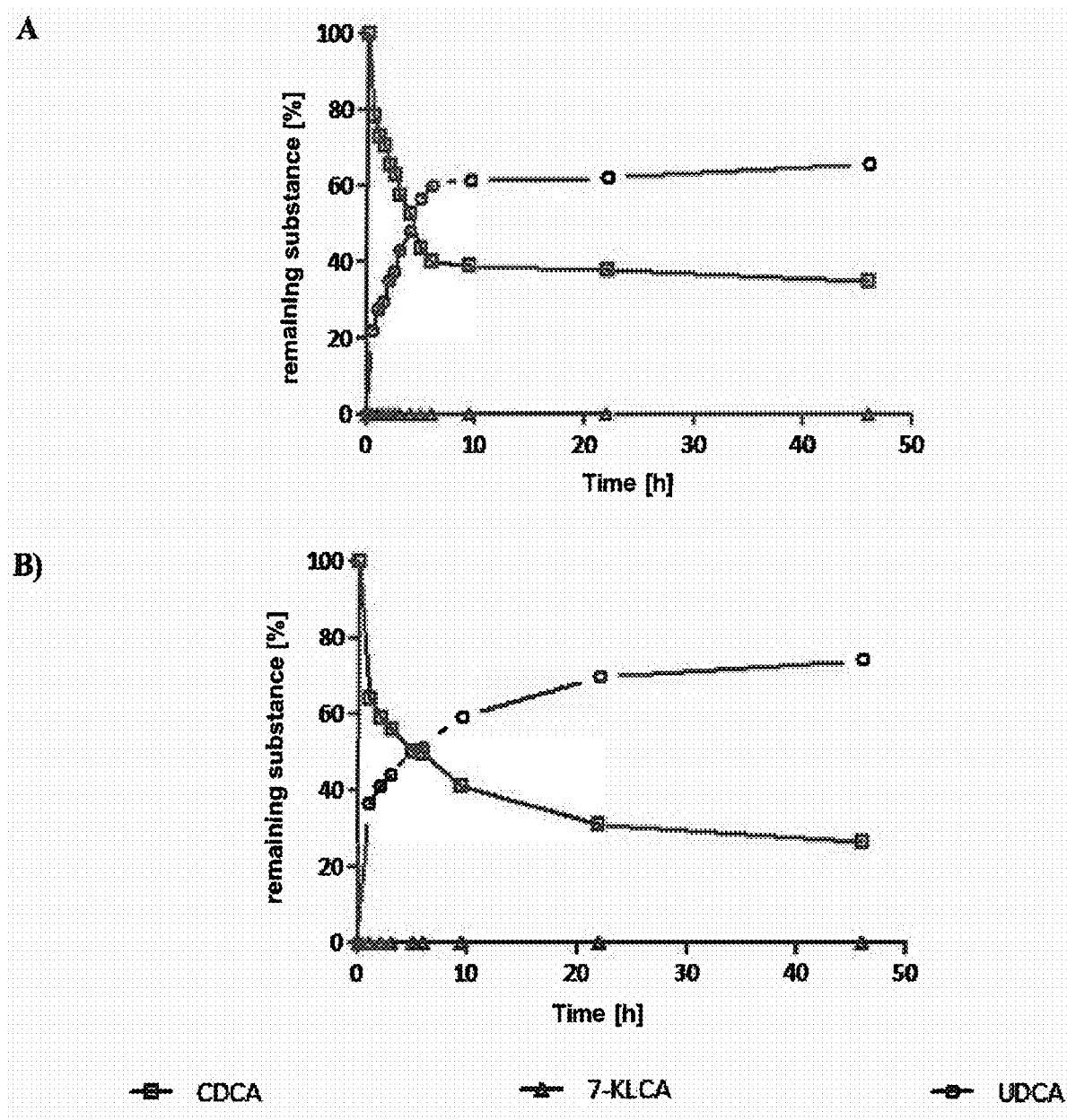
FIG. 14: Conversion of CDCA with the whole cell catalyst *E. coli* DB06 (Figure A) and *E. coli* DB07 (Figure B) in a one-step process.

Prior to use, the cells were frozen for at least one time for permeabilization. FIG. 14 shows the results of corresponding conversions of 25 mM CDCA in 100 mM $KP_i$ buffer pH 6.0 at 25° C. with the whole cell catalyst E. coli DB06 (Figure A) and E. coli DB07 (Figure B). The cofactor concentration was 0.5 mM $NADP^+$ and the reaction time was 48 hours.

Assignment of SEQ ID NOs:

| SEQ ID NO: | Description | Type |
|---|---|---|
| 1 | PCR primer | NS |
| 2 | PCR primer | NS |
| 3 | PCR primer | NS |
| 4 | PCR primer | NS |
| 5 | K16A for, PCR primer | NS |
| 6 | K16A rev, PCR primer | NS |
| 7 | K16G for, PCR primer | NS |
| 8 | K16G rev, PCR primer | NS |
| 9 | K16D for, PCR primer | NS |
| 10 | K16D rev, PCR primer | NS |
| 11 | A37E for, PCR primer | NS |
| 12 | A37E rev, PCR primer | NS |
| 13 | A37D for, PCR primer | NS |
| 14 | A37D rev, PCR primer | NS |
| 15 | A37D/R38I for, PCR primer | NS |
| 16 | A37D/R38I rev, PCR primer | NS |
| 17 | A37D/R38L for, PCR primer | NS |
| 18 | A37D/R38L rev, PCR primer | NS |
| 19 | D42G/I43R_for, PCR primer | NS |
| 20 | D42G/I43R_rev, PCR primer | NS |
| 21 | D42A/I43R_for, PCR primer | NS |
| 22 | D42A/I43R_rev, PCR primer | NS |
| 23 | D42G_for, PCR primer | NS |
| 24 | D42G_rev, PCR primer | NS |
| 25 | I43R _for, PCR primer | NS |
| 26 | I43R_rev, PCR primer | NS |
| 27 | G39S_for, PCR primer | NS |
| 28 | G39S_rev, PCR primer | NS |
| 29 | G39E_for, PCR primer | NS |
| 30 | G39E_rev, PCR primer | NS |
| 31 | R64E_for, PCR primer | NS |
| 32 | R64E_rev, PCR primer | NS |
| 33 | 7α-HSDH C. difficile WT | NS |
| 34 | 7α-HSDH C. difficile WT | AS |
| 35 | 7α-HSDH C. difficile (N-His-Tag) | AS |
| 36 | 7α-HSDH E.coli WT | NS |
| 37 | 7α-HSDH E.coli WT | AS |
| 38 | 7α-HSDH E.coli (N-His-Tag) | AS |
| 39 | 7α-HSDH E.coli [D42G/I43R] | NS |
| 40 | 7α-HSDH E.coli [D42G/I43R] | AS |
| 41 | 7α-HSDH E.coli [D42G/I43R] (N-His-Tag) | AS |
| 42 | 7α-HSDH E.coli [D42G/I43R] (C-His-Tag) | AS |
| 43 | 7β-HSDH C. aerofaciens [G395/R64E] | NS |
| 44 | 7β-HSDH C. aerofaciens [G395/R64E] | AS |
| 45 | 7β-HSDH C. aerofaciens [G395/R64E] (C-His-Tag) | AS |
| 46 | 7β-HSDH C. aerofaciens [G39E] | NS |
| 47 | 7β-HSDH C. aerofaciens [G39E] | AS |
| 48 | 7β-HSDH C. aerofaciens [G39E] (C-His-Tag) | AS |
| 49 | NAD(P)H Oxidase L, sanfrancisis | NS |
| 50 | NAD(P)H Oxidase L, sanfrancisis | AS |
| 51 | NAD(P)H Oxidase L, sanfrancisis (C-His-Tag) | AS |
| 52 | 7β-HSDH C. aerofaciens (C-His-Tag) | AS |
| 53 | 7β-HSDH C. aerofaciens WT | NS |
| 54 | 7β-HSDH C. aerofaciens WT | AS |
| 55 | 7β-HSDH R. gnavus WT | NS |
| 56 | 7β-HSDH R. gnavus WT | AS |

AS = amino acid sequence
NS = nucleic acid sequence
WT = wild type

Reference is made expressly to the disclosure of the documents mentioned herein.

The invention claimed is:

1. A mutant of *Clostridium difficile* 7α-hydroxysteroid dehydrogenase (7α-HSDH) of SEQ ID NO: 34, wherein the mutant catalyzes at least the stereospecific enzymatic oxidation of 7α-hydroxysteroids to the corresponding 7-ketosteroids under consumption of NAD$^+$ as cofactor, wherein the mutant comprises a mutation of at least one amino acid position of SEQ ID NO: 34 selected from the group consisting of K16, A37 and R38, wherein said mutation is selected from the group consisting of single mutation K16X$_1$, single mutation A37X$_2$, single mutation R38X$_3$, double mutation K16X$_1$/A37X$_2$ and double mutation A37X$_2$/R38X$_3$, wherein X$_1$ represents A, G, or D X$_2$ represents D or E and X$_3$ represents I, and wherein the amino acid sequence of the mutant has an amino acid sequence identity of at least 90% to the amino acid sequence of SEQ ID NO: 34.

2. The mutant of claim 1, when compared to 7α-HSDH of SEQ ID NO: 34 under the same conditions, shows a feature selected from the group consisting of:
   a) an increased specific activity (V$_{max}$ [U/mg]) for chenodeoxycholic acid (CDCA);
   b) an increased specific activity (V$_{max}$ [U/mg]) for NAD$^+$ during the enzymatic oxidation of CDCA with NAD$^+$ as co-factor;
   c) a modified co-factor specificity with regard to NADH and NADPH; and
   d) a reduced or missing substrate inhibition for at least one bile acid, selected from the group consisting of cholic acid (CA), CDCA and 7-ketolithocholic acid (7-KLCA);
   wherein features a) to d) may be present individually or in any combination.

3. A nucleic acid comprising a nucleotide sequence encoding the 7α-HSDH according to claim 1.

4. An expression cassette comprising at least one regulatory sequence and at least one nucleic acid of claim 3.

5. A vector comprising at least one expression cassette of claim 4.

6. A recombinant microorganism comprising at least one nucleic acid of claim 3.

7. The recombinant microorganism of claim 6, further comprising a nucleic acid encoding a 7β-HSDH that utilizes the cofactor system $NAD^+$/NADH.

8. A biocatalytic process for the enzymatic or microbial production of a 7α-ketosteroid, comprising contacting a 7α-hydroxysteroid with the mutant of claim 1 or the recombinant microorganism of claim 6 to thereby produce a 7α-ketosteroid.

9. The process of claim 8, wherein said 7α-hydroxysteroid is selected from the group consisting of cholic acid (CA), chenodeoxycholic acid (CDCA), and 12-keto-chenodeoxycholic acid (12-keto-CDCA), and salts, amides and alkyl esters of CA, CDCA, and 12-keto-CDCA.

10. The process of claim 8, wherein the contacting is performed in the presence of $NAD^+$ or $NADP^+$.

11. The process of claim 10, wherein any $NAD^+$ or $NADP^+$ consumed during the process is regenerated by coupling with an $NAD^+$ or $NADP^+$-regenerating enzyme, wherein said enzyme is selected from the group consisting of 7β-HSDHs, alcohol dehydrogenases (ADH), formate dehydrogenases (FDH), glucose dehydrogenase (GDH), NADH-dehydrogenases, alcohol dehydrogenases (ADH), glucose-6-phosphate-dehydrogenases (G6PDH) and phosphite dehydrogenases (PtDH).

12. A recombinant microorganism comprising at least one expression cassette according to claim 4.

13. A recombinant microorganism comprising at least one expression vector according to claim 5.

14. The recombinant microorganism of claim 12 or 13, further comprising a nucleic acid encoding a 7β-HSDH that utilizes the cofactor system $NAD^+$/NADH.

15. The process of claim 8, further comprising isolating the 7α-ketosteroid.

* * * * *

UNITED STATES PATENT AND TRADEMARK OFFICE
CERTIFICATE OF CORRECTION

| | |
|---|---|
| PATENT NO. | : 11,634,743 B2 |
| APPLICATION NO. | : 16/309580 |
| DATED | : April 25, 2023 |
| INVENTOR(S) | : Bakonyi et al. |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 776 days.

Signed and Sealed this
Twelfth Day of November, 2024

Katherine Kelly Vidal
*Director of the United States Patent and Trademark Office*

```
                         SEQUENCE LISTING

<160> NUMBER OF SEQ ID NOS: 64

<210> SEQ ID NO 1
<211> LENGTH: 33
<212> TYPE: DNA
<213> ORGANISM: Artificial Sequence
<220> FEATURE:
<223> OTHER INFORMATION: PCR Primer

<400> SEQUENCE: 1
ccgccgcata tggaaaaatt acaaggaaaa att                            33

<210> SEQ ID NO 2
<211> LENGTH: 37
<212> TYPE: DNA
<213> ORGANISM: Artificial Sequence
<220> FEATURE:
<223> OTHER INFORMATION: PCR Primer

<400> SEQUENCE: 2
cgcctagcgg ccgcttatcc taattatcct aatatat                        37

<210> SEQ ID NO 3
<211> LENGTH: 32
<212> TYPE: DNA
<213> ORGANISM: Artificial Sequence
<220> FEATURE:
<223> OTHER INFORMATION: PCR Primer

<400> SEQUENCE: 3
aaccaaccat gggaatgaaa gttattgtag ta                             32

<210> SEQ ID NO 4
<211> LENGTH: 28
<212> TYPE: DNA
<213> ORGANISM: Artificial Sequence
<220> FEATURE:
<223> OTHER INFORMATION: PCR Primer

<400> SEQUENCE: 4
ataataactc gagcgtatag tttaagac                                  28

<210> SEQ ID NO 5
<211> LENGTH: 48
<212> TYPE: DNA
<213> ORGANISM: Artificial Sequence
<220> FEATURE:
<223> OTHER INFORMATION: PCR Primer

<400> SEQUENCE: 5
aaattgcagt agttactgca gcaacagcag gtattggatt agcatcag             48

<210> SEQ ID NO 6
<211> LENGTH: 48
<212> TYPE: DNA
<213> ORGANISM: Artificial Sequence
<220> FEATURE:
<223> OTHER INFORMATION: PCR Primer

<400> SEQUENCE: 6
ctgatgctaa tccaatacct gctgttgctg cagtaactac tgcaattt             48

<210> SEQ ID NO 7
```

```
<211> LENGTH: 48
<212> TYPE: DNA
<213> ORGANISM: Artificial Sequence
<220> FEATURE:
<223> OTHER INFORMATION: PCR Primer

<400> SEQUENCE: 7
aaattgcagt agttactgca gcaacaggag gtattggatt agcatcag                48

<210> SEQ ID NO 8
<211> LENGTH: 48
<212> TYPE: DNA
<213> ORGANISM: Artificial Sequence
<220> FEATURE:
<223> OTHER INFORMATION: PCR Primer

<400> SEQUENCE: 8
ctgatgctaa tccaatacct cctgttgctg cagtaactac tgcaattt                48

<210> SEQ ID NO 9
<211> LENGTH: 45
<212> TYPE: DNA
<213> ORGANISM: Artificial Sequence
<220> FEATURE:
<223> OTHER INFORMATION: PCR Primer

<400> SEQUENCE: 9
ttgcagtagt tactgcagca acagatggta ttggattagc atcag                   45

<210> SEQ ID NO 10
<211> LENGTH: 45
<212> TYPE: DNA
<213> ORGANISM: Artificial Sequence
<220> FEATURE:
<223> OTHER INFORMATION: PCR Primer

<400> SEQUENCE: 10
ctgatgctaa tccaatacca tctgttgctg cagtaactac tgcaa                   45

<210> SEQ ID NO 11
<211> LENGTH: 44
<212> TYPE: DNA
<213> ORGANISM: Artificial Sequence
<220> FEATURE:
<223> OTHER INFORMATION: PCR Primer

<400> SEQUENCE: 11
gagcaactgt gtacttagca gagcgttcag aagaattagc tcat                    44

<210> SEQ ID NO 12
<211> LENGTH: 44
<212> TYPE: DNA
<213> ORGANISM: Artificial Sequence
<220> FEATURE:
<223> OTHER INFORMATION: PCR Primer

<400> SEQUENCE: 12
atgagctaat tcttctgaac gctctgctaa gtacacagtt gctc                    44

<210> SEQ ID NO 13
<211> LENGTH: 39
<212> TYPE: DNA
<213> ORGANISM: Artificial Sequence
<220> FEATURE:
<223> OTHER INFORMATION: PCR Primer
```

<400> SEQUENCE: 13
gcaactgtgt acttagcaga tcgttcagaa gaattagct                      39

<210> SEQ ID NO 14
<211> LENGTH: 39
<212> TYPE: DNA
<213> ORGANISM: Artificial Sequence
<220> FEATURE:
<223> OTHER INFORMATION: PCR Primer

<400> SEQUENCE: 14
agctaattct tctgaacgat ctgctaagta cacagttgc                      39

<210> SEQ ID NO 15
<211> LENGTH: 54
<212> TYPE: DNA
<213> ORGANISM: Artificial Sequence
<220> FEATURE:
<223> OTHER INFORMATION: PCR Primer

<400> SEQUENCE: 15
aaatggagca actgtgtact tagcagatat ttcagaagaa ttagctcatg aagt     54

<210> SEQ ID NO 16
<211> LENGTH: 56
<212> TYPE: DNA
<213> ORGANISM: Artificial Sequence
<220> FEATURE:
<223> OTHER INFORMATION: PCR Primer

<400> SEQUENCE: 16
taacttcatg agctaattct tctgaaatat ctgctaagta cacagttgct ccattt   56

<210> SEQ ID NO 17
<211> LENGTH: 46
<212> TYPE: DNA
<213> ORGANISM: Artificial Sequence
<220> FEATURE:
<223> OTHER INFORMATION: PCR Primer

<400> SEQUENCE: 17
gagcaactgt gtacttagca gatctttcag aagaattagc tcatga             46

<210> SEQ ID NO 18
<211> LENGTH: 46
<212> TYPE: DNA
<213> ORGANISM: Artificial Sequence
<220> FEATURE:
<223> OTHER INFORMATION: PCR Primer

<400> SEQUENCE: 18
tcatgagcta attcttctga aagatctgct aagtacacag ttgctc              46

<210> SEQ ID NO 19
<211> LENGTH: 41
<212> TYPE: DNA
<213> ORGANISM: Artificial Sequence
<220> FEATURE:
<223> OTHER INFORMATION: PCR Primer

<400> SEQUENCE: 19
catctgtggt ggtcagtggt aggaacgccg acgcagctaa c                   41

<210> SEQ ID NO 20

-continued

```
<211> LENGTH: 41
<212> TYPE: DNA
<213> ORGANISM: Artificial Sequence
<220> FEATURE:
<223> OTHER INFORMATION: PCR Primer

<400> SEQUENCE: 20
gttagctgcg tcggcgttcc taccactgac caccacagat g          41

<210> SEQ ID NO 21
<211> LENGTH: 41
<212> TYPE: DNA
<213> ORGANISM: Artificial Sequence
<220> FEATURE:
<223> OTHER INFORMATION: PCR Primer

<400> SEQUENCE: 21
catctgtggt ggtcagtgct aggaacgccg acgcagctaa c          41

<210> SEQ ID NO 22
<211> LENGTH: 41
<212> TYPE: DNA
<213> ORGANISM: Artificial Sequence
<220> FEATURE:
<223> OTHER INFORMATION: PCR Primer

<400> SEQUENCE: 22
gttagctgcg tcggcgttcc tagcactgac caccacagat g          41

<210> SEQ ID NO 23
<211> LENGTH: 27
<212> TYPE: DNA
<213> ORGANISM: Artificial Sequence
<220> FEATURE:
<223> OTHER INFORMATION: PCR Primer

<400> SEQUENCE: 23
gtggtggtca gtggtattaa cgccgac                          27

<210> SEQ ID NO 24
<211> LENGTH: 28
<212> TYPE: DNA
<213> ORGANISM: Artificial Sequence
<220> FEATURE:
<223> OTHER INFORMATION: PCR Primer

<400> SEQUENCE: 24
gtcggcgtta ataccaactg accaccac                         28

<210> SEQ ID NO 25
<211> LENGTH: 36
<212> TYPE: DNA
<213> ORGANISM: Artificial Sequence
<220> FEATURE:
<223> OTHER INFORMATION: PCR Primer

<400> SEQUENCE: 25
gcatctgtgg tggtcagtga taggaacgcc gacgca                36

<210> SEQ ID NO 26
<211> LENGTH: 36
<212> TYPE: DNA
<213> ORGANISM: Artificial Sequence
<220> FEATURE:
<223> OTHER INFORMATION: PCR Primer
```

```
<400> SEQUENCE: 26
tgcgtcggcg ttcctatcac tgaccaccac agatgc                                36

<210> SEQ ID NO 27
<211> LENGTH: 27
<212> TYPE: DNA
<213> ORGANISM: Artificial Sequence
<220> FEATURE:
<223> OTHER INFORMATION: PCR Primer

<400> SEQUENCE: 27
gtcgtcatgg tcagccgtcg cgaggag                                          27

<210> SEQ ID NO 28
<211> LENGTH: 27
<212> TYPE: DNA
<213> ORGANISM: Artificial Sequence
<220> FEATURE:
<223> OTHER INFORMATION: PCR Primer

<400> SEQUENCE: 28
ctcctcgcga cggctgacca tgacgac                                          27

<210> SEQ ID NO 29
<211> LENGTH: 27
<212> TYPE: DNA
<213> ORGANISM: Artificial Sequence
<220> FEATURE:
<223> OTHER INFORMATION: PCR Primer

<400> SEQUENCE: 29
gtcgtcatgg tcgagcgtcg cgaggag                                          27

<210> SEQ ID NO 30
<211> LENGTH: 27
<212> TYPE: DNA
<213> ORGANISM: Artificial Sequence
<220> FEATURE:
<223> OTHER INFORMATION: PCR Primer

<400> SEQUENCE: 30
ctcctcgcga cgctcgacca tgacgac                                          27

<210> SEQ ID NO 31
<211> LENGTH: 27
<212> TYPE: DNA
<213> ORGANISM: Artificial Sequence
<220> FEATURE:
<223> OTHER INFORMATION: PCR Primer

<400> SEQUENCE: 31
accaaggtcg tggaggccga ctttagc                                          27

<210> SEQ ID NO 32
<211> LENGTH: 27
<212> TYPE: DNA
<213> ORGANISM: Artificial Sequence
<220> FEATURE:
<223> OTHER INFORMATION: PCR Primer

<400> SEQUENCE: 32
gctaaagtcg gcctccacga ccttggt                                          27

<210> SEQ ID NO 33
```

-continued

```
<211> LENGTH: 789
<212> TYPE: DNA
<213> ORGANISM: Clostridium difficile

<400> SEQUENCE: 33
atggaaaaat tacaaggaaa aattgcagta gttactgcag caacaaaagg tattggatta      60
gcatcagcag agatattagc aaaaaatgga gcaactgtgt acttagcagc tcgttcagaa     120
gaattagctc atgaagttat aaataaaata agtgcagaag gtggttgtgc taagtttgtt     180
tactttaatg ctcgtgaaga agagaccttt acctcaatga tagaagaggt agttaaaaaa     240
gaaggtaaga tagatatact tgtaaacaat tttggttcaa caaccccttc tcttgacaaa     300
gaccttgtaa ctggggatac agataatttc tttgacacag taaatactaa tttaaaaagt     360
gtgtatttac catgtaaagc agcaattcct catatgataa agaatggaaa aggaagtata     420
gtaaatatat caagtatagg ttcagtatta cctgatttat ctagaatagc ttactgtgta     480
tcaaaagcag caatcaactc attaactcaa aacatagcta cacaatatgc taaagacaat     540
gttagatgta atgctgtact tccagggctt attgcaacta agcagcatt agacaatatg     600 tctccagagt tcataaaaga atttttaaag catgttcctt taaatcgtat agggggaacca     660 gatgatatag caaaagctgt tctattctat gctagtgatg actcatcatt tataacaggg     720
gatttacttg aagttgcagg aggatttggt ttacctactc cacaatttgc agataatata     780
ttaggataa                                                               789

<210> SEQ ID NO 34
<211> LENGTH: 262
<212> TYPE: PRT
<213> ORGANISM: Clostridium difficile

<400> SEQUENCE: 34
```

Met Glu Lys Leu Gln Gly Lys Ile Ala Val Val Thr Ala Ala Thr Lys
1               5                   10                  15

Gly Ile Gly Leu Ala Ser Ala Glu Ile Leu Ala Lys Asn Gly Ala Thr
            20                  25                  30

Val Tyr Leu Ala Ala Arg Ser Glu Glu Leu Ala His Glu Val Ile Asn
        35                  40                  45

Lys Ile Ser Ala Glu Gly Gly Cys Ala Lys Phe Val Tyr Phe Asn Ala
    50                  55                  60

Arg Glu Glu Glu Thr Phe Thr Ser Met Ile Glu Glu Val Val Lys Lys
65                  70                  75                  80

Glu Gly Lys Ile Asp Ile Leu Val Asn Asn Phe Gly Ser Thr Asn Pro
                85                  90                  95

Ser Leu Asp Lys Asp Leu Val Thr Gly Asp Thr Asp Asn Phe Phe Asp
            100                 105                 110

Thr Val Asn Thr Asn Leu Lys Ser Val Tyr Leu Pro Cys Lys Ala Ala
        115                 120                 125

Ile Pro His Met Ile Lys Asn Gly Lys Gly Ser Ile Val Asn Ile Ser
    130                 135                 140

Ser Ile Gly Ser Val Leu Pro Asp Leu Ser Arg Ile Ala Tyr Cys Val
145                 150                 155                 160

Ser Lys Ala Ala Ile Asn Ser Leu Thr Gln Asn Ile Ala Thr Gln Tyr
                165                 170                 175

Ala Lys Asp Asn Val Arg Cys Asn Ala Val Leu Pro Gly Leu Ile Ala
            180                 185                 190

```
Thr Lys Ala Ala Leu Asp Asn Met Ser Pro Glu Phe Ile Lys Glu Phe
        195                 200                 205

Leu Lys His Val Pro Leu Asn Arg Ile Gly Glu Pro Asp Asp Ile Ala
    210                 215                 220

Lys Ala Val Leu Phe Tyr Ala Ser Asp Ser Ser Phe Ile Thr Gly
225                 230                 235                 240

Asp Leu Leu Glu Val Ala Gly Gly Phe Gly Leu Pro Thr Pro Gln Phe
                245                 250                 255

Ala Asp Asn Ile Leu Gly
            260

<210> SEQ ID NO 35
<211> LENGTH: 282
<212> TYPE: PRT
<213> ORGANISM: Artificial Sequence
<220> FEATURE:
<223> OTHER INFORMATION: 7alpha HSDH C. difficile + N-terminal HisTag

<400> SEQUENCE: 35

Met Gly Ser Ser His His His His His His Ser Ser Gly Leu Val Pro
1               5                   10                  15

Arg Gly Ser His Met Glu Lys Leu Gln Gly Lys Ile Ala Val Val Thr
                20                  25                  30

Ala Ala Thr Lys Gly Ile Gly Leu Ala Ser Ala Glu Ile Leu Ala Lys
            35                  40                  45

Asn Gly Ala Thr Val Tyr Leu Ala Ala Arg Ser Glu Glu Leu Ala His
    50                  55                  60

Glu Val Ile Asn Lys Ile Ser Ala Glu Gly Gly Cys Ala Lys Phe Val
65                  70                  75                  80

Tyr Phe Asn Ala Arg Glu Glu Thr Phe Thr Ser Met Ile Glu Glu
                85                  90                  95

Val Val Lys Lys Glu Gly Lys Ile Asp Ile Leu Val Asn Asn Phe Gly
                100                 105                 110

Ser Thr Asn Pro Ser Leu Asp Lys Asp Leu Val Thr Gly Asp Thr Asp
            115                 120                 125

Asn Phe Phe Asp Thr Val Asn Thr Asn Leu Lys Ser Val Tyr Leu Pro
    130                 135                 140

Cys Lys Ala Ala Ile Pro His Met Ile Lys Asn Gly Lys Gly Ser Ile
145                 150                 155                 160

Val Asn Ile Ser Ser Ile Gly Ser Val Leu Pro Asp Leu Ser Arg Ile
                165                 170                 175

Ala Tyr Cys Val Ser Lys Ala Ala Ile Asn Ser Leu Thr Gln Asn Ile
            180                 185                 190

Ala Thr Gln Tyr Ala Lys Asp Asn Val Arg Cys Asn Ala Val Leu Pro
    195                 200                 205

Gly Leu Ile Ala Thr Lys Ala Ala Leu Asp Asn Met Ser Pro Glu Phe
    210                 215                 220

Ile Lys Glu Phe Leu Lys His Val Pro Leu Asn Arg Ile Gly Glu Pro
225                 230                 235                 240

Asp Asp Ile Ala Lys Ala Val Leu Phe Tyr Ala Ser Asp Asp Ser Ser
                245                 250                 255

Phe Ile Thr Gly Asp Leu Leu Glu Val Ala Gly Gly Phe Gly Leu Pro
            260                 265                 270

Thr Pro Gln Phe Ala Asp Asn Ile Leu Gly
    275                 280
```

<210> SEQ ID NO 36
<211> LENGTH: 768
<212> TYPE: DNA
<213> ORGANISM: Escherichia coli

<400> SEQUENCE: 36

```
atgtttaatt ctgacaacct gagactcgac ggaaaatgcg ccatcatcac aggtgcgggt      60
gcaggtattg gtaaagaaat cgccattaca ttcgcgacag ctggcgcatc tgtggtggtc     120
agtgatatta acgccgacgc agctaaccat gttgtagacg aaattcaaca actgggtggt     180
caggcatttg cctgccgttg tgatattact tccgaacagg aactctctgc actggcagac     240
tttgctatca gtaagctggg taaagttgat attctggtta caacgccgg tggcggtgga      300
cctaaaccgt tgatatgcc aatggcggat tttcgccgtg cttatgaact gaatgtgttt      360
tctttttcc atctgtcaca acttgttgcg ccagaaatgg aaaaaaatgg cggtggcgtt      420
attctgacca tcacttctat ggcggcagaa aataaaaata taaacatgac ttcctatgca     480
tcatctaaag ctgcggccag tcatctggtc agaaatatgg cgtttgacct gggtgaaaaa     540
aatattcggg taaatggcat tgcgccgggg gcaatattaa ccgatgccct gaaatccgtt     600
attacaccag aaattgaaca aaaaatgtta cagcacacgc cgatcagacg tctgggccaa     660
ccgcaagata ttgctaacgc agcgctgttc ctttgctcgc ctgctgcgag ctgggtaagc     720
ggacaaattc tcaccgtctc cggtggtggg gtacaggagc tcaattaa                 768
```

<210> SEQ ID NO 37
<211> LENGTH: 255
<212> TYPE: PRT
<213> ORGANISM: Escherichia coli

<400> SEQUENCE: 37

```
Met Phe Asn Ser Asp Asn Leu Arg Leu Asp Gly Lys Cys Ala Ile Ile
1               5                   10                  15

Thr Gly Ala Gly Ala Gly Ile Gly Lys Glu Ile Ala Ile Thr Phe Ala
            20                  25                  30

Thr Ala Gly Ala Ser Val Val Ser Asp Ile Asn Ala Asp Ala Ala
        35                  40                  45

Asn His Val Val Asp Glu Ile Gln Gln Leu Gly Gly Gln Ala Phe Ala
    50                  55                  60

Cys Arg Cys Asp Ile Thr Ser Glu Gln Glu Leu Ser Ala Leu Ala Asp
65                  70                  75                  80

Phe Ala Ile Ser Lys Leu Gly Lys Val Asp Ile Leu Val Asn Asn Ala
                85                  90                  95

Gly Gly Gly Gly Pro Lys Pro Phe Asp Met Pro Met Ala Asp Phe Arg
            100                 105                 110

Arg Ala Tyr Glu Leu Asn Val Phe Ser Phe Phe His Leu Ser Gln Leu
        115                 120                 125

Val Ala Pro Glu Met Glu Lys Asn Gly Gly Gly Val Ile Leu Thr Ile
    130                 135                 140

Thr Ser Met Ala Ala Glu Asn Lys Asn Ile Asn Met Thr Ser Tyr Ala
145                 150                 155                 160

Ser Ser Lys Ala Ala Ala Ser His Leu Val Arg Asn Met Ala Phe Asp
                165                 170                 175

Leu Gly Glu Lys Asn Ile Arg Val Asn Gly Ile Ala Pro Gly Ala Ile
            180                 185                 190
```

-continued

Leu Thr Asp Ala Leu Lys Ser Val Ile Thr Pro Glu Ile Glu Gln Lys
            195                 200                 205

Met Leu Gln His Thr Pro Ile Arg Arg Leu Gly Gln Pro Gln Asp Ile
    210                 215                 220

Ala Asn Ala Ala Leu Phe Leu Cys Ser Pro Ala Ala Ser Trp Val Ser
225                 230                 235                 240

Gly Gln Ile Leu Thr Val Ser Gly Gly Val Gln Glu Leu Asn
                245                 250                 255

<210> SEQ ID NO 38
<211> LENGTH: 275
<212> TYPE: PRT
<213> ORGANISM: Artificial Sequence
<220> FEATURE:
<223> OTHER INFORMATION: E. coli  7alpha  HSDH WT + N-terminal His Tag

<400> SEQUENCE: 38

Met Gly Ser Ser His His His His His His Ser Ser Gly Leu Val Pro
1               5                   10                  15

Arg Gly Ser His Met Phe Asn Ser Asp Asn Leu Arg Leu Asp Gly Lys
            20                  25                  30

Cys Ala Ile Ile Thr Gly Ala Gly Ala Gly Ile Gly Lys Glu Ile Ala
        35                  40                  45

Ile Thr Phe Ala Thr Ala Gly Ala Ser Val Val Val Ser Asp Ile Asn
    50                  55                  60

Ala Asp Ala Ala Asn His Val Val Asp Glu Ile Gln Gln Leu Gly Gly
65                  70                  75                  80

Gln Ala Phe Ala Cys Arg Cys Asp Ile Thr Ser Glu Gln Glu Leu Ser
                85                  90                  95

Ala Leu Ala Asp Phe Ala Ile Ser Lys Leu Gly Lys Val Asp Ile Leu
            100                 105                 110

Val Asn Asn Ala Gly Gly Gly Gly Pro Lys Pro Phe Asp Met Pro Met
        115                 120                 125

Ala Asp Phe Arg Arg Ala Tyr Glu Leu Asn Val Phe Ser Phe Phe His
    130                 135                 140

Leu Ser Gln Leu Val Ala Pro Glu Met Glu Lys Asn Gly Gly Gly Val
145                 150                 155                 160

Ile Leu Thr Ile Thr Ser Met Ala Ala Glu Asn Lys Asn Ile Asn Met
                165                 170                 175

Thr Ser Tyr Ala Ser Ser Lys Ala Ala Ala Ser His Leu Val Arg Asn
            180                 185                 190

Met Ala Phe Asp Leu Gly Glu Lys Asn Ile Arg Val Asn Gly Ile Ala
    195                 200                 205

Pro Gly Ala Ile Leu Thr Asp Ala Leu Lys Ser Val Ile Thr Pro Glu
210                 215                 220

Ile Glu Gln Lys Met Leu Gln His Thr Pro Ile Arg Arg Leu Gly Gln
225                 230                 235                 240

Pro Gln Asp Ile Ala Asn Ala Ala Leu Phe Leu Cys Ser Pro Ala Ala
                245                 250                 255

Ser Trp Val Ser Gly Gln Ile Leu Thr Val Ser Gly Gly Val Gln
            260                 265                 270

Glu Leu Asn
        275

<210> SEQ ID NO 39
<211> LENGTH: 768

```
<212> TYPE: DNA
<213> ORGANISM: Artificial Sequence
<220> FEATURE:
<223> OTHER INFORMATION: 7alpha HSDH E. coli mutant D42G/I43R

<400> SEQUENCE: 39
atgtttaatt ctgacaacct gagactcgac ggaaaatgcg ccatcatcac aggtgcgggt       60
gcaggtattg gtaaagaaat cgccattaca ttcgcgacag ctggcgcatc tgtggtggtc      120
agtgatatta cgccgacgc agctaaccat gttgtagacg aaattcaaca actgggtggt      180
caggcatttg cctgccgttg tgatattact ccgaacagg aactctctgc actggcagac      240
tttgctatca gtaagctggg taagttgat attctggtta caacgccgg tggcggtgga      300 cctaaaccgt tgatatgcc aatggcggat tttcgccgtg cttatgaact gaatgtgttt      360
tcttttttcc atctgtcaca acttgttgcg ccagaaatgg aaaaaatgg cggtggcgtt      420 attctgacca tcacttctat ggcggcagaa aataaaaata taaacatgac ttcctatgca      480
tcatctaaag ctgcggccag tcatctggtc agaaatatgg cgtttgacct gggtgaaaaa      540
aatattcggg taaatggcat tgcgccgggg gcaatattaa ccgatgccct gaaatccgtt      600
attacaccag aaattgaaca aaaaatgtta cagcacacgc cgatcagacg tctgggccaa      660
ccgcaagata ttgctaacgc agcgctgttc ctttgctcgc ctgctgcgag ctgggtaagc      720
ggacaaattc tcaccgtctc cggtggtggg gtacaggagc tcaattaa                  768

<210> SEQ ID NO 40
<211> LENGTH: 255
<212> TYPE: PRT
<213> ORGANISM: Artificial Sequence
<220> FEATURE:
<223> OTHER INFORMATION: Synthetic Construct

<400> SEQUENCE: 40

Met Phe Asn Ser Asp Asn Leu Arg Leu Asp Gly Lys Cys Ala Ile Ile
1               5                   10                  15

Thr Gly Ala Gly Ala Gly Ile Gly Lys Glu Ile Ala Ile Thr Phe Ala
                20                  25                  30

Thr Ala Gly Ala Ser Val Val Ser Asp Ile Asn Ala Asp Ala Ala
            35                  40                  45

Asn His Val Val Asp Glu Ile Gln Gln Leu Gly Gly Gln Ala Phe Ala
        50                  55                  60

Cys Arg Cys Asp Ile Thr Ser Glu Gln Glu Leu Ser Ala Leu Ala Asp
65                  70                  75                  80

Phe Ala Ile Ser Lys Leu Gly Lys Val Asp Ile Leu Val Asn Asn Ala
                85                  90                  95

Gly Gly Gly Gly Pro Lys Pro Phe Asp Met Pro Met Ala Asp Phe Arg
            100                 105                 110

Arg Ala Tyr Glu Leu Asn Val Phe Ser Phe Phe His Leu Ser Gln Leu
        115                 120                 125

Val Ala Pro Glu Met Glu Lys Asn Gly Gly Gly Val Ile Leu Thr Ile
    130                 135                 140

Thr Ser Met Ala Ala Glu Asn Lys Asn Ile Asn Met Thr Ser Tyr Ala
145                 150                 155                 160

Ser Ser Lys Ala Ala Ala Ser His Leu Val Arg Asn Met Ala Phe Asp
                165                 170                 175

Leu Gly Glu Lys Asn Ile Arg Val Asn Gly Ile Ala Pro Gly Ala Ile
            180                 185                 190
```

Leu Thr Asp Ala Leu Lys Ser Val Ile Thr Pro Glu Ile Glu Gln Lys
            195                 200                 205

Met Leu Gln His Thr Pro Ile Arg Arg Leu Gly Gln Pro Gln Asp Ile
    210                 215                 220

Ala Asn Ala Ala Leu Phe Leu Cys Ser Pro Ala Ala Ser Trp Val Ser
225                 230                 235                 240

Gly Gln Ile Leu Thr Val Ser Gly Gly Val Gln Glu Leu Asn
                245                 250                 255

<210> SEQ ID NO 41
<211> LENGTH: 275
<212> TYPE: PRT
<213> ORGANISM: Artificial Sequence
<220> FEATURE:
<223> OTHER INFORMATION: 7alpha HSDH E. coli mutant D42G/I43R +
      N-terminal His-Tag

<400> SEQUENCE: 41

Met Gly Ser Ser His His His His His His Ser Ser Gly Leu Val Pro
1               5                   10                  15

Arg Gly Ser His Met Phe Asn Ser Asp Asn Leu Arg Leu Asp Gly Lys
            20                  25                  30

Cys Ala Ile Ile Thr Gly Ala Gly Ala Gly Ile Gly Lys Glu Ile Ala
        35                  40                  45

Ile Thr Phe Ala Thr Ala Gly Ala Ser Val Val Val Ser Gly Arg Asn
 50                  55                  60

Ala Asp Ala Ala Asn His Val Val Asp Glu Ile Gln Gln Leu Gly Gly
65                  70                  75                  80

Gln Ala Phe Ala Cys Arg Cys Asp Ile Thr Ser Glu Gln Glu Leu Ser
                85                  90                  95

Ala Leu Ala Asp Phe Ala Ile Ser Lys Leu Gly Lys Val Asp Ile Leu
            100                 105                 110

Val Asn Asn Ala Gly Gly Gly Gly Pro Lys Pro Phe Asp Met Pro Met
        115                 120                 125

Ala Asp Phe Arg Arg Ala Tyr Glu Leu Asn Val Phe Ser Phe Phe His
130                 135                 140

Leu Ser Gln Leu Val Ala Pro Glu Met Glu Lys Asn Gly Gly Gly Val
145                 150                 155                 160

Ile Leu Thr Ile Thr Ser Met Ala Ala Glu Asn Lys Asn Ile Asn Met
                165                 170                 175

Thr Ser Tyr Ala Ser Ser Lys Ala Ala Ala Ser His Leu Val Arg Asn
            180                 185                 190

Met Ala Phe Asp Leu Gly Glu Lys Asn Ile Arg Val Asn Gly Ile Ala
        195                 200                 205

Pro Gly Ala Ile Leu Thr Asp Ala Leu Lys Ser Val Ile Thr Pro Glu
    210                 215                 220

Ile Glu Gln Lys Met Leu Gln His Thr Pro Ile Arg Arg Leu Gly Gln
225                 230                 235                 240

Pro Gln Asp Ile Ala Asn Ala Ala Leu Phe Leu Cys Ser Pro Ala Ala
                245                 250                 255

Ser Trp Val Ser Gly Gln Ile Leu Thr Val Ser Gly Gly Val Gln
            260                 265                 270

Glu Leu Asn
    275

<210> SEQ ID NO 42

<211> LENGTH: 263
<212> TYPE: PRT
<213> ORGANISM: Artificial Sequence
<220> FEATURE:
<223> OTHER INFORMATION: 7alpha HSDH E. coli mutant D42G/I43R + C-terminal His-Tag

<400> SEQUENCE: 42

```
Met Phe Asn Ser Asp Asn Leu Arg Leu Asp Gly Lys Cys Ala Ile Ile
1               5                   10                  15
Thr Gly Ala Gly Ala Gly Ile Gly Lys Glu Ile Ala Ile Thr Phe Ala
            20                  25                  30
Thr Ala Gly Ala Ser Val Val Ser Gly Arg Asn Ala Asp Ala Ala
        35                  40                  45
Asn His Val Val Asp Glu Ile Gln Gln Leu Gly Gly Gln Ala Phe Ala
    50                  55                  60
Cys Arg Cys Asp Ile Thr Ser Glu Gln Glu Leu Ser Ala Leu Ala Asp
65                  70                  75                  80
Phe Ala Ile Ser Lys Leu Gly Lys Val Asp Ile Leu Val Asn Asn Ala
                85                  90                  95
Gly Gly Gly Gly Pro Lys Pro Phe Asp Met Pro Met Ala Asp Phe Arg
            100                 105                 110
Arg Ala Tyr Glu Leu Asn Val Phe Ser Phe Phe His Leu Ser Gln Leu
        115                 120                 125
Val Ala Pro Glu Met Glu Lys Asn Gly Gly Gly Val Ile Leu Thr Ile
    130                 135                 140
Thr Ser Met Ala Ala Glu Asn Lys Asn Ile Asn Met Thr Ser Tyr Ala
145                 150                 155                 160
Ser Ser Lys Ala Ala Ala Ser His Leu Val Arg Asn Met Ala Phe Asp
                165                 170                 175
Leu Gly Glu Lys Asn Ile Arg Val Asn Gly Ile Ala Pro Gly Ala Ile
            180                 185                 190
Leu Thr Asp Ala Leu Lys Ser Val Ile Thr Pro Glu Ile Glu Gln Lys
        195                 200                 205
Met Leu Gln His Thr Pro Ile Arg Arg Leu Gly Gln Pro Gln Asp Ile
    210                 215                 220
Ala Asn Ala Ala Leu Phe Leu Cys Ser Pro Ala Ala Ser Trp Val Ser
225                 230                 235                 240
Gly Gln Ile Leu Thr Val Ser Gly Gly Val Gln Glu Leu Asn Leu
                245                 250                 255
Glu His His His His His
            260
```

<210> SEQ ID NO 43
<211> LENGTH: 792
<212> TYPE: DNA
<213> ORGANISM: Artificial Sequence
<220> FEATURE:
<223> OTHER INFORMATION: 7beta-HSDH Mutant [G39S/R64E] C. aerofaciensi

<400> SEQUENCE: 43

```
atgaacctga gggagaagta cggtgagtgg ggcctgatcc tgggcgcgac cgagggcgtc      60
ggcaaggcgt tctgcgagaa gatcgccgcc ggcggcatga acgtcgtcat ggtcagccgt     120
cgcgaggaga agctgaacgt gctcgcaggc gagatccgcg agacctacgg cgtggagacc     180
aaggtcgtgg aggccgactt tagccagccc ggcgctgccg agaccgtctt cgccgcgacc     240
gagggcctgg acatgggctt catgagctac gtggcctgcc tgcacagctt cggtaagatc     300
```

```
caggacaccc cctgggagaa gcacgaggcc atgatcaacg tcaacgtcgt gaccttcctc    360
aagtgcttcc accactacat gcggatcttt gccgcccagg accgcggcgc cgtgatcaac    420
gtctcgtcga tgaccggcat cagctccagc ccctggaacg gccagtacgg cgcgggcaag    480
gccttcatcc tcaagatgac cgaggccgtg gcctgcgagt gcgagggcac cggcgtcgac    540
gtcgaggtca tcaccctcgg caccacccta accccagcc tgctgtccaa cctccccggc    600
ggcccgcagg gcgaggccgt catgaagatc gccctcaccc cgaggagtg cgttgacgag    660 gcctttgaga agctgggtaa ggagctctcc gtcatcgccg ccagcgcaa caaggactcc    720 gtccacgact ggaaggcaaa ccacaccgag gacgagtaca tccgctacat ggggtcgttc    780
taccgcgact ag                                                        792
```

<210> SEQ ID NO 44
<211> LENGTH: 263
<212> TYPE: PRT
<213> ORGANISM: Artificial Sequence
<220> FEATURE:
<223> OTHER INFORMATION: Synthetic Construct

<400> SEQUENCE: 44

```
Met Asn Leu Arg Glu Lys Tyr Gly Glu Trp Gly Leu Ile Leu Gly Ala
1               5                   10                  15

Thr Glu Gly Val Gly Lys Ala Phe Cys Glu Lys Ile Ala Ala Gly Gly
            20                  25                  30

Met Asn Val Val Met Val Ser Arg Arg Glu Glu Lys Leu Asn Val Leu
        35                  40                  45

Ala Gly Glu Ile Arg Glu Thr Tyr Gly Val Glu Thr Lys Val Val Glu
    50                  55                  60

Ala Asp Phe Ser Gln Pro Gly Ala Ala Glu Thr Val Phe Ala Ala Thr
65                  70                  75                  80

Glu Gly Leu Asp Met Gly Phe Met Ser Tyr Val Ala Cys Leu His Ser
                85                  90                  95

Phe Gly Lys Ile Gln Asp Thr Pro Trp Glu Lys His Glu Ala Met Ile
            100                 105                 110

Asn Val Asn Val Val Thr Phe Leu Lys Cys Phe His His Tyr Met Arg
        115                 120                 125

Ile Phe Ala Ala Gln Asp Arg Gly Ala Val Ile Asn Val Ser Ser Met
    130                 135                 140

Thr Gly Ile Ser Ser Ser Pro Trp Asn Gly Gln Tyr Gly Ala Gly Lys
145                 150                 155                 160

Ala Phe Ile Leu Lys Met Thr Glu Ala Val Ala Cys Glu Cys Glu Gly
                165                 170                 175

Thr Gly Val Asp Val Glu Val Ile Thr Leu Gly Thr Thr Leu Thr Pro
            180                 185                 190

Ser Leu Leu Ser Asn Leu Pro Gly Gly Pro Gln Gly Glu Ala Val Met
        195                 200                 205

Lys Ile Ala Leu Thr Pro Glu Glu Cys Val Asp Glu Ala Phe Glu Lys
    210                 215                 220

Leu Gly Lys Glu Leu Ser Val Ile Ala Gly Gln Arg Asn Lys Asp Ser
225                 230                 235                 240

Val His Asp Trp Lys Ala Asn His Thr Glu Asp Glu Tyr Ile Arg Tyr
                245                 250                 255

Met Gly Ser Phe Tyr Arg Asp
            260
```

<210> SEQ ID NO 45
<211> LENGTH: 271
<212> TYPE: PRT
<213> ORGANISM: Artificial Sequence
<220> FEATURE:
<223> OTHER INFORMATION: 7beta-HSDH Mutant [G39S/R64E] C. aerofaciens + C-terminal His-tag

<400> SEQUENCE: 45

```
Met Asn Leu Arg Glu Lys Tyr Gly Glu Trp Gly Leu Ile Leu Gly Ala
1               5                   10                  15

Thr Glu Gly Val Gly Lys Ala Phe Cys Glu Lys Ile Ala Ala Gly Gly
            20                  25                  30

Met Asn Val Val Met Val Ser Arg Arg Glu Glu Lys Leu Asn Val Leu
        35                  40                  45

Ala Gly Glu Ile Arg Glu Thr Tyr Gly Val Glu Thr Lys Val Val Glu
    50                  55                  60

Ala Asp Phe Ser Gln Pro Gly Ala Ala Glu Thr Val Phe Ala Ala Thr
65                  70                  75                  80

Glu Gly Leu Asp Met Gly Phe Met Ser Tyr Val Ala Cys Leu His Ser
                85                  90                  95

Phe Gly Lys Ile Gln Asp Thr Pro Trp Glu Lys His Glu Ala Met Ile
            100                 105                 110

Asn Val Asn Val Val Thr Phe Leu Lys Cys Phe His His Tyr Met Arg
        115                 120                 125

Ile Phe Ala Ala Gln Asp Arg Gly Ala Val Ile Asn Val Ser Ser Met
    130                 135                 140

Thr Gly Ile Ser Ser Ser Pro Trp Asn Gly Gln Tyr Gly Ala Gly Lys
145                 150                 155                 160

Ala Phe Ile Leu Lys Met Thr Glu Ala Val Ala Cys Glu Cys Glu Gly
                165                 170                 175

Thr Gly Val Asp Val Glu Val Ile Thr Leu Gly Thr Thr Leu Thr Pro
            180                 185                 190

Ser Leu Leu Ser Asn Leu Pro Gly Gly Pro Gln Gly Glu Ala Val Met
        195                 200                 205

Lys Ile Ala Leu Thr Pro Glu Glu Cys Val Asp Glu Ala Phe Glu Lys
    210                 215                 220

Leu Gly Lys Glu Leu Ser Val Ile Ala Gly Gln Arg Asn Lys Asp Ser
225                 230                 235                 240

Val His Asp Trp Lys Ala Asn His Thr Glu Asp Glu Tyr Ile Arg Tyr
                245                 250                 255

Met Gly Ser Phe Tyr Arg Asp Leu Glu His His His His His His
            260                 265                 270
```

<210> SEQ ID NO 46
<211> LENGTH: 792
<212> TYPE: DNA
<213> ORGANISM: Artificial Sequence
<220> FEATURE:
<223> OTHER INFORMATION: 7beta-HSDH Mutante [G39E] C. aerofaciens

<400> SEQUENCE: 46

```
atgaacctga gggagaagta cggtgagtgg ggcctgatcc tgggcgcgac cgagggcgtc    60
ggcaaggcgt tctgcgagaa gatcgccgcc ggcggcatga acgtcgtcat ggtcgagcgt   120
cgcgaggaga agctgaacgt gctcgcaggc gagatccgcg agacctacgg cgtggagacc   180
```

```
aaggtcgtgc gcgccgactt tagccagccc ggcgctgccg agaccgtctt cgccgcgacc    240
gagggcctgg acatgggctt catgagctac gtggcctgcc tgcacagctt cggtaagatc    300
caggacaccc cctgggagaa gcacgaggcc atgatcaacg tcaacgtcgt gaccttcctc    360
aagtgcttcc accactacat gcggatcttt gccgccagg accgcggcgc cgtgatcaac     420
gtctcgtcga tgaccggcat cagctccagc ccctggaacg gccagtacgg cgcgggcaag    480
gccttcatcc tcaagatgac cgaggccgtg gcctgcgagt gcgagggcac cggcgtcgac    540
gtcgaggtca tcaccctcgg caccacccta accccagcc tgctgtccaa cctccccggc     600
ggcccgcagg gcgaggccgt catgaagatc gccctcaccc ccgaggagtg cgttgacgag    660
gcctttgaga agctgggtaa ggagctctcc gtcatcgccg ccagcgcaa caaggactcc     720 gtccacgact ggaaggcaaa ccacaccgag gacgagtaca tccgctacat ggggtcgttc    780
taccgcgact ag                                                        792
```

<210> SEQ ID NO 47
<211> LENGTH: 263
<212> TYPE: PRT
<213> ORGANISM: Artificial Sequence
<220> FEATURE:
<223> OTHER INFORMATION: Synthetic Construct

<400> SEQUENCE: 47

```
Met Asn Leu Arg Glu Lys Tyr Gly Glu Trp Gly Leu Ile Leu Gly Ala
1               5                   10                  15

Thr Glu Gly Val Gly Lys Ala Phe Cys Glu Lys Ile Ala Ala Gly Gly
            20                  25                  30

Met Asn Val Val Met Val Glu Arg Glu Glu Lys Leu Asn Val Leu
        35                  40                  45

Ala Gly Glu Ile Arg Glu Thr Tyr Gly Val Glu Thr Lys Val Val Arg
    50                  55                  60

Ala Asp Phe Ser Gln Pro Gly Ala Ala Glu Thr Val Phe Ala Ala Thr
65                  70                  75                  80

Glu Gly Leu Asp Met Gly Phe Met Ser Tyr Val Ala Cys Leu His Ser
                85                  90                  95

Phe Gly Lys Ile Gln Asp Thr Pro Trp Glu Lys His Glu Ala Met Ile
            100                 105                 110

Asn Val Asn Val Val Thr Phe Leu Lys Cys Phe His His Tyr Met Arg
        115                 120                 125

Ile Phe Ala Ala Gln Asp Arg Gly Ala Val Ile Asn Val Ser Ser Met
    130                 135                 140

Thr Gly Ile Ser Ser Ser Pro Trp Asn Gly Gln Tyr Gly Ala Gly Lys
145                 150                 155                 160

Ala Phe Ile Leu Lys Met Thr Glu Ala Val Ala Cys Glu Cys Glu Gly
                165                 170                 175

Thr Gly Val Asp Val Glu Val Ile Thr Leu Gly Thr Thr Leu Thr Pro
            180                 185                 190

Ser Leu Leu Ser Asn Leu Pro Gly Gly Pro Gln Gly Glu Ala Val Met
        195                 200                 205

Lys Ile Ala Leu Thr Pro Glu Glu Cys Val Asp Glu Ala Phe Glu Lys
    210                 215                 220

Leu Gly Lys Glu Leu Ser Val Ile Ala Gly Gln Arg Asn Lys Asp Ser
225                 230                 235                 240

Val His Asp Trp Lys Ala Asn His Thr Glu Asp Glu Tyr Ile Arg Tyr
                245                 250                 255
```

Met Gly Ser Phe Tyr Arg Asp
            260

<210> SEQ ID NO 48
<211> LENGTH: 271
<212> TYPE: PRT
<213> ORGANISM: Artificial Sequence
<220> FEATURE:
<223> OTHER INFORMATION: 7beta-HSDH Mutante [G39E]  C. aerofaciens +
      C-terminal His-Tag

<400> SEQUENCE: 48

Met Asn Leu Arg Glu Lys Tyr Gly Glu Trp Gly Leu Ile Leu Gly Ala
1               5                   10                  15

Thr Glu Gly Val Gly Lys Ala Phe Cys Glu Lys Ile Ala Ala Gly Gly
            20                  25                  30

Met Asn Val Val Met Val Glu Arg Glu Glu Lys Leu Asn Val Leu
        35                  40                  45

Ala Gly Glu Ile Arg Glu Thr Tyr Gly Val Glu Thr Lys Val Val Arg
    50                  55                  60

Ala Asp Phe Ser Gln Pro Gly Ala Ala Glu Thr Val Phe Ala Ala Thr
65                  70                  75                  80

Glu Gly Leu Asp Met Gly Phe Met Ser Tyr Val Ala Cys Leu His Ser
                85                  90                  95

Phe Gly Lys Ile Gln Asp Thr Pro Trp Glu Lys His Glu Ala Met Ile
            100                 105                 110

Asn Val Asn Val Val Thr Phe Leu Lys Cys Phe His His Tyr Met Arg
        115                 120                 125

Ile Phe Ala Ala Gln Asp Arg Gly Ala Val Ile Asn Val Ser Ser Met
    130                 135                 140

Thr Gly Ile Ser Ser Ser Pro Trp Asn Gly Gln Tyr Gly Ala Gly Lys
145                 150                 155                 160

Ala Phe Ile Leu Lys Met Thr Glu Ala Val Ala Cys Glu Cys Glu Gly
                165                 170                 175

Thr Gly Val Asp Val Glu Val Ile Thr Leu Gly Thr Thr Leu Thr Pro
            180                 185                 190

Ser Leu Leu Ser Asn Leu Pro Gly Gly Pro Gln Gly Glu Ala Val Met
        195                 200                 205

Lys Ile Ala Leu Thr Pro Glu Glu Cys Val Asp Glu Ala Phe Glu Lys
    210                 215                 220

Leu Gly Lys Glu Leu Ser Val Ile Ala Gly Gln Arg Asn Lys Asp Ser
225                 230                 235                 240

Val His Asp Trp Lys Ala Asn His Thr Glu Asp Glu Tyr Ile Arg Tyr
                245                 250                 255

Met Gly Ser Phe Tyr Arg Asp Leu Glu His His His His His His
            260                 265                 270

<210> SEQ ID NO 49
<211> LENGTH: 1359
<212> TYPE: DNA
<213> ORGANISM: Lactobacillus sanfrancisco

<400> SEQUENCE: 49
atgaaagtta ttgtagtagg ttgtactcac gctggcactt ttgcagttaa gcaaacgatt      60
gccgatcacc ccgatgcaga tgtgactgca tatgaaatga atgataacat ttccttttta     120
tcatgtggaa tcgcccttta cttaggtaaa gaaattaaaa acaatgatcc cgagggctt      180

```
ttctactcaa gtccagaaga attaagcaat cttggagcta acgtccaaat gcgtcatcaa    240
gttacaaacg ttgatccaga acaaaaaca atcaaagtta aagatttaat caccaacgaa     300
gaaaaaacag aagcatatga caaattaatt atgaccactg gttctaagcc tactgttcct    360
ccaatccctg gaatcgatag tagtcgcgtt tacctttgta aaaactataa cgatgctaaa    420
aagttatttg aagaagctcc caaagctaaa acgattacta tcattggttc tggttatatt    480
ggtgccgaac tggctgaagc ctactcaaac caaaattata acgttaattt aattgatggt    540
catgaacgag ttctttacaa gtattttgat aaagaattta ctgatatttt agccaaagat    600
tatgaagctc atggtgttaa cctggttctt ggttcaaaag tagctgcttt tgaagaagtc    660
gatgatgaaa ttatcactaa aaccctagat ggtaaagaaa ttaaatctga tattgcaatt    720
ctttgtatcg gtttccgccc taacactgaa ttacttaaag gtaaagttgc catgttggat    780
aacggtgcaa tcattactga tgaatacatg cattcatcaa atcgcgacat ttttgctgct    840
ggtgatagtg ccgccgttca ctacaaccc  actaattcta acgcctacat tcctttagct    900
accaacgccg tacgccaagg gagattagtt ggcctaaatc tgactgaaga caaagtaaaa    960
gacatgggaa cccaatcttc atctggtctt aaactatacg gtcggactta tgtctcaact   1020
ggaatcaata cggctcttgc taaagccaat aatttaaaag ttagcgaagt aatcatagct   1080
gataattatc gtccagaatt tatgttatca acgatgaag  ttttaatgtc attagtgtat   1140
gatcctaaga ctcgtgtaat tttgggaggg gcgctttcaa gtatgcacga tgtttcgcaa   1200
tcagcgaacg tcttatcagt atgtattcaa aataaaaaca cgattgacga tttagcaatg   1260
gtggatatgt tattccaacc acaatttgat cgtccgttta ctacttaaa cattctaggc   1320 caagctgctc aagcacaagc tgacaaagca cataaataa                          1359
```

<210> SEQ ID NO 50
<211> LENGTH: 452
<212> TYPE: PRT
<213> ORGANISM: Lactobacillus sanfrancisco

<400> SEQUENCE: 50

```
Met Lys Val Ile Val Gly Cys Thr His Ala Gly Thr Phe Ala Val
1               5                   10                  15

Lys Gln Thr Ile Ala Asp His Pro Asp Ala Asp Val Thr Ala Tyr Glu
            20                  25                  30

Met Asn Asp Asn Ile Ser Phe Leu Ser Cys Gly Ile Ala Leu Tyr Leu
        35                  40                  45

Gly Lys Glu Ile Lys Asn Asn Asp Pro Arg Gly Leu Phe Tyr Ser Ser
    50                  55                  60

Pro Glu Glu Leu Ser Asn Leu Gly Ala Asn Val Gln Met Arg His Gln
65                  70                  75                  80

Val Thr Asn Val Asp Pro Glu Thr Lys Thr Ile Lys Val Lys Asp Leu
                85                  90                  95

Ile Thr Asn Glu Glu Lys Thr Glu Ala Tyr Asp Lys Leu Ile Met Thr
            100                 105                 110

Thr Gly Ser Lys Pro Thr Val Pro Pro Ile Pro Gly Ile Asp Ser Ser
        115                 120                 125

Arg Val Tyr Leu Cys Lys Asn Tyr Asn Asp Ala Lys Lys Leu Phe Glu
    130                 135                 140

Glu Ala Pro Lys Ala Lys Thr Ile Thr Ile Ile Gly Ser Gly Tyr Ile
145                 150                 155                 160
```

```
Gly Ala Glu Leu Ala Glu Ala Tyr Ser Asn Gln Asn Tyr Asn Val Asn
            165                 170                 175

Leu Ile Asp Gly His Glu Arg Val Leu Tyr Lys Tyr Phe Asp Lys Glu
        180                 185                 190

Phe Thr Asp Ile Leu Ala Lys Asp Tyr Glu Ala His Gly Val Asn Leu
        195                 200                 205

Val Leu Gly Ser Lys Val Ala Ala Phe Glu Glu Val Asp Asp Glu Ile
        210                 215                 220

Ile Thr Lys Thr Leu Asp Gly Lys Glu Ile Ser Asp Ile Ala Ile
225                 230                 235                 240

Leu Cys Ile Gly Phe Arg Pro Asn Thr Glu Leu Leu Lys Gly Lys Val
                245                 250                 255

Ala Met Leu Asp Asn Gly Ala Ile Ile Thr Asp Glu Tyr Met His Ser
            260                 265                 270

Ser Asn Arg Asp Ile Phe Ala Ala Gly Asp Ser Ala Ala Val His Tyr
        275                 280                 285

Asn Pro Thr Asn Ser Asn Ala Tyr Ile Pro Leu Ala Thr Asn Ala Val
        290                 295                 300

Arg Gln Gly Arg Leu Val Gly Leu Asn Leu Thr Glu Asp Lys Val Lys
305                 310                 315                 320

Asp Met Gly Thr Gln Ser Ser Gly Leu Lys Leu Tyr Gly Arg Thr
                325                 330                 335

Tyr Val Ser Thr Gly Ile Asn Thr Ala Leu Ala Lys Ala Asn Asn Leu
            340                 345                 350

Lys Val Ser Glu Val Ile Ala Asp Asn Tyr Arg Pro Glu Phe Met
        355                 360                 365

Leu Ser Thr Asp Glu Val Leu Met Ser Leu Val Tyr Asp Pro Lys Thr
        370                 375                 380

Arg Val Ile Leu Gly Gly Ala Leu Ser Ser Met His Asp Val Ser Gln
385                 390                 395                 400

Ser Ala Asn Val Leu Ser Val Cys Ile Gln Asn Lys Asn Thr Ile Asp
                405                 410                 415

Asp Leu Ala Met Val Asp Met Leu Phe Gln Pro Gln Phe Asp Arg Pro
            420                 425                 430

Phe Asn Tyr Leu Asn Ile Leu Gly Gln Ala Gln Ala Gln Ala Asp
        435                 440                 445

Lys Ala His Lys
    450

<210> SEQ ID NO 51
<211> LENGTH: 460
<212> TYPE: PRT
<213> ORGANISM: Artificial Sequence
<220> FEATURE:
<223> OTHER INFORMATION: NAD(P)H Oxidase + C-terminal His-Tag

<400> SEQUENCE: 51

Met Lys Val Ile Val Val Gly Cys Thr His Ala Gly Thr Phe Ala Val
1               5                   10                  15

Lys Gln Thr Ile Ala Asp His Pro Asp Ala Asp Val Thr Ala Tyr Glu
            20                  25                  30

Met Asn Asp Asn Ile Ser Phe Leu Ser Cys Gly Ile Ala Leu Tyr Leu
        35                  40                  45

Gly Lys Glu Ile Lys Asn Asn Asp Pro Arg Gly Leu Phe Tyr Ser Ser
    50                  55                  60
```

-continued

Pro Glu Glu Leu Ser Asn Leu Gly Ala Asn Val Gln Met Arg His Gln
65                  70                  75                  80

Val Thr Asn Val Asp Pro Glu Thr Lys Thr Ile Lys Val Lys Asp Leu
                85                  90                  95

Ile Thr Asn Glu Glu Lys Thr Glu Ala Tyr Asp Lys Leu Ile Met Thr
            100                 105                 110

Thr Gly Ser Lys Pro Thr Val Pro Pro Ile Pro Gly Ile Asp Ser Ser
        115                 120                 125

Arg Val Tyr Leu Cys Lys Asn Tyr Asn Asp Ala Lys Lys Leu Phe Glu
    130                 135                 140

Glu Ala Pro Lys Ala Lys Thr Ile Thr Ile Ile Gly Ser Gly Tyr Ile
145                 150                 155                 160

Gly Ala Glu Leu Ala Glu Ala Tyr Ser Asn Gln Asn Tyr Asn Val Asn
                165                 170                 175

Leu Ile Asp Gly His Glu Arg Val Leu Tyr Lys Tyr Phe Asp Lys Glu
            180                 185                 190

Phe Thr Asp Ile Leu Ala Lys Asp Tyr Glu Ala His Gly Val Asn Leu
        195                 200                 205

Val Leu Gly Ser Lys Val Ala Ala Phe Glu Glu Val Asp Asp Glu Ile
210                 215                 220

Ile Thr Lys Thr Leu Asp Gly Lys Glu Ile Lys Ser Asp Ile Ala Ile
225                 230                 235                 240

Leu Cys Ile Gly Phe Arg Pro Asn Thr Glu Leu Leu Lys Gly Lys Val
                245                 250                 255

Ala Met Leu Asp Asn Gly Ala Ile Ile Thr Asp Glu Tyr Met His Ser
                260                 265                 270

Ser Asn Arg Asp Ile Phe Ala Ala Gly Asp Ser Ala Ala Val His Tyr
            275                 280                 285

Asn Pro Thr Asn Ser Asn Ala Tyr Ile Pro Leu Ala Thr Asn Ala Val
        290                 295                 300

Arg Gln Gly Arg Leu Val Gly Leu Asn Leu Thr Glu Asp Lys Val Lys
305                 310                 315                 320

Asp Met Gly Thr Gln Ser Ser Ser Gly Leu Lys Leu Tyr Gly Arg Thr
                325                 330                 335

Tyr Val Ser Thr Gly Ile Asn Thr Ala Leu Ala Lys Ala Asn Asn Leu
            340                 345                 350

Lys Val Ser Glu Val Ile Ile Ala Asp Asn Tyr Arg Pro Glu Phe Met
        355                 360                 365

Leu Ser Thr Asp Glu Val Leu Met Ser Leu Val Tyr Asp Pro Lys Thr
    370                 375                 380

Arg Val Ile Leu Gly Gly Ala Leu Ser Ser Met His Asp Val Ser Gln
385                 390                 395                 400

Ser Ala Asn Val Leu Ser Val Cys Ile Gln Asn Lys Asn Thr Ile Asp
                405                 410                 415

Asp Leu Ala Met Val Asp Met Leu Phe Gln Pro Gln Phe Asp Arg Pro
            420                 425                 430

Phe Asn Tyr Leu Asn Ile Leu Gly Gln Ala Ala Gln Ala Gln Ala Asp
        435                 440                 445

Lys Ala His Lys Leu Glu His His His His His
    450                 455                 460

<210> SEQ ID NO 52
<211> LENGTH: 271
<212> TYPE: PRT

<213> ORGANISM: Artificial Sequence
<220> FEATURE:
<223> OTHER INFORMATION: 7beta-HSDH C. aerofaciens + C-terminal His-tag

<400> SEQUENCE: 52

```
Met Asn Leu Arg Glu Lys Tyr Gly Glu Trp Gly Leu Ile Leu Gly Ala
1               5                   10                  15

Thr Glu Gly Val Gly Lys Ala Phe Cys Glu Lys Ile Ala Ala Gly Gly
            20                  25                  30

Met Asn Val Val Met Val Gly Arg Arg Glu Glu Lys Leu Asn Val Leu
        35                  40                  45

Ala Gly Glu Ile Arg Glu Thr Tyr Gly Val Thr Lys Val Val Arg
    50                  55                  60

Ala Asp Phe Ser Gln Pro Gly Ala Ala Glu Thr Val Phe Ala Ala Thr
65                  70                  75                  80

Glu Gly Leu Asp Met Gly Phe Met Ser Tyr Val Ala Cys Leu His Ser
                85                  90                  95

Phe Gly Lys Ile Gln Asp Thr Pro Trp Glu Lys His Glu Ala Met Ile
                100                 105                 110

Asn Val Asn Val Val Thr Phe Leu Lys Cys Phe His His Tyr Met Arg
            115                 120                 125

Ile Phe Ala Ala Gln Asp Arg Gly Ala Val Ile Asn Val Ser Ser Met
        130                 135                 140

Thr Gly Ile Ser Ser Ser Pro Trp Asn Gly Gln Tyr Gly Ala Gly Lys
145                 150                 155                 160

Ala Phe Ile Leu Lys Met Thr Glu Ala Val Ala Cys Glu Cys Glu Gly
                165                 170                 175

Thr Gly Val Asp Val Glu Val Ile Thr Leu Gly Thr Thr Leu Thr Pro
            180                 185                 190

Ser Leu Leu Ser Asn Leu Pro Gly Gly Pro Gln Gly Glu Ala Val Met
        195                 200                 205

Lys Ile Ala Leu Thr Pro Glu Glu Cys Val Asp Glu Ala Phe Glu Lys
    210                 215                 220

Leu Gly Lys Glu Leu Ser Val Ile Ala Gly Gln Arg Asn Lys Asp Ser
225                 230                 235                 240

Val His Asp Trp Lys Ala Asn His Thr Glu Asp Glu Tyr Ile Arg Tyr
                245                 250                 255

Met Gly Ser Phe Tyr Arg Asp Leu Glu His His His His His His
            260                 265                 270
```

<210> SEQ ID NO 53
<211> LENGTH: 792
<212> TYPE: DNA
<213> ORGANISM: Colinsella aerofaciens

<400> SEQUENCE: 53

```
atgaacctga gggagaagta cggtgagtgg ggcctgatcc tgggcgcgac cgagggcgtc    60
ggcaaggcgt tctgcgagaa gatcgccgcc ggcggcatga acgtcgtcat ggtcggccgt   120
cgcgaggaga agctgaacgt gctcgcaggc gagatccgcg agacctacgg cgtggagacc   180
aaggtcgtgc gcgccgactt tagccagccc ggcgctgccg agaccgtctt cgccgcgacc   240
gagggcctgg acatgggctt catgagctac gtggcctgcc tgcacagctt cggtaagatc   300
caggacaccc cctgggagaa gcacgaggcc atgatcaacg tcaacgtcgt gaccttcctc   360
aagtgcttcc accactacat gcggatcttt gccgcccagg accgcggcgc cgtgatcaac   420
```

```
gtctcgtcga tgaccggcat cagctccagc ccctggaacg gccagtacgg cgcgggcaag    480
gccttcatcc tcaagatgac cgaggccgtg gcctgcgagt gcgagggcac cggcgtcgac    540
gtcgaggtca tcaccctcgg caccacccta accccagcc tgctgtccaa cctccccggc    600
ggcccgcagg gcgaggccgt catgaagatc gccctcaccc ccgaggagtg cgttgacgag    660
gcctttgaga agctgggtaa ggagctctcc gtcatcgccg gccagcgcaa caaggactcc    720
gtccacgact ggaaggcaaa ccacaccgag gacgagtaca tccgctacat ggggtcgttc    780
taccgcgact ag                                                        792
```

<210> SEQ ID NO 54
<211> LENGTH: 263
<212> TYPE: PRT
<213> ORGANISM: Colinsella aerofaciens

<400> SEQUENCE: 54

Met Asn Leu Arg Glu Lys Tyr Gly Glu Trp Gly Leu Ile Leu Gly Ala
1               5                   10                  15

Thr Glu Gly Val Gly Lys Ala Phe Cys Glu Lys Ile Ala Ala Gly Gly
            20                  25                  30

Met Asn Val Val Met Val Gly Arg Arg Glu Glu Lys Leu Asn Val Leu
        35                  40                  45

Ala Gly Glu Ile Arg Glu Thr Tyr Gly Val Gly Thr Lys Val Val Arg
    50                  55                  60

Ala Asp Phe Ser Gln Pro Gly Ala Ala Glu Thr Val Phe Ala Ala Thr
65                  70                  75                  80

Glu Gly Leu Asp Met Gly Phe Met Ser Tyr Val Ala Cys Leu His Ser
                85                  90                  95

Phe Gly Lys Ile Gln Asp Thr Pro Trp Glu Lys His Glu Ala Met Ile
            100                 105                 110

Asn Val Asn Val Val Thr Phe Leu Lys Cys Phe His His Tyr Met Arg
        115                 120                 125

Ile Phe Ala Ala Gln Asp Arg Gly Ala Val Ile Asn Val Ser Ser Met
    130                 135                 140

Thr Gly Ile Ser Ser Pro Trp Asn Gly Gln Tyr Gly Ala Gly Lys
145                 150                 155                 160

Ala Phe Ile Leu Lys Met Thr Glu Ala Val Ala Cys Glu Cys Glu Gly
                165                 170                 175

Thr Gly Val Asp Val Glu Val Ile Thr Leu Gly Thr Thr Leu Thr Pro
            180                 185                 190

Ser Leu Leu Ser Asn Leu Pro Gly Gly Pro Gln Gly Glu Ala Val Met
        195                 200                 205

Lys Ile Ala Leu Thr Pro Glu Glu Cys Val Asp Glu Ala Phe Glu Lys
    210                 215                 220

Leu Gly Lys Glu Leu Ser Val Ile Ala Gly Gln Arg Asn Lys Asp Ser
225                 230                 235                 240

Val His Asp Trp Lys Ala Asn His Thr Glu Asp Glu Tyr Ile Arg Tyr
                245                 250                 255

Met Gly Ser Phe Tyr Arg Asp
            260

<210> SEQ ID NO 55
<211> LENGTH: 792
<212> TYPE: DNA
<213> ORGANISM: Ruminococcus gnavus

<400> SEQUENCE: 55

```
atgacattga gagaaaaata tggagaatgg ggaattattt taggcgctac tgaaggtgtc      60
ggaaaagcat tttgtgaaag gcttgccaaa gaaggtatga atgtcgtaat ggtcggacgc     120
cgtgaagaaa aattaaaaga gctcggtgag gaactaaaaa acacttatga gattgattat     180
aaagtcgtaa aagcagactt ttcgctgcca gatgctactg acaaaatttt tgctgcaaca     240
gaaaatctgg atatgggatt tatggcctat gtagcctgct acactctttt ggcaaaatc      300
caggatacac cttgggaaaa gcatgaggca atgatcaacg taaacgttgt acatttatg      360
aaatgcttct atcactatat gaaaatcttt gctgcacagg atcgcggtgc tgtcatcaac     420
gtatcttcta tgactggaat ttccagttca ccatggaatg gccaatatgg tgcaggaaag     480
gcattcattt taaaaatgac agaggctgtt gcctgtgaaa cggaaaagac caatgttgat     540
gtggaagtca tcactttggg aactactctg acaccaagtc tttttaagcaa cctgcctggc     600
ggaccacagg gggaagctgt tatgaagact gctcaaacac cggaagaagt tgtggacgaa     660
gcttttgaaa aattaggaaa agaactgtct gtcatttccg gagagcgtaa taaagccagc     720
gtccatgact ggaaagcgaa tcatacagaa gatgactata tccgctatat gggatctttc     780
tatcaagaat aa                                                         792
```

<210> SEQ ID NO 56
<211> LENGTH: 263
<212> TYPE: PRT
<213> ORGANISM: Ruminococcus gnavus

<400> SEQUENCE: 56

```
Met Thr Leu Arg Glu Lys Tyr Gly Glu Trp Gly Ile Ile Leu Gly Ala
  1               5                  10                  15
Thr Glu Gly Val Gly Lys Ala Phe Cys Glu Arg Leu Ala Lys Glu Gly
                 20                  25                  30
Met Asn Val Val Met Val Gly Arg Arg Glu Glu Lys Leu Lys Glu Leu
             35                  40                  45
Gly Glu Glu Leu Lys Asn Thr Tyr Glu Ile Asp Tyr Lys Val Val Lys
         50                  55                  60
Ala Asp Phe Ser Leu Pro Asp Ala Thr Asp Lys Ile Phe Ala Ala Thr
 65                  70                  75                  80
Glu Asn Leu Asp Met Gly Phe Met Ala Tyr Val Ala Cys Leu His Ser
                 85                  90                  95
Phe Gly Lys Ile Gln Asp Thr Pro Trp Glu Lys His Glu Ala Met Ile
            100                 105                 110
Asn Val Asn Val Val Thr Phe Met Lys Cys Phe Tyr His Tyr Met Lys
        115                 120                 125
Ile Phe Ala Ala Gln Asp Arg Gly Ala Val Ile Asn Val Ser Ser Met
    130                 135                 140
Thr Gly Ile Ser Ser Ser Pro Trp Asn Gly Gln Tyr Gly Ala Gly Lys
145                 150                 155                 160
Ala Phe Ile Leu Lys Met Thr Glu Ala Val Ala Cys Glu Thr Glu Lys
                165                 170                 175
Thr Asn Val Asp Val Glu Val Ile Thr Leu Gly Thr Thr Leu Thr Pro
            180                 185                 190
Ser Leu Leu Ser Asn Leu Pro Gly Gly Pro Gln Gly Glu Ala Val Met
        195                 200                 205
Lys Thr Ala Gln Thr Pro Glu Glu Val Val Asp Glu Ala Phe Glu Lys
    210                 215                 220
```

```
Leu Gly Lys Glu Leu Ser Val Ile Ser Gly Glu Arg Asn Lys Ala Ser
225                 230                 235                 240

Val His Asp Trp Lys Ala Asn His Thr Glu Asp Asp Tyr Ile Arg Tyr
                245                 250                 255

Met Gly Ser Phe Tyr Gln Glu
            260
```

<210> SEQ ID NO 57
<211> LENGTH: 7
<212> TYPE: PRT
<213> ORGANISM: Artificial Sequence
<220> FEATURE:
<223> OTHER INFORMATION: Glycine Motif
<220> FEATURE:
<221> NAME/KEY: MISC_FEATURE
<222> LOCATION: (1)..(1)
<223> OTHER INFORMATION: X = Gly or Ala
<220> FEATURE:
<221> NAME/KEY: MISC_FEATURE
<222> LOCATION: (2)..(4)
<223> OTHER INFORMATION: X = Any Amino Acid
<220> FEATURE:
<221> NAME/KEY: MISC_FEATURE
<222> LOCATION: (6)..(6)
<223> OTHER INFORMATION: X = Any Amino Acid

<400> SEQUENCE: 57

```
Xaa Xaa Xaa Xaa Gly Xaa Gly
1               5
```

<210> SEQ ID NO 58
<211> LENGTH: 262
<212> TYPE: PRT
<213> ORGANISM: Clostridium perfringens

<400> SEQUENCE: 58

```
Met Lys Arg Leu Asp Glu Lys Ile Ala Ile Val Thr Ala Ala Ser Arg
1               5                   10                  15

Gly Ile Gly Phe Ala Cys Ala His Thr Leu Ala Met Asn Gly Ala Leu
            20                  25                  30

Val Tyr Ile Ala Gly Ile Glu Glu Gly Ala Ile Glu Lys Ile Leu
        35                  40                  45

Glu Asp Gly Gly Gln Ala Lys Phe Ile Tyr Phe Asn Ala Lys Glu Arg
    50                  55                  60

Asp Ser Tyr Phe Lys Met Ile Asp Thr Val Tyr Glu Asn Glu Gly Lys
65                  70                  75                  80

Ile Asp Ile Leu Val Asn Asn Tyr Gly Ala Thr Asn Val Lys Leu Asp
                85                  90                  95

Arg Asn Leu Val Asp Gly Asp Thr Asp Ala Phe Phe Asp Ile Leu Lys
            100                 105                 110

Ser Asn Ile Glu Ser Val Tyr Leu Thr Ser Lys Arg Thr Val Pro Tyr
        115                 120                 125

Met Ile Lys Asn Gly Gly Ser Ile Ile Asn Ile Ser Ser Val Gly
    130                 135                 140

Ser Ile Val Pro Asp Leu Ser Arg Met Ala Tyr Cys Val Ser Lys Ser
145                 150                 155                 160

Ala Ile Asn Ser Leu Thr Gln Asn Ile Ala Leu Gln Tyr Ala Lys Gln
                165                 170                 175

Asn Ile Arg Cys Asn Ala Val Leu Pro Gly Leu Ile Ala Thr Lys Ala
            180                 185                 190
```

```
Ala Leu Asn Asn Met Ser Asp Glu Phe Arg Glu Ser Phe Val Lys His
            195                 200                 205

Val Pro Leu Asn Arg Val Gly Asp Pro Gln Asp Ile Ala Asn Thr Val
    210                 215                 220

Leu Tyr Tyr Ala Ser Asp Glu Ser Asn Tyr Val Thr Gly Met Ile His
225                 230                 235                 240

Glu Val Ala Gly Gly Phe Ala Leu Gly Thr Pro Gln Tyr Ala Glu Tyr
                245                 250                 255

Met Tyr Leu Met Gly Lys
            260

<210> SEQ ID NO 59
<211> LENGTH: 259
<212> TYPE: PRT
<213> ORGANISM: Bacteroides fragilis

<400> SEQUENCE: 59

Met Asn Arg Phe Glu Asn Lys Ile Ile Ile Thr Gly Ala Ala Gly
1               5                   10                  15

Gly Ile Gly Ala Ser Thr Thr Arg Arg Ile Val Ser Glu Gly Gly Lys
                20                  25                  30

Val Val Ile Ala Asp Tyr Ser Arg Glu Lys Ala Asp Gln Phe Ala Ala
            35                  40                  45

Glu Leu Ser Asn Ser Gly Ala Asp Val Arg Pro Val Tyr Phe Ser Ala
    50                  55                  60

Thr Glu Leu Lys Ser Cys Lys Glu Leu Ile Thr Phe Thr Met Lys Glu
65                  70                  75                  80

Tyr Gly Gln Ile Asp Val Leu Val Asn Asn Val Gly Gly Thr Asn Pro
                85                  90                  95

Arg Arg Asp Thr Asn Ile Glu Thr Leu Asp Met Asp Tyr Phe Asp Glu
            100                 105                 110

Ala Phe His Leu Asn Leu Ser Cys Thr Met Tyr Leu Ser Gln Leu Val
        115                 120                 125

Ile Pro Ile Met Ser Thr Gln Gly Gly Asn Ile Val Asn Val Ala
    130                 135                 140

Ser Ile Ser Gly Ile Thr Ala Asp Ser Asn Gly Thr Leu Tyr Gly Ala
145                 150                 155                 160

Ser Lys Ala Gly Val Ile Asn Leu Thr Lys Tyr Ile Ala Thr Gln Thr
                165                 170                 175

Gly Lys Lys Asn Ile Arg Cys Asn Ala Val Ala Pro Gly Leu Ile Leu
            180                 185                 190

Thr Pro Ala Ala Leu Asn Asn Leu Asn Glu Glu Val Arg Lys Ile Phe
        195                 200                 205

Leu Gly Gln Cys Ala Thr Pro Tyr Leu Gly Glu Pro Gln Asp Val Ala
    210                 215                 220

Ala Thr Ile Ala Phe Leu Ala Ser Glu Asp Ala Arg Tyr Ile Thr Gly
225                 230                 235                 240

Gln Thr Ile Val Val Asp Gly Gly Leu Thr Ile His Asn Pro Thr Ile
                245                 250                 255

Asn Leu Val

<210> SEQ ID NO 60
<211> LENGTH: 267
<212> TYPE: PRT
<213> ORGANISM: Clostridium sordellii
```

<400> SEQUENCE: 60

Met Asn Lys Leu Glu Asn Lys Val Ala Leu Val Thr Ser Ala Thr Arg
1               5                   10                  15

Gly Ile Gly Leu Ala Ser Ala Ile Lys Leu Ala Gln Asn Gly Ala Ile
            20                  25                  30

Val Tyr Met Gly Val Arg Arg Leu Glu Ala Thr Gln Glu Ile Cys Asp
        35                  40                  45

Lys Tyr Lys Glu Glu Gly Leu Ile Leu Lys Pro Val Phe Phe Asp Ala
50                  55                  60

Tyr Asn Ile Asp Ile Tyr Lys Glu Met Ile Asp Thr Ile Ile Lys Asn
65                  70                  75                  80

Glu Gly Lys Ile Asp Ile Leu Val Asn Asn Phe Gly Thr Gly Arg Pro
                85                  90                  95

Glu Lys Asp Leu Asp Leu Val Asn Gly Asp Glu Asp Thr Phe Phe Glu
            100                 105                 110

Leu Phe Asn Tyr Asn Val Gly Ser Val Tyr Arg Leu Ser Lys Leu Ile
        115                 120                 125

Ile Pro His Met Ile Glu Asn Lys Gly Gly Ser Ile Val Asn Ile Ser
    130                 135                 140

Ser Val Gly Gly Ser Ile Pro Asp Ile Ser Arg Ile Gly Tyr Gly Val
145                 150                 155                 160

Ser Lys Ser Gly Val Asn Asn Ile Thr Lys Gln Ile Ala Ile Gln Tyr
                165                 170                 175

Ala Lys Tyr Gly Ile Arg Cys Asn Ala Val Leu Pro Gly Leu Ile Ala
            180                 185                 190

Thr Asp Ala Ala Met Asn Ser Met Pro Asp Glu Phe Arg Lys Ser Phe
        195                 200                 205

Leu Ser His Val Pro Leu Asn Arg Ile Gly Asn Pro Glu Asp Ile Ala
    210                 215                 220

Asn Ser Val Leu Phe Phe Val Pro Ser Glu Asp Ser Ser Tyr Ile Thr
225                 230                 235                 240

Gly Ser Ile Leu Glu Val Ser Gly Gly Tyr Asn Leu Gly Thr Pro Gln
                245                 250                 255

Tyr Ala Glu Phe Val Gly Ser Lys Val Val Glu
            260                 265

<210> SEQ ID NO 61
<211> LENGTH: 61
<212> TYPE: PRT
<213> ORGANISM: Clostridium difficile

<400> SEQUENCE: 61

Met Glu Lys Leu Gln Gly Lys Ile Ala Val Val Thr Ala Ala Thr Lys
1               5                   10                  15

Gly Ile Gly Leu Ala Ser Ala Glu Ile Leu Ala Lys Asn Gly Ala Thr
            20                  25                  30

Val Val Leu Ala Ala Arg Ser Glu Glu Leu Ala His Glu Val Ile Asn
        35                  40                  45

Lys Ile Ser Ala Glu Gly Gly Cys Ala Lys Phe Val Tyr
50                  55                  60

<210> SEQ ID NO 62
<211> LENGTH: 61
<212> TYPE: PRT
<213> ORGANISM: Escherichia coli

```
<400> SEQUENCE: 62

Met Phe Asn Ser Asp Asn Leu Arg Leu Asp Gly Lys Cys Ala Ile Ile
1               5                   10                  15

Thr Gly Ala Gly Ala Gly Ile Gly Lys Glu Ile Ala Ile Thr Phe Ala
            20                  25                  30

Thr Ala Gly Ala Ser Val Val Val Ser Asp Ile Asn Ala Asp Ala Ala
        35                  40                  45

Asn His Val Val Asp Glu Ile Gln Gln Leu Gly Gly Gln
    50                  55                  60

<210> SEQ ID NO 63
<211> LENGTH: 60
<212> TYPE: PRT
<213> ORGANISM: Bacteroides fragilis

<400> SEQUENCE: 63

Met Asn Arg Phe Glu Asn Lys Ile Ile Ile Thr Gly Ala Ala Gly
1               5                   10                  15

Gly Ile Gly Ala Ser Thr Thr Arg Arg Ile Val Ser Glu Gly Gly Lys
            20                  25                  30

Val Val Ile Ala Asp Tyr Ser Arg Glu Lys Ala Asp Gln Phe Ala Ala
        35                  40                  45

Glu Leu Ser Asn Ser Gly Ala Asp Val Arg Pro Val
    50                  55                  60

<210> SEQ ID NO 64
<211> LENGTH: 61
<212> TYPE: PRT
<213> ORGANISM: Pseudomonas testosteroni

<400> SEQUENCE: 64

Met Ser Ile Ile Val Ile Ser Gly Cys Ala Thr Gly Ile Gly Ala Ala
1               5                   10                  15

Thr Arg Lys Val Leu Glu Ala Ala Gly His Gln Ile Val Gly Ile Asp
            20                  25                  30

Ile Arg Asp Ala Glu Val Ile Ala Asp Leu Ser Thr Ala Glu Gly Arg
        35                  40                  45

Lys Gln Ala Ile Ala Asp Val Leu Ala Lys Cys Ser Lys
    50                  55                  60
```